US012630636B2

(12) United States Patent
Ebens et al.

(10) Patent No.: US 12,630,636 B2

(45) Date of Patent: May 19, 2026

(54) ANTI-FCRH5 ANTIBODIES

(71) Applicant: Genentech, Inc., South San Francisco, CA (US)

(72) Inventors: Allen J. Ebens, San Carlos, CA (US); Meredith C. Hazen, Belmont, CA (US); Jo-Anne Hongo, Redwood City, CA (US); Jennifer W. Johnston, San Francisco, CA (US); Teemu T. Junttila, San Mateo, CA (US); Ji Li, San Mateo, CA (US); Andrew G. Polson, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 780 days.

(21) Appl. No.: 17/734,239

(22) Filed: May 2, 2022

(65) Prior Publication Data

US 2023/0096941 A1 Mar. 30, 2023

Related U.S. Application Data

(62) Division of application No. 16/583,584, filed on Sep. 26, 2019, now Pat. No. 11,352,431, which is a division of application No. 14/313,822, filed on Jun. 24, 2014, now Pat. No. 10,435,471.

(60) Provisional application No. 61/838,534, filed on Jun. 24, 2013.

(51) Int. Cl.

| | |
|---|---|
| ***A61K 39/395*** | (2006.01) |
| ***A61K 47/68*** | (2017.01) |
| ***A61K 51/10*** | (2006.01) |
| ***C07K 16/28*** | (2006.01) |
| *A61K 39/00* | (2006.01) |
| *C07K 16/00* | (2006.01) |

(52) U.S. Cl.

CPC .......... *C07K 16/283* (2013.01); *A61K 39/395* (2013.01); *A61K 39/3955* (2013.01); *A61K 47/6849* (2017.08); *A61K 47/6879* (2017.08); *A61K 47/6889* (2017.08); *A61K 51/1045* (2013.01); *C07K 16/2896* (2013.01); *A61K 2039/505* (2013.01); *C07K 2317/24* (2013.01); *C07K 2317/33* (2013.01); *C07K 2317/56* (2013.01)

(58) Field of Classification Search

None

See application file for complete search history.

(56) References Cited

U.S. PATENT DOCUMENTS

| | | | |
|---|---|---|---|
| 4,975,278 | A | 12/1990 | Senter et al. |
| 5,767,237 | A | 6/1998 | Sakakibara et al. |
| 6,124,431 | A | 9/2000 | Sakakibara et al. |
| 6,248,564 | B1 | 6/2001 | Walter et al. |
| 7,105,149 | B1 * | 9/2006 | Dalla-Favera ..... A61K 51/1027 424/1.49 |
| 7,375,078 | B2 | 5/2008 | Feng |
| 7,491,529 | B2 | 2/2009 | Goddard et al. |
| 7,498,298 | B2 | 3/2009 | Doronina et al. |
| 7,745,394 | B2 | 6/2010 | Doronina et al. |
| 7,858,330 | B2 | 12/2010 | Hongo et al. |
| 7,863,424 | B2 | 1/2011 | Dalla-Favera |
| 7,888,478 | B2 | 2/2011 | Chang et al. |
| 7,947,839 | B2 | 5/2011 | Gazzard et al. |
| 7,964,566 | B2 | 6/2011 | Doronina et al. |
| 7,964,567 | B2 | 6/2011 | Doronina et al. |
| 7,994,135 | B2 | 8/2011 | Doronina et al. |
| 7,999,077 | B2 | 8/2011 | Pastan et al. |
| 8,142,784 | B2 | 3/2012 | Ebens, Jr. et al. |
| 8,362,213 | B2 | 1/2013 | Elkins et al. |
| 8,388,973 | B2 | 3/2013 | Chang et al. |
| 8,466,260 | B2 | 6/2013 | Elkins et al. |
| 8,617,559 | B2 | 12/2013 | Elkins et al. |
| 9,017,951 | B2 | 4/2015 | Elkins et al. |
| 9,360,484 | B2 | 6/2016 | Elkins et al. |
| 2003/0165496 | A1 | 9/2003 | Basi et al. |
| 2004/0018194 | A1 | 1/2004 | Francisco et al. |
| 2004/0253233 | A1 | 12/2004 | Del Rio et al. |
| 2005/0226869 | A1 | 10/2005 | Chang et al. |
| 2005/0238649 | A1 | 10/2005 | Doronina et al. |
| 2006/0182751 | A1 | 8/2006 | Gazzard et al. |
| 2006/0216232 | A1 | 9/2006 | Chang et al. |
| 2006/0251662 | A1 | 11/2006 | Chang et al. |
| 2007/0092940 | A1 | 4/2007 | Eigenbrot et al. |
| 2007/0134243 | A1 | 6/2007 | Gazzard et al. |
| 2007/0148176 | A1 | 6/2007 | Dalla-Favera |
| 2008/0226657 | A1 | 9/2008 | Doronina et al. |
| 2008/0247944 | A1 | 10/2008 | Graziano et al. |
| 2008/0248051 | A1 | 10/2008 | Doronina et al. |

(Continued)

FOREIGN PATENT DOCUMENTS

| | | | |
|---|---|---|---|
| CN | 102973947 | A | 3/2013 |
| EP | 1391213 | A1 | 2/2004 |

(Continued)

OTHER PUBLICATIONS

Janeway et al., Immunology Third Edition, Garland Publishing Inc. 1997, Chapter 3, Structure of the Antibody Molecule and Immunoglobulin Genes, pp. 3:1-3:11. (Year: 1997).*

Edwards et al. J. Mol. Biol., 2003, 334:103-118. (Year: 2003).*

Kanyavuz et al. Nature Review Immunology, 2019, 19: 355-368. (Year: 2019).*

Goel et al. The Journal of Immunology, 2004, 173:7358-7367. (Year: 2004).*

Bargou et al., "Tumor regression in cancer patients by very low doses of a T cell-engaging antibody," Science. 321(5891):974-7 (2008) (5 pages).

Bendayan, "Possibilities of false immunocytochemical results generated by the use of monoclonal antibodies: the example of the anti-proinsulin antibody," J Histochem Cytochem. 43(9):881-6 (1995).

(Continued)

*Primary Examiner* — Chun W Dahle

(74) *Attorney, Agent, or Firm* — Clark & Elbing LLP; Thomas J. Takara

(57) ABSTRACT

The invention provides anti-FcRH5 antibodies and immunoconjugates and methods of using the same.

14 Claims, 27 Drawing Sheets

Specification includes a Sequence Listing.

(56) References Cited

U.S. PATENT DOCUMENTS

| | | | |
|---|---|---|---|
| 2008/0248053 | A1 | 10/2008 | Doronina et al. |
| 2008/0292632 | A1 | 11/2008 | Pastan et al. |
| 2009/0047296 | A1 | 2/2009 | Doronina et al. |
| 2009/0202536 | A1 | 8/2009 | Ebens, Jr. et al. |
| 2010/0260748 | A1 | 10/2010 | Elkins et al. |
| 2011/0076287 | A1 | 3/2011 | Cohen et al. |
| 2011/0110951 | A1 | 5/2011 | Dalla-Favera |
| 2011/0256157 | A1 | 10/2011 | Howard et al. |
| 2011/0268657 | A1 | 11/2011 | Chang et al. |
| 2012/0003247 | A1 | 1/2012 | Doronina et al. |
| 2012/0003248 | A1 | 1/2012 | Doronina et al. |
| 2012/0027783 | A1 | 2/2012 | Doronina et al. |
| 2012/0027784 | A1 | 2/2012 | Doronina et al. |
| 2012/0034246 | A1 | 2/2012 | Doronina et al. |
| 2012/0034247 | A1 | 2/2012 | Doronina et al. |
| 2012/0141508 | A1 | 6/2012 | Doronina et al. |
| 2012/0141509 | A1 | 6/2012 | Doronina et al. |
| 2012/0141510 | A1 | 6/2012 | Doronina et al. |
| 2012/0148608 | A1 | 6/2012 | Doronina et al. |
| 2012/0148610 | A1 | 6/2012 | Doronina et al. |
| 2013/0089555 | A1 | 4/2013 | Elkins et al. |
| 2015/0166661 | A1 | 6/2015 | Chen et al. |
| 2016/0368985 | A1 | 12/2016 | Hotzel et al. |

FOREIGN PATENT DOCUMENTS

| | | | |
|---|---|---|---|
| JP | 2005-536439 | A | 12/2005 |
| JP | 2011-528360 | A | 11/2011 |
| JP | 2012-522513 | A | 9/2012 |
| JP | 2013-523895 | A | 6/2013 |
| RU | 2539112 | C2 | 1/2015 |
| TW | 201039846 | A | 11/2010 |
| TW | 201508008 | A | 3/2015 |
| WO | WO-01/38490 | A2 | 5/2001 |
| WO | WO-02/088172 | A2 | 11/2002 |
| WO | WO-02/102972 | A2 | 12/2002 |
| WO | WO-03/024392 | A2 | 3/2003 |
| WO | WO-03/043583 | A2 | 5/2003 |
| WO | WO-03/077836 | A2 | 9/2003 |
| WO | WO-2004/032828 | A2 | 4/2004 |
| WO | WO-2005/063299 | A2 | 7/2005 |
| WO | WO-2005/081711 | A2 | 9/2005 |
| WO | WO-2005/117986 | A2 | 12/2005 |
| WO | WO-2006/034488 | A2 | 3/2006 |
| WO | WO-2006/039238 | A2 | 4/2006 |
| WO | WO-2006/076691 | A2 | 7/2006 |
| WO | WO-2007/001851 | A2 | 1/2007 |
| WO | WO-2008/109533 | A2 | 9/2008 |
| WO | WO-2010/009124 | A2 | 1/2010 |
| WO | WO-2010/114940 | A1 | 10/2010 |
| WO | WO-2010/120561 | A1 | 10/2010 |
| WO | WO-2011/028945 | A1 | 3/2011 |
| WO | WO-2011/130598 | A1 | 10/2011 |
| WO | WO-2014/210064 | A1 | 12/2014 |
| WO | WO-2016/205520 | A1 | 12/2016 |

OTHER PUBLICATIONS

Bendig, "Humanization of rodent monoclonal antibodies by CDR grafting," Methods: A Companion to Methods in Enzymology. 8:83-93 (1995).

Bernhard et al., "Cysteine analogs of recombinant barley ribosome inactivating protein form antibody conjugates with enhanced stability and potency in vitro," Bioconjug Chem. 5(2):126-32 (1994).

Better et al., "Gelonin analogs with engineered cysteine residues form antibody immunoconjugates with unique properties," J Biol Chem. 269(13):9644-50 (1994).

Bhaskar et al., "E-selectin up-regulation allows for targeted drug delivery in prostate cancer," Cancer Res. 63(19):6387-94 (2003).

Boring et al., "Cancer statistics, 1993," CA Cancer J Clin. 43(1):7-26 (1993).

Bost et al., "Antibodies against a peptide sequence within the HIV envelope protein crossreacts with human interleukin-2," Immunol Invest. 17(6-7):577-86 (1988).

Burns et al., "A high molecular weight-melanoma associated antigen-specific chimeric antigen receptor redirects lymphocytes to target human melanomas," available in PMC Dec. 23, 2011, published in final edited form as: Cancer Res. 70(8): 3027-33 (2010) (11 pages).

Carter et al., "Humanization of an anti-p185$^{HER2}$ antibody for human cancer therapy," Proc Natl Acad Sci U S A. 89(10):4285-9 (1992).

Chen et al., "Generation and analysis of random point mutations in an antibody CDR2 sequence: many mutated antibodies lose their ability to bind antigen," J Exp Med. 176(3):855-66 (1992).

Chmura et al., "Antibodies with infinite affinity," Proc Natl Acad Sci U S A. 98(15):8480-4 (2001).

Colman, "Effects of amino acid sequence changes on antibody-antigen interactions," Res Immunol. 145(1):33-6 (1994).

Davis et al., "Identification of a family of Fc receptor homologs with preferential B cell expression," Proc Natl Acad Sci U S A. 98(17):9772-7 (2001).

Dement-Brown et al., "Fc receptor-like 5 promotes B cell proliferation and drives the development of cells displaying switched isotypes," J Leukoc Biol. 91(1):59-67 (2012) (10 pages).

Doronina et al., "Development of potent monoclonal antibody auristatin conjugates for cancer therapy," Nat Biotechnol. 21(7):778-84 (2003) (9 pages).

Dreier et al., "Extremely potent, rapid and costimulation-independent cytotoxic T-cell response against lymphoma cells catalyzed by a single-chain bispecific antibody," Int J Cancer. 100(6):690-7 (2002).

Elkins et al., "FcRL5 as a target of antibody-drug conjugates for the treatment of multiple myeloma," Mol Cancer Ther. 11(10):2222-32 (2012).

Francisco et al., "cAC10-vcMMAE, an anti-CD30-monomethyl auristatin E conjugate with potent and selective antitumor activity," Blood. 102(4):1458-65 (2003).

Greenspan et al., "Defining epitopes: It's not as easy as it seems," Nat Biotechnol. 17(10):936-7 (1999).

Greenwood et al., "Engineering multiple-domain forms of the therapeutic antibody CAMPATH-1H: effects on complement lysis," Ther Immunol. 1(5):247-55 (1994).

Güssow et al., "Humanization of monoclonal antibodies," Methods Enzymol. 203:99-121 (1991).

Hatzivassiliou et al., "IRTA1 and IRTA2, novel immunoglobulin superfamily receptors expressed in B cells and involved in chromosome 1q21 abnormalities in B cell malignancy," Immunity. 14(3):277-89 (2001).

Hinman et al., "Preparation and characterization of monoclonal antibody conjugates of the calicheamicins: a novel and potent family of antitumor antibiotics," Cancer Res. 53(14):3336-42 (1993).

Holm et al., "Functional mapping and single chain construction of the anti-cytokeratin 8 monoclonal antibody TS1," Mol Immunol. 44(6):1075-84 (2007).

Inoue et al., "Overexpression of PDZK1 within the 1q12-q22 amplicon is likely to be associated with drug-resistance phenotype in multiple myeloma," Am J Pathol. 165(1):71-81 (2004).

Ise et al., "Elevation of soluble CD307 (IRTA2/FcRH5) protein in the blood and expression on malignant cells of patients with multiple myeloma, chronic lymphocytic leukemia, and mantle cell lymphoma," Leukemia. 21(1):169-74 (2007).

Ise et al., "Immunoglobulin superfamily receptor translocation associated 2 protein on lymphoma cell lines and hairy cell leukemia cells detected by novel monoclonal antibodies," Clin Cancer Res. 11(1):87-96 (2005).

Janeway et al., Chapter 3: Structure of the Antibody Molecule and Immunoglobulin Genes, *Immunobiology, Third Edition*. Penolope Austin, Eleanor Lawrence, and Miranda Robertson, Current Biology Ltd./Garland Publishing Inc., 3:1-3:11 (1997) (14 pages).

Junutula et al., "Rapid identification of reactive cysteine residues for site-specific labeling of antibody-Fabs," J Immunol Methods. 332(1-2):41-52 (2008).

Junutula et al., "Site-specific conjugation of a cytotoxic drug to an antibody improves the therapeutic index," Nat Biotechnol. 26(8):925-32 (2008).

(56) References Cited

OTHER PUBLICATIONS

Kanno et al., "Assembling of engineered IgG-binding protein on gold surface for highly oriented antibody immobilization," J Biotechnol. 76(2-3):207-14 (2000).

Krishnan et al., "Role of antibody paratope conformational flexibility in the manifestation of molecular mimicry," Biophys J. 94(4):1367-76 (2008).

Lambert, "Drug-conjugated monoclonal antibodies for the treatment of cancer," Curr Opin Pharmacol. 5(5):543-9 (2005).

Liu et al., "Eradication of large colon tumor xenografts by targeted delivery of maytansinoids," Proc Natl Acad Sci U S A. 93(16):8618-23 (1996).

Liu et al., "Heteroantibody duplexes target cells for lysis by cytotoxic T lymphocytes," Proc Natl Acad Sci U S A. 82(24):8648-52 (1985).

Lode et al., "Targeted therapy with a novel enediyene antibiotic calicheamicin theta(I)1 effectively suppresses growth and dissemination of liver metastases in a syngeneic model of murine neuroblastoma," Cancer Res. 58(14):2925-8 (1998).

Maccallum et al., "Antibody-antigen interactions: contact analysis and binding site topography," J Mol Biol. 262(5):732-45 (1996) (14 pages).

Mandler et al., "Immunoconjugates of geldanamycin and anti-HER2 monoclonal antibodies: antiproliferative activity on human breast carcinoma cell lines," J Natl Cancer Inst. 92(19):1573-81 (2000).

Mandler et al., "Modifications in synthesis strategy improve the yield and efficacy of geldanamycin-herceptin immunoconjugates," Bioconjug Chem. 13(4):786-91 (2002).

Mandler et al., "Synthesis and evaluation of antiproliferative activity of a geldanamycin-Herceptin(TM) immunoconjugate," Bioorg Med Chem Lett. 10(10):1025-8 (2000).

Mao et al., "EphB2 as a therapeutic antibody drug target for the treatment of colorectal cancer," Cancer Res. 64(3):781-8 (2004).

Mariuzza et al., "The structural basis of antigen-antibody recognition," Annu Rev Biophys Biophys Chem. 16:139-59 (1987).

Miller et al., "IRTAs: a new family of immunoglobulinlike receptors differentially expressed in B cells," Blood. 99(8):2662-9 (2002) (9 pages).

Nakayama et al., "Altered gene expression upon BCR cross-linking in Burkitt's lymphoma B cell line," Biochem Biophys Res Commun. 277(1):124-7 (2000).

Ohno et al., "Antigen-binding specificities of antibodies are primarily determined by seven residues of VH," Proc Natl Acad Sci USA. 82(9):2945-9 (1985).

Paul, Chapter 9: Structure and Function of Immunoglobulins, *Fundamental Immunology, Third Edition.* Raven Press Ltd., 292-295 (1993) (6 pages).

Payne, "Progress in immunoconjugate cancer therapeutics," Cancer Cell. 3(3):207-12 (2003).

Polson et al., "Expression pattern of the human FcRH/IRTA receptors in normal tissue and in B-chronic lymphocytic leukemia," Int Immunol. 18(9):1363-73 (2006).

Rowland et al., "Drug localisation and growth inhibition studies of vindesine-monoclonal anti-CEA conjugates in a human tumour xenograft," Cancer Immunol Immunother. 21(3):183-7 (1986).

Rudikoff et al., "Single amino acid substitution altering antigen-binding specificity," Proc Natl Acad Sci U S A. 79(6):1979-83 (1982).

Senter et al., "Immunoconjugates comprised of drugs with impaired cellular permeability: A new approach to targeted therapy," Proc Amer Assoc Cancer Res. 45:144 Abstract 623 (2004) (1 page).

Shalaby et al., "Development of humanized bispecific antibodies reactive with cytotoxic lymphocytes and tumor cells overexpressing the HER2 protooncogene," J Exp Med. 175(1):217-25 (1992).

Springer et al., "Antibody-directed enzyme prodrug therapy (ADEPT): a review," Adv Drug Deliv Rev. 26(2-3):151-172 (1997).

Syrigos et al., "Antibody directed enzyme prodrug therapy (ADEPT): a review of the experimental and clinical considerations," Anticancer Res. 19(1A):605-13 (1999).

Tu et al., "Protein footprinting at cysteines: probing ATP-modulated contacts in cysteine-substitution mutants of yeast DNA topoisomerase II," Proc Natl Acad Sci U S A. 96(9):4862-7 (1999).

Vajdos et al., "Comprehensive functional maps of the antigen-binding site of an anti-ErbB2 antibody obtained with shotgun scanning mutagenesis," J Mol Biol. 320(2):415-28 (2002).

Wu et al., "Arming antibodies: prospects and challenges for immunoconjugates," Nat Biotechnol. 23(9):1137-46 (2005).

Zhang et al., "Complete disulfide bond assignment of a recombinant immunoglobulin G4 monoclonal antibody," Anal Biochem. 311(1):1-9 (2002).

Zhu et al., "Engineering high affinity humanized anti-p185HER2/anti-CD3 bispecific F(ab')2 for efficient lysis of p185HER2 overexpressing tumor cells," Int J Cancer. 62(3):319-24 (1995).

Communication pursuant to Article 94(3) EPC for European Patent Application No. 17198415.6, dated Jul. 12, 2019 (4 pages).

Decision to Grant for Russian Patent Application No. 2016101965, dated Feb. 1, 2019 (45 pages).

Decision of The Intellectual Property Office for Taiwanese Patent Application No. 103121621, dated Sep. 19, 2019 (12 pages).

English Translation of Decision of Final Rejection for Chinese Patent Application No. 201480045475.0, dated Apr. 2, 2020 (13 pages).

English Translation of Office Action for Chinese Patent Application No. 201480045475.0, dated Oct. 9, 2018 (9 pages).

English Translation of Search Report for Chinese Patent Application No. 201480045475.0, dated Sep. 27, 2018 (2 pages).

English Translation of the Second Office Action for Chinese Patent Application No. 201480045475.0, issued Sep. 3, 2019 (9 pages).

Examination Report for Australian Patent Application No. 2014302617, dated Dec. 18, 2018 (3 pages).

Examination Report for Gulf Cooperation Council Patent Application No. 2014-36569, dated for Mar. 5, 2020 (4 pages).

Examination Report for Gulf Cooperation Council Patent Application No. GC 2014-36569, dated Jun. 30, 2019 (4 pages).

International Preliminary Report on Patentability issued Dec. 19, 2017, for Hotzel et al., "Humanized and Affinity Matured Antibodies to FCRH5 and Methods of Use," International Patent Application No. PCT/US2016/037879, filed Jun. 16, 2016 (12 pages).

International Search Report and Written Opinion for International Patent Application No. PCT/US2010/029516, mailed Aug. 23, 2010 (18 pages).

International Search Report and Written Opinion for International Patent Application No. PCT/US2010/029521, mailed Jul. 20, 2010 (16 pages).

International Search Report and Written Opinion for International Patent Application No. PCT/US2014/043952, mailed Oct. 7, 2014 (13 pages).

Notice of Preliminary Rejection for Korean Patent Application No. 10-2011-7025864, mailed Nov. 21, 2016 (19 pages).

Notice of Preliminary Rejection for Korean Patent Application No. 10-2016-7001897, dated Sep. 10, 2020 (15 pages).

Notice of Reasons for Rejection for Japanese Patent Application No. 2016-521907, issued Jun. 12, 2018 (16 pages).

Objection filed by Asociación Industrial de Laboratorios Farmacéuticos AG against Chilean Patent Application No. 2417-2011, dated Mar. 30, 2012 (6 pages).

Office Action and Search Report for Taiwanese Application No. 103121621, dated Feb. 11, 2019 (16 pages).

Office Action for Canadian Patent Application No. 2,915,480, dated Jun. 1, 2020 (6 pages).

Official Action for Mexican Patent Application No. MX/a/2015/017331, dated Aug. 20, 2019 (4 pages).

Office Action for Russian Patent Application No. 2016101965, dated Dec. 4, 2017 (6 pages).

Search Report for Singaporean Patent Application No. 11201510653Y, dated Nov. 9, 2016 (3 pages).

Written Opinion for Singaporean Patent Application No. 11201510653Y, dated Dec. 12, 2016 (7 pages).

* cited by examiner

Structure and Homology of FcRH5 Amino Acids 735 to 977

Disulfide bond

1 VAVPVSRPVL TLRAPGTHAA VGDLLELHCE ALRGSPLILY RFFHEDVTLG NRSSPSGGAS LNLSLTAEHS GNYSCEADNG LGAQRSETVT LYITGLTANR

101 SGPFATGVAG GLLSIAGLAA GALLLYCWLS RKAGRKPASD PARSPSDSDS QEPTYHNVPA WEELQPVYTN ANPRGENVVY SEVRIIQEKK KHAVASDPRH

^TM Domain

201 LRNKGSPIIY SEVKVASTPV SGSLFLASSA PHR

* Potential N-linked glycosylation site

FIG. 1B

| | EC50 ng/ml |
|---|---|
| 2H7 TDB | 5.0 |
| 2H7 BisFab | 2.5 |
| 3G7 TDB | 1.8 |
| 3G7 Bis Fab | 1.8 |

| | EC50 ng/ml |
|---|---|
| 5A10 TDB | 2.7 |
| 2H7 BisFab | 2.1 |

| | EC50 |
|---|---|
| 2H7.TDB | 273 pM |
| 2H7.BisFab | 285 pM |
| 3G7.TDB | 335 pM |
| 3G7.BisFab | 190 pM |

FIG. 10A

Kabat CDR L1 (HVR-L1)

| | 24 | 25 | 26 | 27 | 27A | 27B | 27C | 27D | 27E | 27F | 28 | 29 | 30 | 31 | 32 | 33 | 34 | SEQ ID NO: |
|---|---|---|---|---|---|---|---|---|---|---|---|---|---|---|---|---|---|---|
| 1C8.1 | K | A | S | Q | . | . | . | . | . | . | N | V | I | T | N | V | A | 2 |
| 1G7.2 | K | A | S | Q | . | . | . | . | . | . | D | V | S | N | I | V | Y | 3 |
| 2H7.3 | R | A | S | Q | . | . | . | . | . | . | K | I | R | N | N | L | H | 4 |
| 3A4.2 | R | A | S | Q | . | . | . | . | . | . | S | I | S | N | N | L | H | 5 |
| 3B12.1.1 | R | A | S | E | . | . | . | . | . | . | N | I | Y | S | N | L | A | 6 |
| 3C10 | R | S | S | Q | S | L | V | H | R | . | N | G | N | T | Y | L | H | 7 |
| 3F10 | R | A | S | E | . | . | . | . | . | . | N | I | Y | S | N | L | A | 8 |
| 3G3 | R | A | S | E | . | . | . | . | . | . | N | I | Y | S | N | L | A | 9 |
| 3G7.1.5 | R | A | S | Q | . | . | . | . | . | . | S | I | S | N | N | L | H | 10 |
| 5A10.1.3 | R | A | S | Q | . | . | . | . | . | . | K | I | R | N | N | L | H | 11 |
| 5F1.1.5 | R | S | S | T | G | T | V | . | . | . | T | T | S | N | F | A | N | 12 |
| 6D2 | K | A | S | Q | . | . | . | . | . | . | D | V | G | T | A | V | A | 13 |

FIG. 10B

Kabat CDR L2 (HVR-L2)

| | 50 | 51 | 52 | 53 | 54 | 54A | 54B | 54C | 54D | 54E | 55 | 56 | SEQ ID NO: |
|---|---|---|---|---|---|---|---|---|---|---|---|---|---|
| 1C8.1 | S | A | S | Y | R | . | . | . | . | . | Y | S | 14 |
| 1G7.2 | S | A | S | Y | R | . | . | . | . | . | Y | T | 15 |
| 2H7.3 | F | T | S | Q | S | . | . | . | . | . | I | S | 16 |
| 3A4.2 | F | A | S | Q | S | . | . | . | . | . | I | S | 17 |
| 3B12.1.1 | G | A | A | N | L | . | . | . | . | . | A | E | 18 |
| 3C10 | K | V | S | N | R | . | . | . | . | . | F | S | 19 |
| 3F10 | G | A | A | N | L | . | . | . | . | . | A | E | 20 |
| 3G3 | G | A | A | N | L | . | . | . | . | . | A | E | 21 |
| 3G7.1.5 | F | A | S | Q | S | . | . | . | . | . | I | S | 22 |
| 5A10.1.3 | F | A | S | Q | S | . | . | . | . | . | M | S | 23 |
| 5F1.1.5 | G | T | S | N | R | . | . | . | . | . | A | P | 24 |
| 6D2 | W | P | S | T | R | . | . | . | . | . | H | T | 25 |

FIG. 10C

Kabat CDR L3 (HVR-L3)

| | 89 | 90 | 91 | 92 | 93 | 94 | 95 | 95A | 95B | 95C | 95D | 95E | 95F | 96 | 97 | SEQ ID NO: |
|---|---|---|---|---|---|---|---|---|---|---|---|---|---|---|---|---|
| 1C8.1 | Q | Q | Y | T | N | Y | P | M | . | . | . | . | . | W | T | 26 |
| 1G7.2 | Q | Q | H | Y | S | S | P | . | . | . | . | . | . | Y | T | 27 |
| 2H7.3 | Q | Q | S | N | N | W | P | Q | . | . | . | . | . | Y | T | 28 |
| 3A4.2 | Q | Q | S | N | N | W | P | Q | . | . | . | . | . | Y | T | 29 |
| 3B12.1.1 | Q | H | F | W | G | I | P | . | . | . | . | . | . | W | T | 30 |
| 3C10 | S | Q | S | T | H | V | P | . | . | . | . | . | . | F | T | 31 |
| 3F10 | Q | H | F | W | G | I | P | . | . | . | . | . | . | W | T | 32 |
| 3G3 | Q | H | F | W | G | I | P | . | . | . | . | . | . | W | T | 33 |
| 3G7.1.5 | Q | Q | S | N | N | W | P | Q | . | . | . | . | . | Y | T | 34 |
| 5A10.1.3 | Q | Q | S | N | N | W | P | Q | . | . | . | . | . | Y | T | 35 |
| 5F1.1.5 | V | L | W | C | S | N | L | . | . | . | . | . | . | W | V | 36 |
| 6D2 | Q | Q | F | S | S | L | P | . | . | . | . | . | . | H | T | 37 |

FIG. 11A

Kabat CDR H1 (HVR-H1)

| | 31 | 32 | 33 | 34 | 35 | 35A | 35B | SEQ ID NO: |
|---|---|---|---|---|---|---|---|---|
| 1C8.1 | A | Y | I | M | N | . | . | 38 |
| 1G7.2 | R | F | G | V | H | . | . | 39 |
| 2H7.3 | D | Y | Y | M | K | . | . | 40 |
| 3A4.2 | D | Y | Y | M | K | . | . | 41 |
| 3B12.1.1 | E | Y | T | I | H | . | . | 42 |
| 3C10 | S | Y | W | I | N | . | . | 43 |
| 3F10 | E | Y | T | I | H | . | . | 44 |
| 3G3 | E | Y | T | I | H | . | . | 45 |
| 3G7.1.5 | D | Y | Y | M | K | . | . | 46 |
| 5A10.1.3 | D | Y | Y | M | K | . | . | 47 |
| 5F1.1.5 | N | Y | L | I | E | . | . | 48 |
| 6D2 | A | Y | F | M | N | . | . | 49 |

CDR H1 (HVR-H1)

| | 26 | 27 | 28 | 29 | 30 | 31 | 32 | 33 | 34 | 35 | 35A | 35B | SEQ ID NO: |
|---|---|---|---|---|---|---|---|---|---|---|---|---|---|
| 1C8.1 | G | Y | S | F | T | A | Y | I | M | N | . | . | 50 |
| 1G7.2 | G | F | S | L | T | R | F | G | V | H | . | . | 51 |
| 2H7.3 | G | Y | T | F | T | D | Y | Y | M | K | . | . | 52 |
| 3A4.2 | G | Y | T | F | T | D | Y | Y | M | K | . | . | 53 |
| 3B12.1.1 | G | Y | T | F | T | E | Y | T | I | H | . | . | 54 |
| 3C10 | G | Y | T | F | I | S | Y | W | I | N | . | . | 55 |
| 3F10 | G | Y | T | F | T | E | Y | T | I | H | . | . | 56 |
| 3G3 | G | Y | T | F | T | E | Y | T | I | H | . | . | 57 |
| 3G7.1.5 | G | Y | T | F | T | D | Y | Y | M | K | . | . | 58 |
| 5A10.1.3 | G | Y | T | F | T | D | Y | Y | M | K | . | . | 59 |
| 5F1.1.5 | G | Y | A | F | T | N | Y | L | I | E | . | . | 60 |
| 6D2 | G | F | S | F | T | A | Y | F | M | N | . | . | 61 |

FIG. 11B

Kabat CDR H2 (HVR-H2)

| | 50 | 51 | 52 | 52A | 52B | 52C | 53 | 54 | 55 | 56 | 57 | 58 | 59 | 60 | 61 | 62 | 63 | 64 | 65 | SEQ ID NO: |
|---|---|---|---|---|---|---|---|---|---|---|---|---|---|---|---|---|---|---|---|---|
| 1C8.1 | E | I | N | P | . | . | Y | N | G | E | T | T | Y | N | Q | K | F | K | G | 62 |
| 1G7.2 | V | I | W | . | . | . | R | G | G | S | T | D | Y | N | A | A | F | M | S | 63 |
| 2H7.3 | D | I | N | P | . | . | N | N | G | E | T | F | Y | S | Q | K | F | K | G | 64 |
| 3A4.2 | D | I | N | P | . | . | Y | N | G | E | T | F | Y | N | Q | K | L | K | G | 65 |
| 3B12.1.1 | G | I | N | P | . | . | N | N | D | A | V | S | Y | N | Q | R | F | R | G | 66 |
| 3C10 | N | I | Y | P | . | . | S | D | S | Y | T | N | Y | N | Q | K | F | K | D | 67 |
| 3F10 | G | I | N | P | . | . | N | N | D | A | I | S | Y | N | Q | K | F | R | G | 68 |
| 3G3 | R | I | N | P | . | . | N | N | D | A | I | S | Y | N | Q | K | F | R | G | 69 |
| 3G7.1.5 | D | I | N | P | . | . | Y | N | G | D | T | F | Y | N | Q | K | F | K | D | 70 |
| 5A10.1.3 | D | I | N | P | . | . | N | N | G | E | T | F | Y | N | Q | K | F | K | G | 71 |
| 5F1.1.5 | V | I | N | P | . | . | G | S | G | G | T | N | Y | N | E | K | F | K | G | 72 |
| 6D3 | R | I | N | P | . | . | Y | N | G | E | T | F | F | N | Q | N | F | K | D | 73 |

CDR H2 (HVR-H2)

| | 49 | 50 | 51 | 52 | 52A | 52B | 52C | 53 | 54 | 55 | 56 | 57 | 58 | 59 | 60 | 61 | 62 | 63 | 64 | 65 | SEQ ID NO: |
|---|---|---|---|---|---|---|---|---|---|---|---|---|---|---|---|---|---|---|---|---|---|
| 1C8.1 | G | E | I | N | P | . | . | Y | N | G | E | T | T | Y | N | Q | K | F | K | G | 74 |
| 1G7.2 | G | V | I | W | . | . | . | R | G | G | S | T | D | Y | N | A | A | F | M | S | 75 |
| 2H7.3 | G | D | I | N | P | . | . | N | N | G | E | T | F | Y | S | Q | K | F | K | G | 76 |
| 3A4.2 | G | D | I | N | P | . | . | Y | N | G | E | T | F | Y | N | Q | K | L | K | G | 77 |
| 3B12.1.1 | G | G | I | N | P | . | . | N | N | D | A | V | S | Y | N | Q | R | F | R | G | 78 |
| 3C10 | G | N | I | Y | P | . | . | S | D | S | Y | T | N | Y | N | Q | K | F | K | D | 79 |
| 3F10 | G | G | I | N | P | . | . | N | N | D | A | I | S | Y | N | Q | K | F | R | G | 80 |
| 3G3 | G | R | I | N | P | . | . | N | N | D | A | I | S | Y | N | Q | K | F | R | G | 81 |
| 3G7.1.5 | G | D | I | N | P | . | . | Y | N | G | D | T | F | Y | N | Q | K | F | K | D | 82 |
| 5A10.1.3 | G | D | I | N | P | . | . | N | N | G | E | T | F | Y | N | Q | K | F | K | G | 83 |
| 5F1.1.5 | G | V | I | N | P | . | . | G | S | G | G | T | N | Y | N | E | K | F | K | G | 84 |
| 6D3 | G | R | I | N | P | . | . | Y | N | G | E | T | F | F | N | Q | N | F | K | D | 85 |

FIG. 11C

Kabat CDR H3 (HVR-H3)

| | 95 | 96 | 97 | 98 | 99 | 100 | 100A | 100B | 100C | 100D | 100E | 100F | 100G | 100H | 100I | 100J | 100K | 100L | 100M | 101 | 102 | SEQ ID NO: |
|---|---|---|---|---|---|---|---|---|---|---|---|---|---|---|---|---|---|---|---|---|---|---|
| 1C8.1 | G | L | R | . | . | . | . | . | . | . | . | . | . | . | . | . | . | W | F | R | Y | 86 |
| 1G7.2 | R | Y | Y | G | S | S | G | . | . | . | . | . | . | . | . | . | Y | A | L | D | N | 87 |
| 2H7.3 | R | L | Y | R | . | . | . | . | . | . | . | . | . | . | . | . | . | . | F | D | Y | 88 |
| 3A4.2 | G | L | Y | F | . | . | . | . | . | . | . | . | . | . | . | . | . | . | F | A | Y | 89 |
| 3B12.1.1 | L | G | R | G | Y | . | . | . | . | . | . | . | . | . | . | . | . | Y | F | D | Y | 90 |
| 3C10 | S | L | Y | G | Y | D | R | S | . | . | . | . | . | . | . | . | . | Y | F | D | Y | 91 |
| 3F10 | L | G | R | N | Y | . | . | . | . | . | . | . | . | . | . | . | . | Y | F | D | Y | 92 |
| 3G3 | L | G | R | G | Y | . | . | . | . | . | . | . | . | . | . | . | . | Y | F | D | Y | 93 |
| 3G7.1.5 | G | L | Y | F | . | . | . | . | . | . | . | . | . | . | . | . | . | . | F | N | Y | 94 |
| 5A10.1.3 | G | L | Y | R | . | . | . | . | . | . | . | . | . | . | . | . | . | . | F | D | Y | 95 |
| 5F1.1.5 | T | R | R | Y | G | Y | V | . | . | . | . | . | . | . | . | . | . | . | I | D | Y | 96 |
| 6D2 | G | L | R | . | . | . | . | . | . | . | . | . | . | . | . | . | . | Y | L | N | Y | 97 |

CDR H3 (HVR-H3)

| | 93 | 94 | 95 | 96 | 97 | 98 | 99 | 100 | 100A | 100B | 100C | 100D | 100E | 100F | 100G | 100H | 100I | 100J | 100K | 100L | 100M | 101 | 102 | SEQ ID NO: |
|---|---|---|---|---|---|---|---|---|---|---|---|---|---|---|---|---|---|---|---|---|---|---|---|---|
| 1C8.1 | A | R | G | L | R | . | . | . | . | . | . | . | . | . | . | . | . | . | . | W | F | R | Y | 98 |
| 1G7.2 | S | N | R | Y | Y | G | S | S | G | . | . | . | . | . | . | . | . | . | Y | A | L | D | N | 99 |
| 2H7.3 | A | R | R | L | Y | R | . | . | . | . | . | . | . | . | . | . | . | . | . | . | F | D | Y | 100 |
| 3A4.2 | A | R | G | L | Y | F | . | . | . | . | . | . | . | . | . | . | . | . | . | . | F | A | Y | 101 |
| 3B12.1.1 | A | K | L | G | R | G | Y | . | . | . | . | . | . | . | . | . | . | . | . | Y | F | D | Y | 102 |
| 3C10 | T | R | S | L | Y | G | Y | D | R | S | . | . | . | . | . | . | . | . | . | Y | F | D | Y | 103 |
| 3F10 | A | K | L | G | R | N | Y | . | . | . | . | . | . | . | . | . | . | . | . | Y | F | D | Y | 104 |
| 3G3 | A | K | L | G | R | G | Y | . | . | . | . | . | . | . | . | . | . | . | . | Y | F | D | Y | 105 |
| 3G7.1.5 | A | R | G | L | Y | F | . | . | . | . | . | . | . | . | . | . | . | . | . | . | F | N | Y | 106 |
| 5A10.1.3 | A | R | G | L | Y | R | . | . | . | . | . | . | . | . | . | . | . | . | . | . | F | D | Y | 107 |
| 5F1.1.5 | A | R | T | R | R | Y | G | Y | V | . | . | . | . | . | . | . | . | . | . | . | I | D | Y | 108 |
| 6D2 | G | R | G | L | R | . | . | . | . | . | . | . | . | . | . | . | . | . | . | Y | L | N | Y | 109 |

ANTI-FCRH5 ANTIBODIES

RELATED APPLICATIONS

The present application is a division of U.S. patent application Ser. No. 16/583,584, now U.S. Pat. No. 11,352,431, filed on Sep. 26, 2019, which is a division of U.S. patent application Ser. No. 14/313,822, now U.S. Pat. No. 10,435,471, filed on Jun. 24, 2014, which claims benefit under 35 U.S.C. § 119 of U.S. Provisional Patent Application No. 61/838,534, filed on Jun. 24, 2013, the disclosure of which is hereby incorporated by reference in its entirety.

SEQUENCE LISTING

The instant application contains a Sequence Listing which has been submitted electronically in ASCII format and is hereby incorporated by reference in its entirety. The ASCII text file was created on Apr. 29, 2022, is named 50474-145004_Sequence_Listing_4_29_22_ST25, and is 67,986 bytes in size.

FIELD OF THE INVENTION

Provided herein are anti-FcRH5 antibodies (e.g., bispecific antibodies) and immunoconjugates and methods of using the same.

BACKGROUND

The Fc receptor-like 5 (FcRL5, also known as FcRH5 and IRTA2) belongs to a family of 6 recently identified genes of the immunoglobulin superfamily (IgSF). This family of genes is closely related to the Fc receptors with the conserved genomic structure, extracellular Ig domain composition and the ITIM- and ITAM-like signaling motifs (Davis R S et al., *Eur J Immunol* (2005) 35:674-80). Members of this family have also been called IFGPs (from Ig superfamily, FcR, gp42) and SPAPs (SH2 domain-containing phosphatases anchor proteins). Six members of the FcRH/IRTA receptor family have been described: FcRH1/IRTA5, FcRH2/IRTA4, FcRH3/IRTA3, FcRH4/IRTA1, FcRH5/IRTA2 and FcRH6 (Polson A G et al., *Int. Immunol.* (2006) 18(9):1363-1373). All FcRH/IRTAs contain some combination of canonical immunoreceptor tyrosine-based inhibitory motifs and 'immunoreceptor tyrosine-based activation motifs-like' signaling motifs. The FcRH cDNAs encode type I transmembrane glycoproteins with multiple Ig-like extracellular domains and cytoplasmic domains containing consensus immunoreceptor tyrosine-based activating and/or inhibitory signaling motifs. The FcRH genes are structurally related, and their protein products share 28-60% extracellular identity with each other. They also share 15-31% identity with their closest FcR relatives. There is a high degree of homology between the different FcRHs.

The ligand(s) for FcRH5 are unknown, but FcRH5 has been implicated in enhanced proliferation and downstream isotype expression during the development of antigen-primed B-cells (Dement-Brown J. et al. *J Leukoc Biol* (2012) 91:59-67). The FcRH5 locus has three major mRNA isoforms (FcRH5a, FcRH5b, and FcRH5c). The major FcRH5 protein isoforms encoded by these transcripts share a common amino acid sequence until residue 560, featuring a common signal peptide and six extracellular Ig-like domains. FcRH5a represents a 759 amino acid secreted glycoprotein with eight Ig-like domains followed by 13 unique, predominantly polar amino acids at its C-terminus.

FcRH5b diverges from FcRH5a at amino acid residue 560 and extends for a short stretch of 32 additional residues, whose hydrophobicity is compatible with its docking to the plasma membranevia a GPI anchor. FcRH5c is the longest isoform whose sequence deviates from FcRH5a at amino acid 746. FcRH5c encodes a 977 aa type I transmembrane glycoprotein with nine extracellular Ig-type domains, harboring eight potential N-linked glycosylation sites, a 23 amino acid transmembrane, and a 104 amino acid cytoplasmic domain with three consensus SH2 binding motifs with the ITIM consensus.

The FcRH genes are clustered together in the midst of the classical FcR genes, FcγRI, FcγRII, FcγRIII, and FcεRI, in the 1q21-23 region of chromosome 1. This region contains 1 of the most frequent secondary chromosomal abnormalities associated with malignant phenotype in hematopoietic tumors, especially in multiple myeloma (Hatzivassiliou G et al. *Immunity* (2001) 14:277-89). FcRH5 is expressed only in the B-cell lineage, starting as early as pre-B-cells, but does not attain full expression until the mature B-cell stage. Unlike most knownother B-cell-specific surface proteins (e.g., CD20, CD19, and CD22), FcRH5 continues to be expressed in plasma cells whereas other B-cell-specific markers are downregulated (Polson A G et al., *Int Immunol* (2006) 18:1363-73). In addition, FcRH5 mRNA is overexpressed in multiple myeloma cell lines with 1q21 abnormalities as detected by oligonucleotide arrays (Inoue J., *Am J Pathol* (2004) 165:71-81). The expression pattern indicates that FcRH5 could be a target for antibody-based therapies for the treatment of multiple myeloma. Multiple myeloma is a malignancy of plasma cells characterized by skeletal lesions, renal failure, anemia, and hypercalcemia. It is essentially incurable by current therapies. Current drug treatments for multiple myeloma include combinations of the proteosome inhibitor bortezomib (Velcade), the immunomodulator lenalidomide (Revlimid), and the steroid dexamethasone.

FcRH5c specific antibody-based therapies and detection methods may be particularly efficacious as they specifically recognize target cell, membrane-associated FcRH5 rather than antibodies which recognize both soluble and membrane isoforms of FcRH5. However, only the last Ig-like domain of FcRH5 (Ig-like domain 9) is unique extracellular region that differentiates between the three major isoforms of FcRH5, and there is significant homology between the Ig-like domains within FcRH5. Further, the last Ig-like domain is highly conserved between FcRH1, FcRH2, FcRH3, and FcRH5. Any antibody-based therapy that specifically targeted FcRH5 would have to have minimal cross-reactivity with other FcRHs to avoid adverse off-target effects (e.g., FcRH3 is expressed on normal NK cells). There is a need in the art for agents that aid in the diagnosis and treatment of cancer, such as FcRH5-associated cancer.

SUMMARY

Provided herein are anti-FcRH5 antibodies including bispecific antibodies, immunoconjugates, and methods of using the same. Provided herein are isolated anti-FcRH5 antibodies that binds an isoform c-specific region of the extracellular domain of FcRH5c. In some embodiments, the isoform c-specific region comprises Ig-like domain 9. In some embodiments, the isoform c-specific region comprises amino acids 743-850 of SEQ ID NO:1.

In some embodiments, the antibody comprises: a) a heavy chain comprising a HVR-H1 comprising the amino acid sequence of SEQ ID NO:38, HVR-H2 comprising the amino acid sequence of SEQ ID NO:62, and HVR-H3 comprising the amino acid sequence of SEQ ID NO:86; and/or b) a light chain comprising a HVR-L1 comprising the amino acid sequence of SEQ ID NO:2, HVR-L2 comprising the amino acid sequence of SEQ ID NO: 14, and HVR-L3 comprising the amino acid sequence of SEQ ID NO:26. In some embodiments, the heavy chain comprising a HVR-H1 comprising the amino acid sequence of SEQ ID NO:50, HVR-H2 comprising the amino acid sequence of SEQ ID NO:74, and HVR-H3 comprising the amino acid sequence of SEQ ID NO:98.

In some embodiments, the antibody comprises: a) a heavy chain comprising a HVR-H1 comprising the amino acid sequence of SEQ ID NO:39, HVR-H2 comprising the amino acid sequence of SEQ ID NO:63, and HVR-H3 comprising the amino acid sequence of SEQ ID NO:87; and/or b) a light chain comprising a HVR-L1 comprising the amino acid sequence of SEQ ID NO:3, HVR-L2 comprising the amino acid sequence of SEQ ID NO: 15, and HVR-L3 comprising the amino acid sequence of SEQ ID NO:27. In some embodiments, the heavy chain comprising a HVR-H1 comprising the amino acid sequence of SEQ ID NO:51, HVR-H2 comprising the amino acid sequence of SEQ ID NO:75, and HVR-H3 comprising the amino acid sequence of SEQ ID NO:99.

In some embodiments, the antibody comprises: a) a heavy chain comprising a HVR-H1 comprising the amino acid sequence of SEQ ID NO:40, HVR-H2 comprising the amino acid sequence of SEQ ID NO:64, and HVR-H3 comprising the amino acid sequence of SEQ ID NO:88; and/or b) a light chain comprising a HVR-L1 comprising the amino acid sequence of SEQ ID NO:4, HVR-L2 comprising the amino acid sequence of SEQ ID NO: 16, and HVR-L3 comprising the amino acid sequence of SEQ ID NO:28. In some embodiments, the heavy chain comprising a HVR-H1 comprising the amino acid sequence of SEQ ID NO:52, HVR-H2 comprising the amino acid sequence of SEQ ID NO:76, and HVR-H3 comprising the amino acid sequence of SEQ ID NO: 100.

In some embodiments, the antibody comprises: a) a heavy chain comprising a HVR-H1 comprising the amino acid sequence of SEQ ID NO:41, HVR-H2 comprising the amino acid sequence of SEQ ID NO:65, and HVR-H3 comprising the amino acid sequence of SEQ ID NO:89; and/or b) a light chain comprising a HVR-L1 comprising the amino acid sequence of SEQ ID NO:5, HVR-L2 comprising the amino acid sequence of SEQ ID NO: 17, and HVR-L3 comprising the amino acid sequence of SEQ ID NO:29. In some embodiments, the heavy chain comprising a HVR-H1 comprising the amino acid sequence of SEQ ID NO:53, HVR-H2 comprising the amino acid sequence of SEQ ID NO:77, and HVR-H3 comprising the amino acid sequence of SEQ ID NO:101.

In some embodiments, the antibody comprises: a) a heavy chain comprising a HVR-H1 comprising the amino acid sequence of SEQ ID NO:42, HVR-H2 comprising the amino acid sequence of SEQ ID NO:66, and HVR-H3 comprising the amino acid sequence of SEQ ID NO:90; and/or b) a light chain comprising a HVR-L1 comprising the amino acid sequence of SEQ ID NO:6, HVR-L2 comprising the amino acid sequence of SEQ ID NO: 18, and HVR-L3 comprising the amino acid sequence of SEQ ID NO:30. In some embodiments, the heavy chain comprising a HVR-H1 comprising the amino acid sequence of SEQ ID NO:54, HVR-H2 comprising the amino acid sequence of SEQ ID NO:78, and HVR-H3 comprising the amino acid sequence of SEQ ID NO: 102.

In some embodiments, the antibody comprises: a) a heavy chain comprising a HVR-H1 comprising the amino acid sequence of SEQ ID NO:43, HVR-H2 comprising the amino acid sequence of SEQ ID NO:67, and HVR-H3 comprising the amino acid sequence of SEQ ID NO:91; and/or b) a light chain comprising a HVR-L1 comprising the amino acid sequence of SEQ ID NO:7, HVR-L2 comprising the amino acid sequence of SEQ ID NO: 19, and HVR-L3 comprising the amino acid sequence of SEQ ID NO:31. In some embodiments, the heavy chain comprising a HVR-H1 comprising the amino acid sequence of SEQ ID NO:55, HVR-H2 comprising the amino acid sequence of SEQ ID NO:79, and HVR-H3 comprising the amino acid sequence of SEQ ID NO: 103.

In some embodiments, the antibody comprises: a) a heavy chain comprising a HVR-H1 comprising the amino acid sequence of SEQ ID NO:44, HVR-H2 comprising the amino acid sequence of SEQ ID NO:68, and HVR-H3 comprising the amino acid sequence of SEQ ID NO:92; and/or b) a light chain comprising a HVR-L1 comprising the amino acid sequence of SEQ ID NO:8, HVR-L2 comprising the amino acid sequence of SEQ ID NO:20, and HVR-L3 comprising the amino acid sequence of SEQ ID NO:32. In some embodiments, the heavy chain comprising a HVR-H1 comprising the amino acid sequence of SEQ ID NO:56, HVR-H2 comprising the amino acid sequence of SEQ ID NO:80, and HVR-H3 comprising the amino acid sequence of SEQ ID NO: 104.

In some embodiments, the antibody comprises: a) a heavy chain comprising a HVR-H1 comprising the amino acid sequence of SEQ ID NO:45, HVR-H2 comprising the amino acid sequence of SEQ ID NO:69, and HVR-H3 comprising the amino acid sequence of SEQ ID NO:93; and/or b) a light chain comprising a HVR-L1 comprising the amino acid sequence of SEQ ID NO:9, HVR-L2 comprising the amino acid sequence of SEQ ID NO:21, and HVR-L3 comprising the amino acid sequence of SEQ ID NO:33. In some embodiments, the heavy chain comprising a HVR-H1 comprising the amino acid sequence of SEQ ID NO:57, HVR-H2 comprising the amino acid sequence of SEQ ID NO:81, and HVR-H3 comprising the amino acid sequence of SEQ ID NO: 105.

In some embodiments, the antibody comprises: a) a heavy chain comprising a HVR-H1 comprising the amino acid sequence of SEQ ID NO:46, HVR-H2 comprising the amino acid sequence of SEQ ID NO:70, and HVR-H3 comprising the amino acid sequence of SEQ ID NO:94; and/or b) a light chain comprising a HVR-L1 comprising the amino acid sequence of SEQ ID NO: 10, HVR-L2 comprising the amino acid sequence of SEQ ID NO:22, and HVR-L3 comprising the amino acid sequence of SEQ ID NO:34. In some embodiments, the heavy chain comprising a HVR-H1 comprising the amino acid sequence of SEQ ID NO:58, HVR-H2 comprising the amino acid sequence of SEQ ID NO:82, and HVR-H3 comprising the amino acid sequence of SEQ ID NO: 106.

In some embodiments, the antibody comprises: a) a heavy chain comprising a HVR-H1 comprising the amino acid sequence of SEQ ID NO:47, HVR-H2 comprising the amino acid sequence of SEQ ID NO:71, and HVR-H3 comprising the amino acid sequence of SEQ ID NO:95; and/or b) a light chain comprising a HVR-L1 comprising the amino acid sequence of SEQ ID NO: 11, HVR-L2 comprising the amino acid sequence of SEQ ID NO:23, and HVR-L3 comprising the amino acid sequence of SEQ ID NO:35. In some embodiments, the heavy chain comprising a HVR-H1 comprising the amino acid sequence of SEQ ID NO:59, HVR- H2 comprising the amino acid sequence of SEQ ID NO:83, and HVR-H3 comprising the amino acid sequence of SEQ ID NO: 107.

In some embodiments, the antibody comprises: a) a heavy chain comprising a HVR-H1 comprising the amino acid sequence of SEQ ID NO:48, HVR-H2 comprising the amino acid sequence of SEQ ID NO:72, and HVR-H3 comprising the amino acid sequence of SEQ ID NO:96; and/or b) a light chain comprising a HVR-L1 comprising the amino acid sequence of SEQ ID NO: 12, HVR-L2 comprising the amino acid sequence of SEQ ID NO:24, and HVR-L3 comprising the amino acid sequence of SEQ ID NO:36. In some embodiments, the heavy chain comprising a HVR-H1 comprising the amino acid sequence of SEQ ID NO:60, HVR-H2 comprising the amino acid sequence of SEQ ID NO:84, and HVR-H3 comprising the amino acid sequence of SEQ ID NO: 108.

In some embodiments, the antibody comprises: a) a heavy chain comprising a HVR-H1 comprising the amino acid sequence of SEQ ID NO:49, HVR-H2 comprising the amino acid sequence of SEQ ID NO:73, and HVR-H3 comprising the amino acid sequence of SEQ ID NO:97; and/or b) a light chain comprising a HVR-L1 comprising the amino acid sequence of SEQ ID NO: 13, HVR-L2 comprising the amino acid sequence of SEQ ID NO:25, and HVR-L3 comprising the amino acid sequence of SEQ ID NO:37. In some embodiments, the heavy chain comprising a HVR-H1 comprising the amino acid sequence of SEQ ID NO:61, HVR-H2 comprising the amino acid sequence of SEQ ID NO:85, and HVR-H3 comprising the amino acid sequence of SEQ ID NO: 109.

In some embodiments of any of the antibodies, the antibody comprises: a) a VH sequence having at least 95% sequence identity to the amino acid sequence of SEQ ID NO: 111 and/or a VL sequence having at least 95% sequence identity to the amino acid sequence of SEQ ID NO: 110; b) a VH sequence having at least 95% sequence identity to the amino acid sequence of SEQ ID NO: 113 and/or a VL sequence having at least 95% sequence identity to the amino acid sequence of SEQ ID NO: 112; c) a VH sequence having at least 95% sequence identity to the amino acid sequence of SEQ ID NO: 115 and/or a VL sequence having at least 95% sequence identity to the amino acid sequence of SEQ ID NO: 114; d) a VH sequence having at least 95% sequence identity to the amino acid sequence of SEQ ID NO: 117 and/or a VL sequence having at least 95% sequence identity to the amino acid sequence of SEQ ID NO: 116; e) a VH sequence having at least 95% sequence identity to the amino acid sequence of SEQ ID NO: 119 and/or a VL sequence having at least 95% sequence identity to the amino acid sequence of SEQ ID NO: 118; f) a VH sequence having at least 95% sequence identity to the amino acid sequence of SEQ ID NO: 121 and/or a VL sequence having at least 95% sequence identity to the amino acid sequence of SEQ ID NO: 120; g) a VH sequence having at least 95% sequence identity to the amino acid sequence of SEQ ID NO: 123 and/or a VL sequence having at least 95% sequence identity to the amino acid sequence of SEQ ID NO: 122; h) a VH sequence having at least 95% sequence identity to the amino acid sequence of SEQ ID NO: 125 and/or a VL sequence having at least 95% sequence identity to the amino acid sequence of SEQ ID NO: 124; i) a VH sequence having at least 95% sequence identity to the amino acid sequence of SEQ ID NO: 127 and/or a VL sequence having at least 95% sequence identity to the amino acid sequence of SEQ ID NO: 126; j) a VH sequence having at least 95% sequence identity to the amino acid sequence of SEQ ID NO: 129 and/or a VL sequence having at least 95% sequence identity to the amino acid sequence of SEQ ID NO: 128; k) a VH sequence having at least 95% sequence identity to the amino acid sequence of SEQ ID NO: 131 and/or a VL sequence having at least 95% sequence identity to the amino acid sequence of SEQ ID NO:130; l) a VH sequence having at least 95% sequence identity to the amino acid sequence of SEQ ID NO: 133 and/or a VL sequence having at least 95% sequence identity to the amino acid sequence of SEQ ID NO: 132; or a VH sequence having at least 95% sequence identity to the amino acid sequence of SEQ ID NO: 135 and/or a VL sequence having at least 95% sequence identity to the amino acid sequence of SEQ ID NO: 134.

In some embodiments of any of the antibodies, the antibody comprises: a) a VH sequence of SEQ ID NO: 111 and/or a VL sequence of SEQ ID NO:110; b) a VH sequence of SEQ ID NO: 113 and/or a VL sequence of SEQ ID NO: 112; c) a VH sequence of SEQ ID NO: 115 and/or a VL sequence of SEQ ID NO: 114; d) a VH sequence of SEQ ID NO: 117 and/or a VL sequence of SEQ ID NO: 116; e) a VH sequence of SEQ ID NO: 119 and/or a VL sequence of SEQ ID NO: 118; f) a VH sequence of SEQ ID NO: 121 and/or a VL sequence of SEQ ID NO: 120; g) a VH sequence of SEQ ID NO: 123 and/or a VL sequence of SEQ ID NO: 122; h) a VH sequence of SEQ ID NO: 125 and/or a VL sequence of SEQ ID NO: 124; i) a VH sequence of SEQ ID NO: 127 and/or a VL sequence of SEQ ID NO: 126; j) a VH sequence of SEQ ID NO: 129 and/or a VL sequence of SEQ ID NO: 128; k) a VH sequence of SEQ ID NO: 131 and/or a VL sequence of SEQ ID NO:130; l) a VH sequence of SEQ ID NO: 133 and/or a VL sequence of SEQ ID NO: 132, or m) a VH sequence of SEQ ID NO: 135 and/or a VL sequence of SEQ ID NO: 134.

In some embodiments of any of the antibodies, the antibody is a monoclonal antibody. In some embodiments of any of the antibodies, the antibody is a human, humanized, or chimeric antibody. In some embodiments of any of the antibodies, the antibody is an antibody fragment that binds FcRH5. In some embodiments of any of the antibodies, the antibody is an IgG1, IgG2a or IgG2b antibody.

In some embodiments of any of the antibodies, the antibody has one or more of the following characteristics: a) cross reactive with full length human and cyno FcRH5, b) does not cross react with FcRH1, FcRH2, FcRH3, and/or FcRH4, c) binds to endogenous FcRH5, d) does not cross react with FcRH5a, and e) does not cross react with another Ig-like domain of FcRH5.

In some embodiments of any of the antibodies, the antibody is a bispecific antibody. In some embodiments, the bispecific antibody binds FcRH5 and CD3.

In some embodiments, an isolated nucleic acid that encodes an antibody described herein is provided. In some embodiments, a host cell comprising the nucleic acid is provided. In some embodiments, a method of producing an antibody described herein is provided. In some embodiments, the method comprises culturing the host cell comprising the nucleic acid that encodes an antibody.

In some embodiments, immunoconjugates are provided. In some embodiments, an immunoconjugate comprises an anti-FcRH5 antibody and a cytotoxic agent. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, an immunoconjugate has the formula Ab-(L-D)p, wherein: (a) Ab is an antibody described herein; (b) L is a linker; (c) D is a drug selected from a maytansinoid, an auristatin, a calicheamicin, a pyrrolobenzodiazepine, and a nemorubicin derivative; and (d) p ranges from 1-8. In some embodiments, D is an auristatin. In some such embodiments, D has formula $D_E$ $D_E$

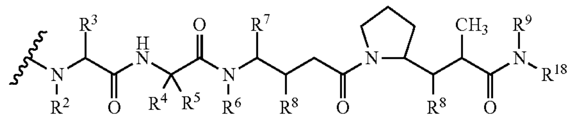

wherein $R^2$ and $R^6$ are each methyl, $R^3$ and $R^4$ are each isopropyl, $R^5$ is H, $R^7$ is sec-butyl, each $R^8$ is independently selected from $CH_3$, O—$CH_3$, OH, and H; $R^9$ is H; and $R^{18}$ is —$C(R^8)_2$—$C(R^8)_2$-aryl. In some embodiments, D is MMAE having the structure:

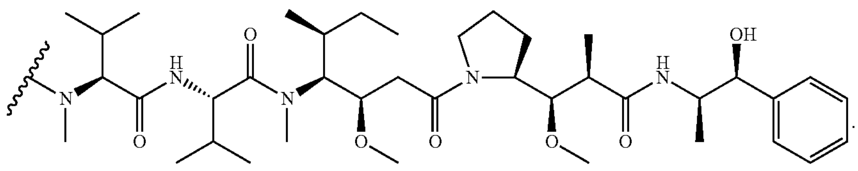 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

In some embodiments, D is a pyrrolobenzodiazepine of Formula A:

A

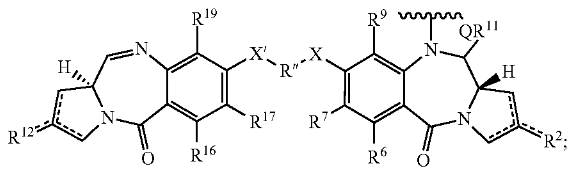

wherein the dotted lines indicate the optional presence of a double bond between C1 and C2 or C2 and C3; $R^2$ is independently selected from H, OH, =O, =$CH_2$, CN, R, OR, =CH—$R^D$, =$C(R^D)_2$, O—$SO_2$—R, $CO_2R$ and COR, and optionally further selected from halo or dihalo, wherein $R^D$ is independently selected from R, $CO_2R$, COR, CHO, $CO_2H$, and halo; $R^6$ and $R^9$ are independently selected from H, R, OH, OR, SH, SR, $NH_2$, NHR, NRR', $NO_2$, $Me_3Sn$ and halo; $R^7$ is independently selected from H, R, OH, OR, SH, SR, $NH_2$, NHR, NRR', $NO_2$, $Me_3Sn$ and halo; Q is independently selected from 0, S and NH; $R^{11}$ is either H, or R or, where Q is O, $SO_3M$, where M is a metal cation; R and R' are each independently selected from optionally substituted $C_{1-8}$ alkyl, $C_{1-12}$ alkyl, $C_{3-s}$ heterocyclyl, $C_{3-20}$ heterocyclyl, and $C_{5-20}$ aryl groups, and optionally in relation to the group NRR', R and R' together with the nitrogen atom to which they are attached form an optionally substituted 4-, 5-, 6- or 7-membered heterocyclic ring; $R^{12}$, $R^{16}$, $R^9$ and $R^{17}$ are as defined for $R^2$, $R^6$, $R^9$ and $R^7$ respectively; R" is a $C_{3-12}$ alkylene group, which chain may be interrupted by one or more heteroatoms and/or aromatic rings that are optionally substituted; and X and X' are independently selected from O, S and N(H). In some such embodiments, D is

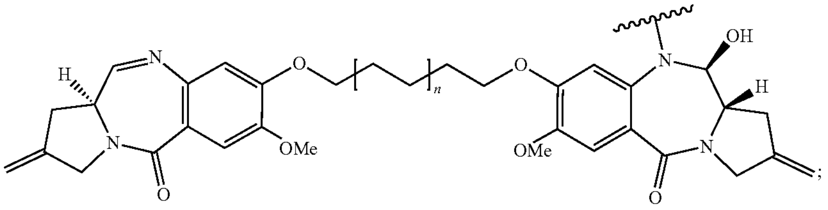

wherein n is 0 or 1.

In some embodiments, D is a nemorubicin derivative. In some embodiments, D has a structure selected from:

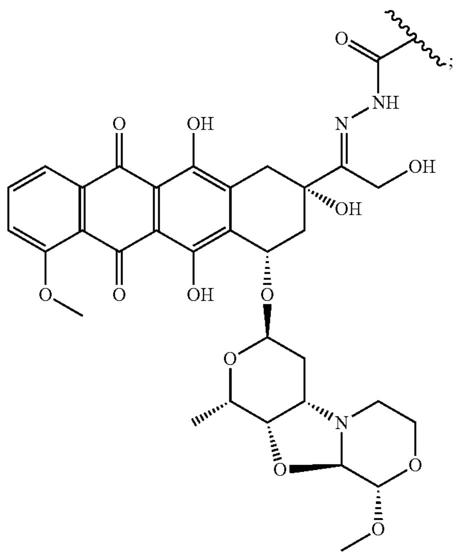

and

-continued

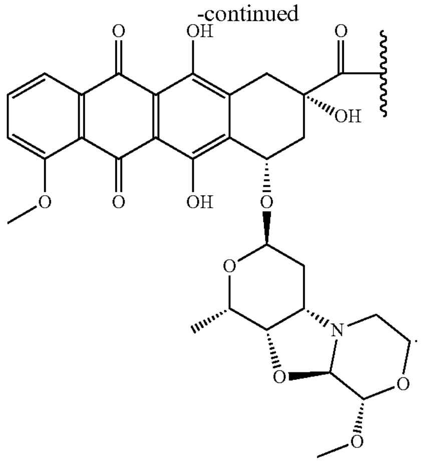

In some embodiments, an immunoconjugate comprises a linker that is cleavable by a protease. In some embodiments, the linker comprises a val-cit dipeptide or a Phe-homoLys dipeptide. In some embodiments, an immunoconjugate comprises a linker that is acid-labile. In some such embodiments, the linker comprises hydrazone.

In some embodiments, an immunoconjugate has a formula selected from:

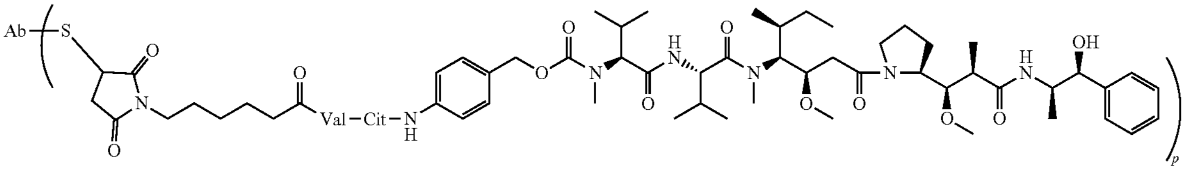

wherein S is a sulfur atom;

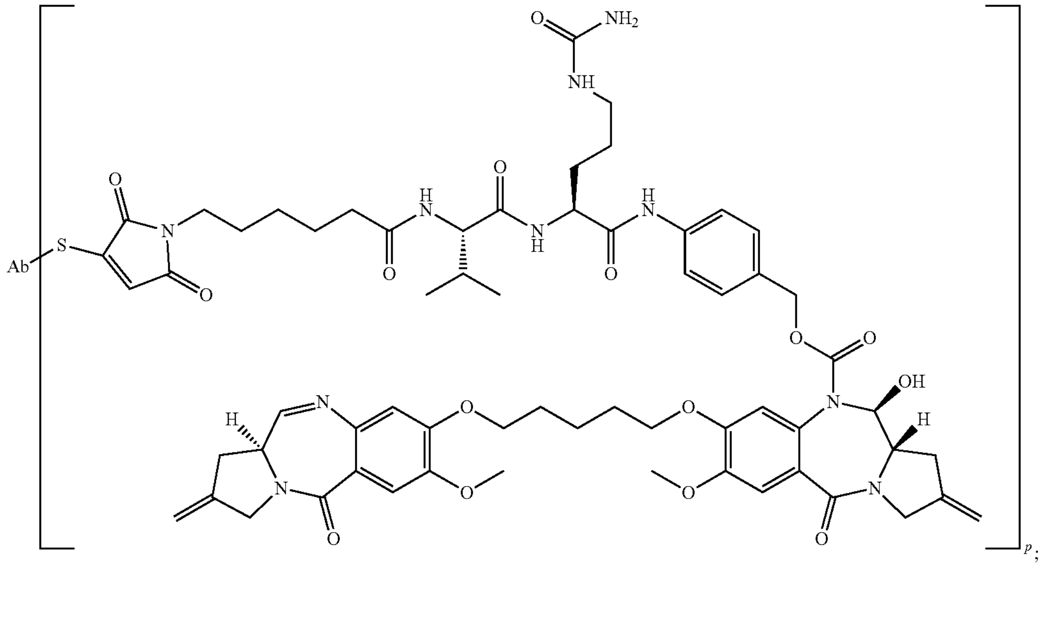

-continued
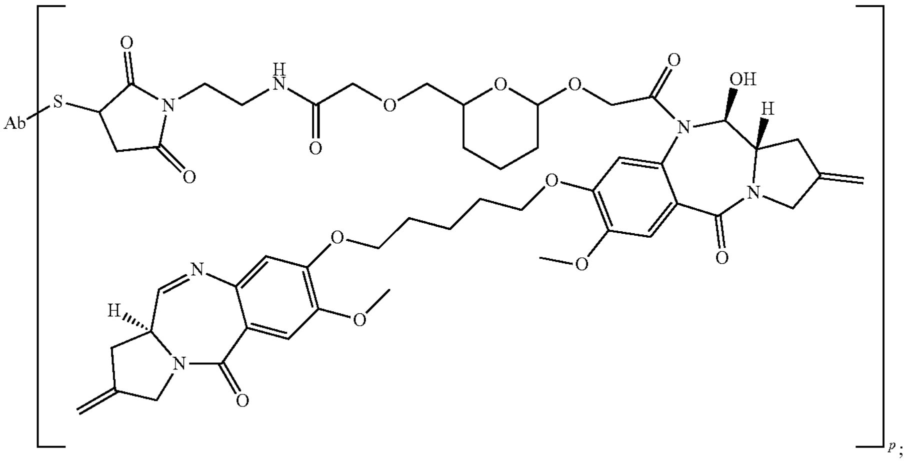
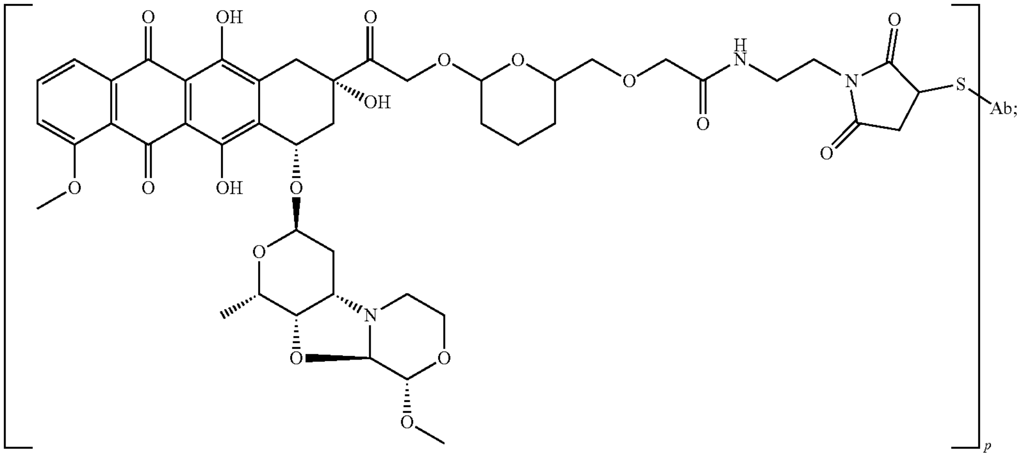
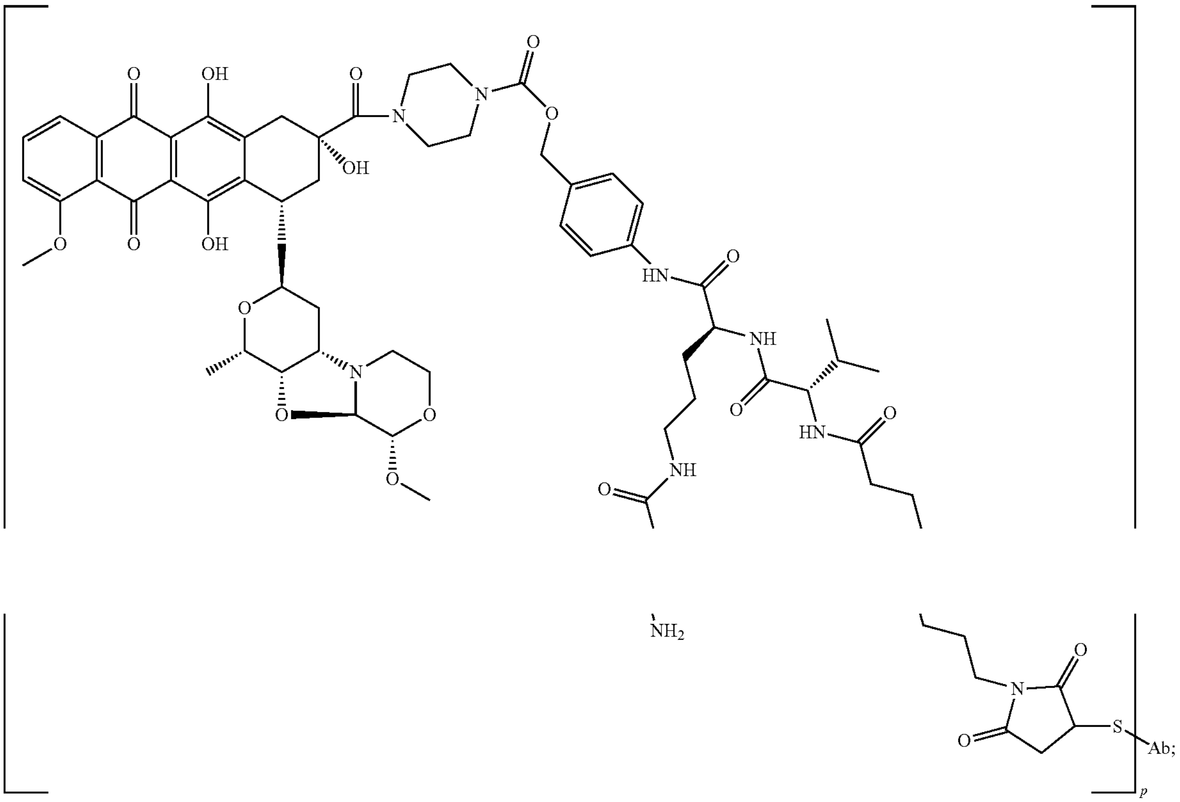

-continued
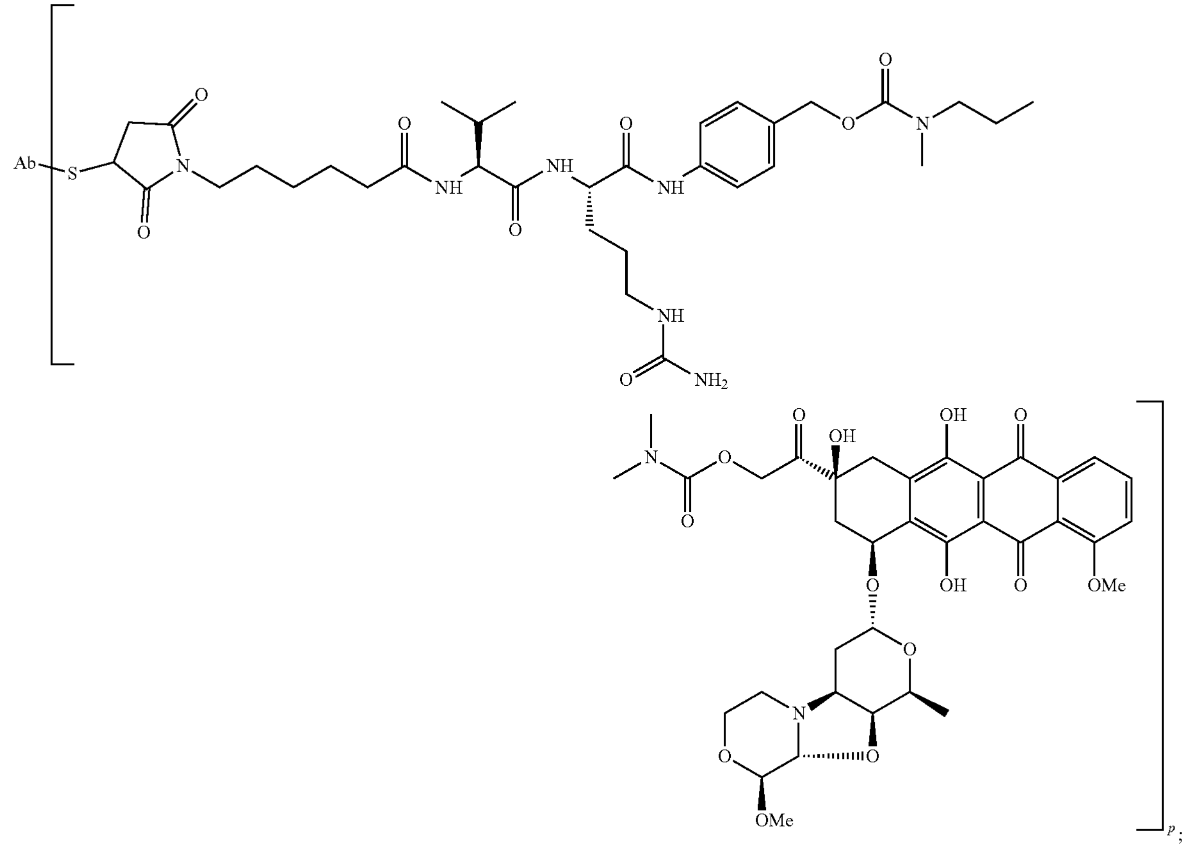
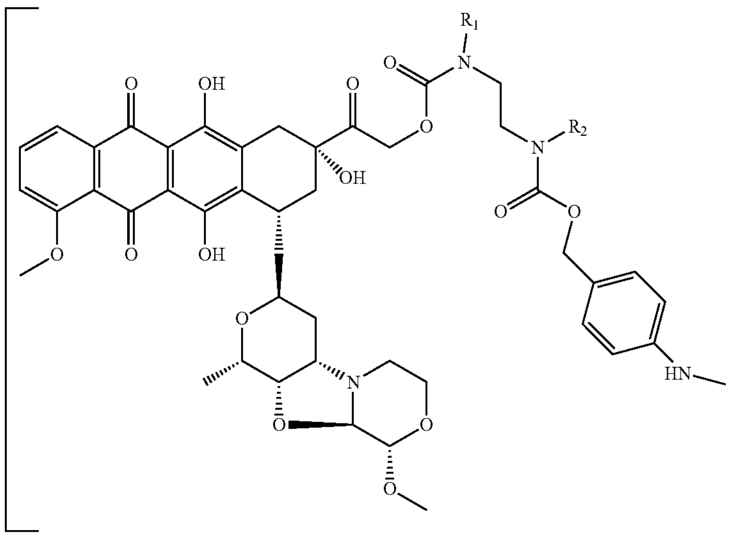

-continued
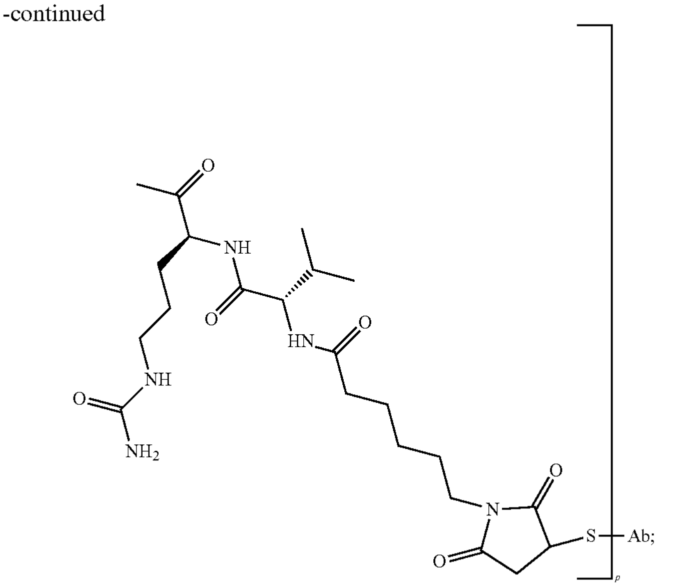
and
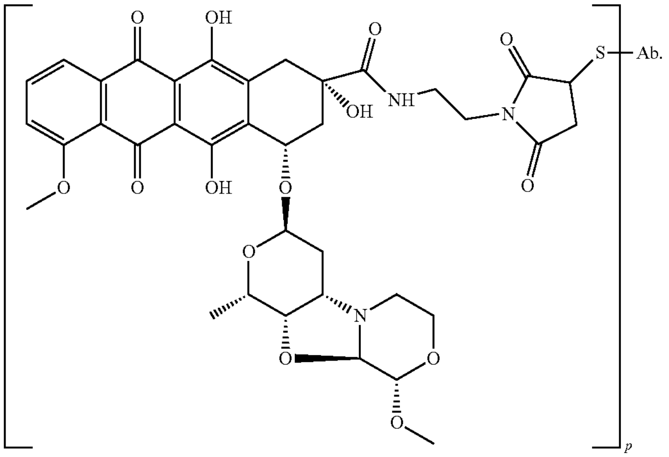
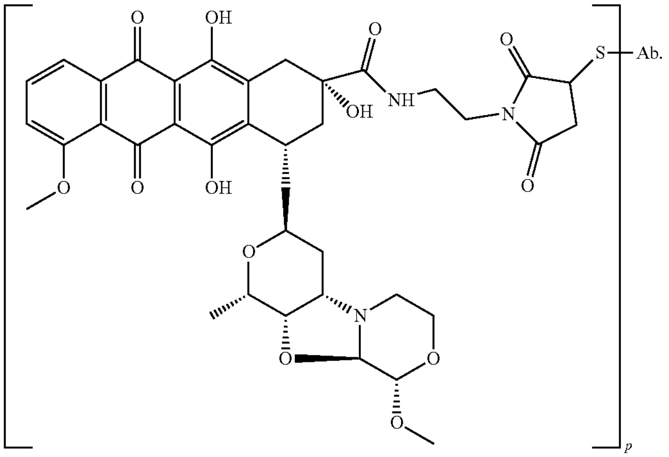

In some embodiments, p ranges from 2-5.

In some embodiments, pharmaceutical formulations are provided. In some such embodiments, a pharmaceutical formulation comprises an immunoconjugate comprising an antibody that binds FcRH5, e.g., as described herein. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, a pharmaceutical formulation further comprises an additional therapeutic agent.

In some embodiments, methods of treating individuals having FcRH5 (e.g., FcRH5c)-positive cancers are provided. In some such embodiments, a method comprises administering a pharmaceutical formulation comprising an immunoconjugate comprising an antibody that binds FcRH5 and/or an FcRH5 bispecific antibody, e.g., as described herein. In some embodiments, the FcRH5 bispecific antibody comprises an FcRH5 binding arm and a CD3 binding arm. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, the FcRH5-positive cancer is a B-cell proliferative disorder. In some embodiments, the FcRH5-positive cancer is plasma cell neoplasm. In some embodiments, the plasma cell neoplasm is multiple myeloma. In some embodiments, a method comprises administering an additional therapeutic agent to the individual.

In some embodiments, methods of inhibiting proliferation of an FcRH5 (e.g., FcRH5c)-positive cell are provided. In some embodiments, the method comprising exposing the cell to an immunoconjugate comprising an antibody that binds FcRH5 and/or an FcRH5 bispecific antibody under conditions permissive for binding of the antibody to FcRH5 on the surface of the cell. In some embodiments, the FcRH5 bispecific antibody comprises an FcRH5 binding arm and a CD3 binding arm. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, the antibody that binds FcRH5 is an antibody described herein. In some embodiments, the FcRH5-positive cancer is a B-cell proliferative disorder. In some embodiments, the FcRH5-positive cancer is plasma cell neoplasm. In some embodiments, the plasma cell neoplasm is multiple myeloma. In some embodiments, a method comprises administering an additional therapeutic agent to the individual.

In some embodiments, an antibody that binds FcRH5 is conjugated to a label. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, the antibody that binds FcRH5 is an antibody described herein. In some embodiments, the label is a positron emitter. In some embodiments, the positron emitter is $^{89}$Zr.

In some embodiments, a method of detecting human FcRH5 in a biological sample is provided. In some embodiments, a method comprises contacting the biological sample with an anti-FcRH5 antibody under conditions permissive for binding of the anti-FcRH5 antibody to a naturally occurring human FcRH5, and detecting whether a complex is formed between the anti-FcRH5 antibody and a naturally occurring human FcRH5 in the biological sample. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, the anti-FcRH5 antibody is an antibody described herein.

In some embodiments, a method for detecting an FcRH5-positive cancer is provided. In some such embodiments, a method comprises (i) administering a labeled anti-FcRH5 antibody to a subject having or suspected of having an FcRH5-positive cancer, and (ii) detecting the labeled anti-FcRH5 antibody in the subject, wherein detection of the labeled anti-FcRH5 antibody indicates an FcRH5-positive cancer in the subject. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In some embodiments, an anti-FcRH5 antibody is an antibody described herein.

BRIEF DESCRIPTION OF THE FIGURES

FIG. 1B depicts part of FcRH5 (SEQ ID NO: 136) and the structure and homology of FcRH5 amino acids 735 to 977 of FcRH5c (SEQ ID NO:2).

FIG. 10A shows the CDR L1 sequences for each of the 1C8.1, 1G7.2, 2H7.3, 3A4.2, 3B12.1.1, 3C10, 3F10, 3G3, 3G7.1.5, 5A10.1.3, 5F1.1.5, and 6D2 anti-FcRH5 antibody clones.

FIG. 10B shows the CDR L2 sequences for each of the 1C8.1, 1G7.2, 2H7.3, 3A4.2, 3B12.1.1, 3C10, 3F10, 3G3, 3G7.1.5, 5A10.1.3, 5F1.1.5, and 6D2 anti-FcRH5 antibody clones.

FIG. 10C shows the CDR L3 sequences for each of the 1C8.1, 1G7.2, 2H7.3, 3A4.2, 3B12.1.1, 3C10, 3F10, 3G3, 3G7.1.5, 5A10.1.3, 5F1.1.5, and 6D2 anti-FcRH5 antibody clones.

FIG. 11A shows the CDRH1 sequences for each of the 1C8.1, 1G7.2, 2H7.3, 3A4.2, 3B12.1.1, 3C10, 3F10, 3G3, 3G7.1.5, 5A10.1.3, 5F1.1.5, and 6D2 anti-FcRH5 antibody clones.

FIG. 11B shows the CDR H2 sequences for each of the 1C8.1, 1G7.2, 2H7.3, 3A4.2, 3B12.1.1, 3C10, 3F10, 3G3, 3G7.1.5, 5A10.1.3, 5F1.1.5, and 6D2 anti-FcRH5 antibody clones.

FIG. 11C shows the CDRH3 sequences for each of the 1C8.1, 1G7.2, 2H7.3, 3A4.2, 3B12.1.1, 3C10, 3F10, 3G3, 3G7.1.5, 5A10.1.3, 5F1.1.5, and 6D2 anti-FcRH5 antibody clones.

DETAILED DESCRIPTION

I. Definitions

Figure 1A:
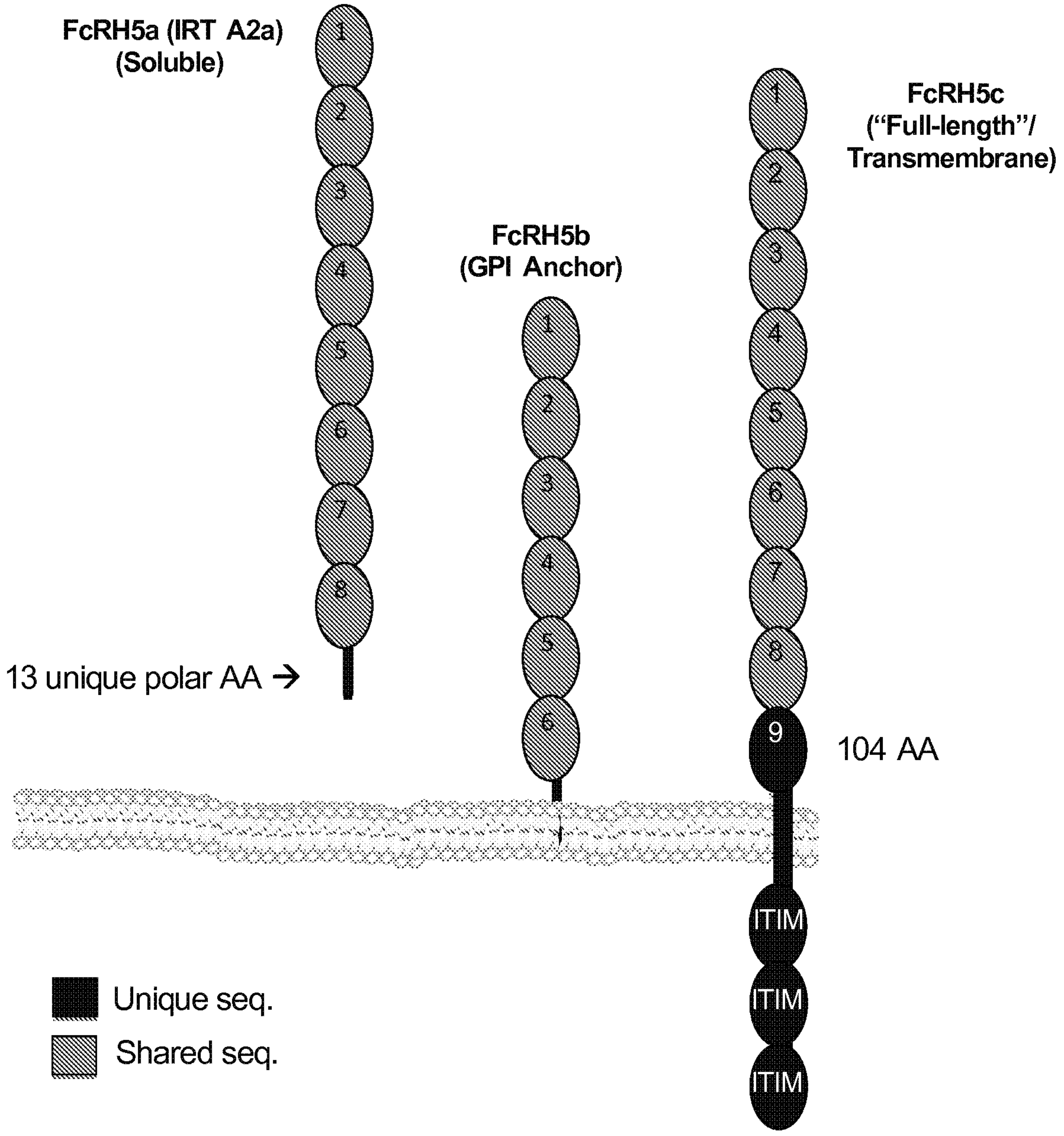
FIG. 1A depicts the three major isoforms of FcRH5, FcRH5a (IRTA2a; UniProt Identifier Q96RD9-3), FcRH5b (IRTA2b; UniProt Identifier Q96RD9-4), and FcRH5c (IRTA2c; UniProt Identifier Q96RD9-1). The Ig-like domains are numbered and correspond to the amino acid sequence of UniProt Identifier Q69RD9-1 (SEQ ID NO: 1): Ig-like domain 1 (aa ("amino acid") 23-100), Ig-like domain 2 (aa 105-185), Ig-like domain 3 (aa 188-271), Ig-like domain 4 (287-373), Ig-like domain 5 (aa 380-466), Ig-like domain 6 (aa 490-555), Ig-like domain 7 (aa 568-652), Ig-like domain 8 (aa 658-731), and Ig-like domain 9 (aa 754-835).

The term "FcRH5," as used herein, refers to any native, mature FcRH5 which results from processing of an FcRH5 precursor protein in a cell. The term includes FcRH5 from any vertebrate source, including mammals such as primates (e.g. humans and cynomolgus monkeys) and rodents (e.g., mice and rats), unless otherwise indicated. The term also includes naturally occurring variants of FcRH5, e.g., splice variants or allelic variants. In some embodiments, the amino acid sequences human FcRH5 proteins is FcRH5a (IRTA2a; UniProt Identifier Q96RD9-3; 759 aa), FcRH5b (IRTA2b; UniProt Identifier Q96RD9-4; 592 aa), FcRH5c (IRTA2c; UniProt Identifier Q96RD9-1; 977 aa (SEQ ID NO: 1), UniProt Identifier Q96RD9-2 (124 aa), and/or FcRH5d (IRTA2d; UniProt Identifier Q96RD9-5; 152 aa).

The term "glycosylated forms of FcRH5" refers to naturally occurring forms of FcRH5 that are post-translationally modified by the addition of carbohydrate residues.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "anti-FcRH5 antibody" and "an antibody that binds to FcRH5" refer to an antibody that is capable of binding FcRH5 with sufficient affinity such that the antibody is useful as a diagnostic and/or therapeutic agent in targeting FcRH5. In one embodiment, the extent of binding of an anti-FcRH5 antibody to an unrelated, non-FcRH5 protein is less than about 10% of the binding of the antibody to FcRH5 as measured, e.g., by a radioimmunoassay (RIA). In certain embodiments, an antibody that binds to FcRH5 has a dissociation constant (Kd) of ≤1 μM, ≤100 nM, ≤10 nM, ≤5 Nm, ≤4 nM, ≤3 nM, ≤2 nM, ≤1 nM, 0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-FcRH5 antibody binds to an epitope of FcRH5 that is conserved among FcRH5 from different species. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g., scFv); and multispecific antibodies formed from antibody fragments.

The term "epitope" refers to the particular site on an antigen molecule to which an antibody binds.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The terms "full length antibody," "intact antibody," and "whole antibody" are used herein interchangeably to refer to an antibody having a structure substantially similar to a native antibody structure or having heavy chains that contain an Fc region as defined herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology,* $6^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991) .) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof, and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B-cell receptor); and B-cell activation.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-FcRH5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies provided herein are used to delay development of a disease or to slow the progression of a disease.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, small intestine cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

A "B-cell malignancy" herein includes non-Hodgkin's lymphoma (NHL), including low grade/follicular NHL, small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia, non-Hodgkin's lymphoma (NHL), lymphocyte predominant Hodgkin's disease (LPHD), small lymphocytic lymphoma (SLL), chronic lymphocytic leukemia (CLL), indolent NHL including relapsed indolent NHL and rituximab-refractory indolent NHL; leukemia, including acute lymphoblastic leukemia (ALL), chronic lymphocytic leukemia (CLL), Hairy cell leukemia, chronic myeloblastic leukemia; mantle cell lymphoma; and other hematologic malignancies. Such malignancies may be treated with antibodies directed against B-cell surface markers, such as FcRH5 (e.g., FcRH5c). Such diseases are contemplated herein to be treated by the administration of an antibody directed against a B-cell surface marker, such as FcRH5 (e.g., FcRH5c), and includes the administration of an unconjugated ("naked") antibody or an antibody conjugated to a cytotoxic agent as disclosed herein. Such diseases are also contemplated herein to be treated by combination therapy including an anti-FcRH5 antibody (including FcRH5 bispecific antibody) or anti-FcRH5 antibody drug conjugate in combination with another antibody or antibody drug conjugate, another cytotoxic agent, radiation or other treatment administered simultaneously or in series.

The term "non-Hodgkin's lymphoma" or "NHL", as used herein, refers to a cancer of the lymphatic system other than Hodgkin's lymphomas. Hodgkin's lymphomas can generally be distinguished from non-Hodgkin's lymphomas by the presence of Reed-Sternberg cells in Hodgkin's lymphomas and the absence of said cells in non-Hodgkin's lymphomas. Examples of non-Hodgkin's lymphomas encompassed by the term as used herein include any that would be identified as such by one skilled in the art (e.g., an oncologist or pathologist) in accordance with classification schemes known in the art, such as the Revised European-American Lymphoma (REAL) scheme as described in Color Atlas of Clinical Hematology (3rd edition), A. Victor Hoffbrand and John E. Pettit (eds.) (Harcourt Publishers Ltd., 2000). See, in particular, the lists in FIGS. 11.57, 11.58 and 11.59. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone—MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

Plasma cells disorders result from the uncontrolled division or multiplication of a plasma cell clone. Plasma cells arise from activated B lymphocytes (i.e., B-cells). Each B-cell produces a unique receptor, known as the B-cell receptor, arrayed on its cell surface that is specific for a foreign substance, i.e., antigen. When a B-cell receptor binds its cognate antigen, the cell expressing the receptor is activated to re-enter the cell cycle, producing many clonal copies of itself. The clones mature into plasma cells that reside principally in the bone marrow and that are specialized to produce copies of the B-cell receptor that are released into the blood stream as antibodies. In a plasma cell disorder, the plasma cell or the parent B-cell suffers genetic damage resulting in suppression of or insensitivity to the normal restraints on cell division and/or activity. Daughter plasma cells derived from such cells are malignant in that they may divide unchecked and/or generate excess amount of the same immunoglobulin (antibody). Often the immunoglobulin produced is incomplete or has an incorrect conformation that can result in accumulation of the protein (also known as monoclonal protein, M protein, paraprotein or amyloid protein, dependent on the specific disorder) in the serum, tissues or organs (especially the kidneys), leading to organ dysfunction and/or failure. Plasma cell disorders include monoclonal gammopathies of undetermined significance (MGUS), multiple myeloma (MM), macroglobulinemia, heavy chain diseases, and systemic light-chain amyloidosis (AL), which are differentiated based on the proliferative nature of the clone, the extent of marrow involvement, and the type of M protein expressed. Additional plasma cell disorders are solitary plasmacytoma, extramedullary plasmacytoma, multiple solitary plasmacytomas, plasma cell leukemia, Waldenstrom's macroglobulinaemia, B-cell non-Hodgkin lymphomas, B-cell chronic lymphocytic leukemia.

The term "FcRH5-positive cancer" refers to a cancer comprising cells that express FcRH5 on their surface. For the purposes of determining whether a cell expresses FcRH5 on the surface, FcRH5 mRNA expression is considered to correlate to FcRH5 expression on the cell surface. In some embodiments, expression of FcRH5 mRNA is determined by a method selected from in situ hybridization and RT-PCR (including quantitative RT-PCR). Alternatively, expression of FcRH5 on the cell surface can be determined, for example, using antibodies to FcRH5 in a method such as immunohistochemistry, FACS, etc. In some embodiments, FcRH5 is one or more of FcRH5a, FcRH5b, FcRH5c, UniProt Identifier Q96RD9-2, and/or FcRH5d. In some embodiments, the FcRH5 is FcRH5c.

The term "FcRH5-positive cell" refers to a cell that expresses FcRH5 on its surface. In some embodiments, FcRH5 is one or more of FcRH5a, FcRH5b, FcRH5c, UniProt Identifier Q96RD9-2, and/or FcRH5d. In some embodiments, the FcRH5 is FcRH5c.

An "effective amount" of an agent, e.g., a pharmaceutical formulation, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

"Alkyl" is $C_1$-$C_{18}$ hydrocarbon containing normal, secondary, tertiary or cyclic carbon atoms. Examples are methyl (Me, $-CH_3$), ethyl (Et, $-CH_2CH_3$), 1-propyl (n-Pr, n-propyl, $-CH_2CH_2CH_3$), 2-propyl (i-Pr, i-propyl, $-CH(CH_3)_2$), 1-butyl (n-Bu, n-butyl, $-CH_2CH_2CH_2CH_3$), 2-methyl-1-propyl (i-Bu, i-butyl, $-CH_2CH(CH_3)_2$), 2-butyl (s-Bu, s-butyl, $-CH(CH_3)CH_2CH_3$), 2-methyl-2-propyl (t-Bu, t-butyl, $-C(CH_3)_3$), 1-pentyl (n-pentyl, $-CH_2CH_2CH_2CH_2CH_3$), 2-pentyl ($-CH(CH_3)CH_2CH_2CH_3$), 3-pentyl ($-CH(CH_2CH_3)_2$), 2-methyl-2-butyl ($-C(CH_3)_2CH_2CH_3$), 3-methyl-2-butyl ($-CH(CH_3)CH(CH_3)_2$), 3-methyl-1-butyl ($-CH_2CH_2CH(CH_3)_2$), 2-methyl-1-butyl ($-CH_2CH(CH_3)CH_2CH_3$), 1-hexyl ($-CH_2CH_2CH_2CH_2CH_2CH_3$), 2-hexyl ($-CH(CH_3)CH_2CH_2CH_2CH_3$), 3-hexyl ($-CH(CH_2CH_3)(CH_2CH_2CH_3)$), 2-methyl-2-pentyl ($-C(CH_3)_2CH_2CH_2CH_3$), 3-methyl-2-pentyl ($-CH(CH_3)CH(CH_3)CH_2CH_3$), 4-methyl-2-pentyl ($-CH(CH_3)CH_2CH(CH_3)_2$), 3-methyl-3-pentyl ($-C(CH_3)(CH_2CH_3)_2$), 2-methyl-3-pentyl ($-CH(CH_2CH_3)CH(CH_3)_2$), 2,3-dimethyl-2-butyl ($-C(CH_3)_2CH(CH_3)_2$), 3,3-dimethyl-2-butyl ($-CH(CH_3)C(CH_3)_3$. The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-NHC(O)R'$, $-SO_3R'$, $-S(O)_2R'$, $-S(O)R'$, $-OH$, -halogen, $-N_3$, $-NH_2$, $-NH(R')$, $-N(R')_2$ and $-CN$; where each R' is independently selected from H, $-C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, $-C_1$-$C_8$ alkyl, $-O-(C_1$-$C_8$ alkyl), -aryl, $-C(O)R'$, $-OC(O)R'$, $-C(O)OR'$, $-C(O)NH_2$, $-C(O)NHR'$, $-C(O)N(R')_2-NHC(O)R'$, $-SO_3R'$, $-S(O)_2R'$, $-S(O)R'$, $-OH$, -halogen, $-N_3$, $-NH_2$, $-NH(R')$, $-N(R')_2$ and $-CN$; where each R' is independently selected from H, $-C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy ($—OCH_3$) and ethoxy ($—OCH_2CH_3$). A "$C_1$-$C_8$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl ($—CH{=}CH_2$), allyl ($—CH_2CH{=}CH_2$), cyclopentenyl ($—C_5H_7$), and 5-hexenyl ($—CH_2CH_2CH_2CH_2CH{=}CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic ($—C{=}CH$) and propargyl ($—CH_2C{\equiv}CH$). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene ($—CH_2—$) 1,2-ethyl ($—CH_2CH_2—$), 1,3-propyl ($—CH_2CH_2CH_2—$), 1,4-butyl ($—CH_2CH_2CH_2CH_2—$), and the like.

A "$C_1$-$C_{10}$ alkylene" is a straight chain, saturated hydrocarbon group of the formula $—(CH_2)_{1\text{-}10}—$. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene ($—CH{=}CH—$).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene ($—C{\equiv}C—$), propargyl ($—CH_2C{\equiv}C—$), and 4-pentynyl ($—CH_2CH_2CH_2C{=}C—$).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, $—C_1$-$C_8$ alkyl, $—O—(C_1$-$C_8$ alkyl), -aryl, —C(O)R', —OC(O)R', —C(O)OR', $—C(O)NH_2$, —C(O)NHR', $—C(O)N(R')_2$—NHC(O)R', $—S(O)_2R'$, —S(O)R', —OH, -halogen, $—N_3$, $—NH_2$, —NH(R'), $—N(R')_2$ and —CN; wherein each R' is independently selected from H, $—C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

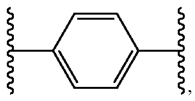
,
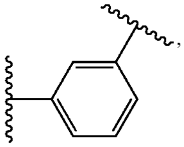
,
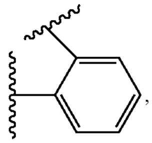
, in which the phenyl group can be unsubstituted or substituted with up to four groups including, but not limited to, $—C_1$-$C_8$ alkyl, $—O—(C_1$-$C_8$ alkyl), -aryl, —C(O)R', —OC(O)R', —C(O)OR', $—C(O)NH_2$, —C(O)NHR', $—C(O)N(R')_2$—NHC(O)R', $—S(O)_2R'$, —S(O)R', —OH, -halogen, $—N_3$, $—NH_2$, —NH(R'), $—N(R')_2$ and —CN; wherein each R' is independently selected from H, $—C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O—, —OR, —SR, —S—, —$NR_2$, —$NR_3$, =NR, —$CX_3$, —CN, —OCN, —SCN, —N=C=O, —NCS, —NO, —$NO_2$, =$N_2$, —$N_3$, NC(=O)R, —C(=O)R, —C(=O)$NR_2$, —$SO_3^-$, —$SO_3H$, —S(=O)$_2$R, —OS(=O)$_2$OR, —S(=O)$_2$NR, —S(=O)R, —OP(=O)(OR)$_2$, —P(=O)(OR)$_2$, —$PO_3$, —PO3H2, —C(=O)R, —C(=O)X, —C(=S)R, —$CO_2$R, —$CO_2$, —C(=S)OR, —C(=O)SR, —C(=S)SR, —C(=O)$NR_2$, —C(=S)$NR_2$, —C(=NR)$NR_2$, where each X is independently a halogen: F, Cl, Br, or I; and each R is independently —H, $C_2$-$C_{18}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modem Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH (R'), —N(R')$_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —$C(O)NH_2$, —C(O)NHR', —$C(O)N(R')_2$—NHC(O)R', —$S(O)_2R'$, —S(O)R', —OH, -halogen, —$N_3$, —$NH_2$, —NH(R'), —$N(R')_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-*Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and 1 or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

As is understood by one skilled in the art, reference to "about" a value or parameter herein includes (and describes) embodiments that are directed to that value or parameter per se. For example, description referring to "about X" includes description of "X".

It is understood that aspect and embodiments described herein include "consisting" and/or "consisting essentially of" aspects and embodiments. As used herein, the singular form "a", "an", and "the" includes plural references unless indicated otherwise.

II. Compositions and Methods

Provided herein are antibodies that bind to FcRH5 including bispecific antibodies and immunoconjugates comprising such antibodies. Antibodies and immunoconjugates may be useful, e.g., for the diagnosis or treatment of FcRH5-positive cancers. In some embodiments, the anti-FcRH5 antibody binds an isoform c-specific region of the extracellular domain of FcRH5c. In some embodiments, the anti-FcRH5 antibodies bind Ig-like domain 9 of FcRH5c.

Without being bound by theory, the selection of the precise antigen for the antibodies of the present invention was driven by at least three important considerations. First, there was a need for little to no cross-reactivity with FcRH5 isoforms other than FcRH5c, such as isoform a and isoform b, to avoid the resulting therapeutic from binding to non-target molecules and thus reducing its effectiveness. As illustrated in FIG. 1, domain 9 of FcRH5 is an example of a unique sequence among the three isoforms. Next, there was a need for little to no cross-reactivity with FcRH family members other than FcRH5, such as FcRH1, FcRH2, FcRH3, and FcRH4. This is difficult because of the generally highly conserved nature of the last Ig-like domains in many of the FcRH family members. But because of the parallel need for FcRH5 isoform c specificity, an antibody that binds the last Ig-like domain was pursued. Finally, for antibodies to be used in therapeutic molecules that work to bring large structures in close proximity, such as T-cells and tumor cells using a bispecific antibody format, it is known that tumor epitopes closer to the cell membrane are more effective (see, e.g., Bluemel et al. *Cancer Immunol Immunother*. (2010) 59:1197-1209). Sometimes described as the theory of kinetic segregation, the cell membrane proximal location of domain 9 of FcRH5 is a desirable antigen target in this context. To meet these considerations and as described in detail below, certain embodiments of the antibodies of the present invention were developed.

Provided herein are isolated anti-FcRH5 antibodies that binds an isoform c-specific region of the extracellular domain of FcRH5c. In some embodiments, the isoform c-specific region comprises Ig-like domain 9. In some embodiments, the Ig-like domain 9 is also called Ig-like C2-type 8. In some embodiments, the isoform c-specific region comprises amino acids 754-835 of SEQ ID NO: 1. In some embodiments, the isoform c-specific region comprises amino acids 752-834 of SEQ ID NO: 1. In some embodiments, the isoform c-specific region comprises amino acids 743-850 of SEQ ID NO: 1. In some embodiments, the isoform c-specific region comprises amino acids 745-851 of SEQ ID NO: 1. In some embodiments, the isoform c-specific region comprises amino acids about any of 1, 2, 3, 4, 5, 6, 7, 8, 9, 10, 11, 12, 13, 14, or 15 from the N-terminal and/or C-terminal boundary. In some embodiments, the isoform c-specific region comprises amino acids from about any of 750, 751, 752, 753, or 754 to about any of 830, 831, 832, 833, 834, 835, or 836 of SEQ ID NO: 1. In some embodiments, the antibodies binds FcRH5c and/or the isoform c-specific region with an affinity of ≤5 nM, or ≤4 nM, or ≤3 nM, or ≤2 nM, or ≤1 nM, and optionally ≥0.0001 nM, or ≥0.001 nM, or ≥0.01 nM.

In some embodiments of any of the antibodies, the antibody has one or more of the following characteristics: a) cross reactive with full length human and cyno FcRH5 (i.e., binds full length human FcRH5 and binds full length cyno FcRH5), b) does not significantly cross react with FcRH1, FcRH2, FcRH3, and/or FcRH4 (i.e., does not significantly bind FcRH1, FcRH2, FcRH3, and/or FcRH4), c) binds to endogenous FcRH5, d) does not cross react with FcRH5a (i.e., does not significantly bind FcRH5a), and e) does not cross react with another Ig-like domain of FcRH5 (i.e., does not significantly bind another Ig-like domain of FcRH5). Methods of determining the ability to bind are known in the art and described below.

Provided herein, and in some embodiments, are antibodies comprising a) a heavy chain comprising a HVR-H1 comprising the amino acid sequence of SEQ ID NO:38, HVR-H2 comprising the amino acid sequence of SEQ ID NO:62, and HVR-H3 comprising the amino acid sequence of SEQ ID NO:86; and/or b) a light chain comprising a HVR-L1 comprising the amino acid sequence of SEQ ID NO:2, HVR-L2 comprising the amino acid sequence of SEQ ID NO: 14, and HVR-L3 comprising the amino acid sequence of SEQ ID NO:26. In some embodiments, the heavy chain comprising a HVR-H1 comprising the amino acid sequence of SEQ ID NO:50, HVR-H2 comprising the amino acid sequence of SEQ ID NO:74, and HVR-H3 comprising the amino acid sequence of SEQ ID NO:98. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 111 and/or a VL sequence having at least about any of 90%, 91%, 92%, 93%, 94%, 95%, 96%, 97%, 98%, 99%, or 100% sequence identity to the amino acid sequence of SEQ ID NO: 110. In some embodiments, the antibody comprises a VH sequence of SEQ ID NO: 111 and/or a VL sequence of SEQ ID NO:110. In some embodiments of any of the antibodies, the antibody comprises six HVRs of 1C8.1. In some embodiments, the antibody comprises VH domain and VL domain of 1C8.1. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes.

Provided herein, and in some embodiments, are antibodies comprising a) a heavy chain comprising a HVR-H1 comprising the amino acid sequence of SEQ ID NO:39, HVR-H2 comprising the amino acid sequence of SEQ ID NO:63, and HVR-H3 comprising the amino acid sequence of SEQ ID NO:87; and/or b) a light chain comprising a HVR-L1 comprising the amino acid sequence of SEQ ID NO:3, HVR-L2 comprising the amino acid sequence of SEQ ID NO: 15, and HVR-L3 comprising the amino acid sequence of SEQ ID NO:27. In some embodiments, the heavy chain comprising a HVR-H1 comprising the amino acid sequence of SEQ ID NO:51, HVR-H2 comprising the amino acid sequence of SEQ ID NO:75, and HVR-H3 comprising the amino acid sequence of SEQ ID NO:99. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 113 and/or a VL sequence having at least about any of 90%, 91%, 92%, 93%, 94%, 95%, 96%, 97%, 98%, 99%, or 100% sequence identity to the amino acid sequence of SEQ ID NO: 112. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO:135 and/or a VL sequence having at least about any of 90%, 91%, 92%, 93%, 94%, 95%, 96%, 97%, 98%, 99%, or 100% sequence identity to the amino acid sequence of SEQ ID NO: 134. In some embodiments, the antibody comprises a VH sequence of SEQ ID NO: 113 and/or a VL sequence of SEQ ID NO: 112. In some embodiments, the antibody comprises a VH sequence of SEQ ID NO: 135 and/or a VL sequence of SEQ ID NO: 134. In some embodiments of any of the antibodies, the antibody comprises six HVRs of 1G7.2. In some embodiments, the antibody comprises VH domain and VL domain of 1G7.2. In some embodiments of any of the antibodies, the antibody comprises six HVRs of 1G7.2'. In some embodiments, the antibody comprises VH domain and VL domain of 1G7.2'. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes. In some embodiments, the antibody does not significantly cross react with FcRH5a.

Provided herein, and in some embodiments, are antibodies comprising a) a heavy chain comprising a HVR-H1 comprising the amino acid sequence of SEQ ID NO:40, HVR-H2 comprising the amino acid sequence of SEQ ID NO:64, and HVR-H3 comprising the amino acid sequence of SEQ ID NO:88; and/or b) a light chain comprising a HVR-L1 comprising the amino acid sequence of SEQ ID NO:4, HVR-L2 comprising the amino acid sequence of SEQ ID NO: 16, and HVR-L3 comprising the amino acid sequence of SEQ ID NO:28. In some embodiments, the heavy chain comprising a HVR-H1 comprising the amino acid sequence of SEQ ID NO:52, HVR-H2 comprising the amino acid sequence of SEQ ID NO:76, and HVR-H3 comprising the amino acid sequence of SEQ ID NO: 100. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 115 and/or a VL sequence having at least about any of 90%, 91%, 92%, 93%, 94%, 95%, 96%, 97%, 98%, 99%, or 100% sequence identity to the amino acid sequence of SEQ ID NO: 114. In some embodiments, the antibody comprises a VH sequence of SEQ ID NO: 115 and/or a VL sequence of SEQ ID NO: 114. In some embodiments of any of the antibodies, the antibody comprises six HVRs of 2H7.3. In some embodiments, the antibody comprises VH domain and VL domain of 2H7.3. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH3, and/or FcRH4. In some embodiments, the antibody binds to endogenous FcRH5. In some embodiments, the antibody binds B-cells. In some embodiments, the antibody does not significantly bind NK cells and/or monocytes.

Provided herein, and in some embodiments, are antibodies comprising a) a heavy chain comprising a HVR-H1 comprising the amino acid sequence of SEQ ID NO:41, HVR-H2 comprising the amino acid sequence of SEQ ID NO:65, and HVR-H3 comprising the amino acid sequence of SEQ ID NO:89; and/or b) a light chain comprising a HVR-L1 comprising the amino acid sequence of SEQ ID NO:5, HVR-L2 comprising the amino acid sequence of SEQ ID NO: 17, and HVR-L3 comprising the amino acid sequence of SEQ ID NO:29. In some embodiments, the heavy chain comprising a HVR-H1 comprising the amino acid sequence of SEQ ID NO:53, HVR-H2 comprising the amino acid sequence of SEQ ID NO:77, and HVR-H3 comprising the amino acid sequence of SEQ ID NO: 101. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 117 and/or a VL sequence having at least about any of 90%, 91%, 92%, 93%, 94%, 95%, 96%, 97%, 98%, 99%, or 100% sequence identity to the amino acid sequence of SEQ ID NO: 116. In some embodiments, the antibody comprises a VH sequence of SEQ ID NO: 117 and/or a VL sequence of SEQ ID NO: 116. In some embodiments of any of the antibodies, the antibody comprises six HVRs of 3A4.2. In some embodiments, the antibody comprises VH domain and VL domain of 3A4.2. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes.

Provided herein, and in some embodiments, are antibodies comprising a) a heavy chain comprising a HVR-H1 comprising the amino acid sequence of SEQ ID NO:42, HVR-H2 comprising the amino acid sequence of SEQ ID NO:66, and HVR-H3 comprising the amino acid sequence of SEQ ID NO:90; and/or b) a light chain comprising a HVR-L1 comprising the amino acid sequence of SEQ ID NO:6, HVR-L2 comprising the amino acid sequence of SEQ ID NO: 18, and HVR-L3 comprising the amino acid sequence of SEQ ID NO:30. In some embodiments, the heavy chain comprising a HVR-H1 comprising the amino acid sequence of SEQ ID NO:54, HVR-H2 comprising the amino acid sequence of SEQ ID NO:78, and HVR-H3 comprising the amino acid sequence of SEQ ID NO: 102. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 119 and/or a VL sequence having at least about any of 90%, 91%, 92%, 93%, 94%, 95%, 96%, 97%, 98%, 99%, or 100% sequence identity to the amino acid sequence of SEQ ID NO: 118. In some embodiments, the antibody comprises a VH sequence of SEQ ID NO: 119 and/or a VL sequence of SEQ ID NO: 118. In some embodiments of any of the antibodies, the antibody comprises six HVRs of 3B12.1.1. In some embodiments, the antibody comprises VH domain and VL domain of 3B12.1.1. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes. In some embodiments, the antibody does not significantly cross react with FcRH5a.

Provided herein, and in some embodiments, are antibodies comprising a) a heavy chain comprising a HVR-H1 comprising the amino acid sequence of SEQ ID NO:43, HVR-H2 comprising the amino acid sequence of SEQ ID NO:67, and HVR-H3 comprising the amino acid sequence of SEQ ID NO:91; and/or b) a light chain comprising a HVR-L1 comprising the amino acid sequence of SEQ ID NO:7, HVR-L2 comprising the amino acid sequence of SEQ ID NO: 19, and HVR-L3 comprising the amino acid sequence of SEQ ID NO:31. In some embodiments, the heavy chain comprising a HVR-H1 comprising the amino acid sequence of SEQ ID NO:55, HVR-H2 comprising the amino acid sequence of SEQ ID NO:79, and HVR-H3 comprising the amino acid sequence of SEQ ID NO: 103. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 121 and/or a VL sequence having at least about any of 90%, 91%, 92%, 93%, 94%, 95%, 96%, 97%, 98%, 99%, or 100% sequence identity to the amino acid sequence of SEQ ID NO: 120. In some embodiments, the antibody comprises a VH sequence of SEQ ID NO: 121 and/or a VL sequence of SEQ ID NO: 120. In some embodiments of any of the antibodies, the antibody comprises six HVRs of 3C10. In some embodiments, the antibody comprises VH domain and VL domain of 3C10. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes.

Provided herein, and in some embodiments, are antibodies comprising a) a heavy chain comprising a HVR-H1 comprising the amino acid sequence of SEQ ID NO:44, HVR-H2 comprising the amino acid sequence of SEQ ID NO:68, and HVR-H3 comprising the amino acid sequence of SEQ ID NO:92; and/or b) a light chain comprising a HVR-L1 comprising the amino acid sequence of SEQ ID NO:8, HVR-L2 comprising the amino acid sequence of SEQ ID NO:20, and HVR-L3 comprising the amino acid sequence of SEQ ID NO:32. In some embodiments, the heavy chain comprising a HVR-H1 comprising the amino acid sequence of SEQ ID NO:56, HVR-H2 comprising the amino acid sequence of SEQ ID NO:80, and HVR-H3 comprising the amino acid sequence of SEQ ID NO: 104. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 123 and/or a VL sequence having at least about any of 90%, 91%, 92%, 93%, 94%, 95%, 96%, 97%, 98%, 99%, or 100% sequence identity to the amino acid sequence of SEQ ID NO: 122. In some embodiments, the antibody comprises a VH sequence of SEQ ID NO: 123 and/or a VL sequence of SEQ ID NO: 122. In some embodiments of any of the antibodies, the antibody comprises six HVRs of 3F10. In some embodiments, the antibody comprises VH domain and VL domain of 3F10. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes. In some embodiments, the antibody does not significantly cross react with FcRH5a.

Provided herein, and in some embodiments, are antibodies comprising a) a heavy chain comprising a HVR-H1 comprising the amino acid sequence of SEQ ID NO:45, HVR-H2 comprising the amino acid sequence of SEQ ID NO:69, and HVR-H3 comprising the amino acid sequence of SEQ ID NO:93; and/or b) a light chain comprising a HVR-L1 comprising the amino acid sequence of SEQ ID NO:9, HVR-L2 comprising the amino acid sequence of SEQ ID NO:21, and HVR-L3 comprising the amino acid sequence of SEQ ID NO:33. In some embodiments, the heavy chain comprising a HVR-H1 comprising the amino acid sequence of SEQ ID NO:57, HVR-H2 comprising the amino acid sequence of SEQ ID NO:81, and HVR-H3 comprising the amino acid sequence of SEQ ID NO: 105. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 125 and/or a VL sequence having at least about any of 90%, 91%, 92%, 93%, 94%, 95%, 96%, 97%, 98%, 99%, or 100% sequence identity to the amino acid sequence of SEQ ID NO: 124. In some embodiments, the antibody comprises a VH sequence of SEQ ID NO: 125 and/or a VL sequence of SEQ ID NO: 124. In some embodiments of any of the antibodies, the antibody comprises six HVRs of 3G3. In some embodiments, the antibody comprises VH domain and VL domain of 3G3. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes. In some embodiments, the antibody does not significantly cross react with FcRH5a.

Provided herein, and in some embodiments, are antibodies comprising a) a heavy chain comprising a HVR-H1 comprising the amino acid sequence of SEQ ID NO:46, HVR-H2 comprising the amino acid sequence of SEQ ID NO:70, and HVR-H3 comprising the amino acid sequence of SEQ ID NO:94; and/or b) a light chain comprising a HVR-L1 comprising the amino acid sequence of SEQ ID NO: 10, HVR-L2 comprising the amino acid sequence of SEQ ID NO:22, and HVR-L3 comprising the amino acid sequence of SEQ ID NO:34. In some embodiments, the heavy chain comprising a HVR-H1 comprising the amino acid sequence of SEQ ID NO:58, HVR-H2 comprising the amino acid sequence of SEQ ID NO:82, and HVR-H3 comprising the amino acid sequence of SEQ ID NO: 106. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 127 and/or a VL sequence having at least about any of 90%, 91%, 92%, 93%, 94%, 95%, 96%, 97%, 98%, 99%, or 100% sequence identity to the amino acid sequence of SEQ ID NO: 126. In some embodiments, the antibody comprises a VH sequence of SEQ ID NO: 127 and/or a VL sequence of SEQ ID NO: 126. In some embodiments of any of the antibodies, the antibody comprises six HVRs of 3G7.1.5. In some embodiments, the antibody comprises VH domain and VL domain of 3G7.1.5. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes.

Provided herein, and in some embodiments, are antibodies comprising a) a heavy chain comprising a HVR-H1 comprising the amino acid sequence of SEQ ID NO:47, HVR-H2 comprising the amino acid sequence of SEQ ID NO:71, and HVR-H3 comprising the amino acid sequence of SEQ ID NO:95; and/or b) a light chain comprising a HVR-L1 comprising the amino acid sequence of SEQ ID NO: 11, HVR-L2 comprising the amino acid sequence of SEQ ID NO:23, and HVR-L3 comprising the amino acid sequence of SEQ ID NO:35. In some embodiments, the heavy chain comprising a HVR-H1 comprising the amino acid sequence of SEQ ID NO:59, HVR-H2 comprising the amino acid sequence of SEQ ID NO:83, and HVR-H3 comprising the amino acid sequence of SEQ ID NO: 107. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 129 and/or a VL sequence having at least about any of 90%, 91%, 92%, 93%, 94%, 95%, 96%, 97%, 98%, 99%, or 100% sequence identity to the amino acid sequence of SEQ ID NO: 128. In some embodiments, the antibody comprises a VH sequence of SEQ ID NO: 129 and/or a VL sequence of SEQ ID NO: 128. In some embodiments of any of the antibodies, the antibody comprises six HVRs of 5A10.1.3. In some embodiments, the antibody comprises VH domain and VL domain of 5A10.1.3. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes.

Provided herein, and in some embodiments, are antibodies comprising a) a heavy chain comprising a HVR-H1 comprising the amino acid sequence of SEQ ID NO:48, HVR-H2 comprising the amino acid sequence of SEQ ID NO:72, and HVR-H3 comprising the amino acid sequence of SEQ ID NO:96; and/or b) a light chain comprising a HVR-L1 comprising the amino acid sequence of SEQ ID NO: 12, HVR-L2 comprising the amino acid sequence of SEQ ID NO:24, and HVR-L3 comprising the amino acid sequence of SEQ ID NO:36. In some embodiments, the heavy chain comprising a HVR-H1 comprising the amino acid sequence of SEQ ID NO:60, HVR-H2 comprising the amino acid sequence of SEQ ID NO:84, and HVR-H3 comprising the amino acid sequence of SEQ ID NO: 108. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 131 and/or a VL sequence having at least about any of 90%, 91%, 92%, 93%, 94%, 95%, 96%, 97%, 98%, 99%, or 100% sequence identity to the amino acid sequence of SEQ ID NO:130. In some embodiments, the antibody comprises a VH sequence of SEQ ID NO: 131 and/or a VL sequence of SEQ ID NO: 130. In some embodiments of any of the antibodies, the antibody comprises six HVRs of 5F1.1.5. In some embodiments, the antibody comprises VH domain and VL domain of 5F1.1.5. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes. In some embodiments, the antibody does not significantly cross react with FcRH5a.

Provided herein, and in some embodiments, are antibodies comprising a) a heavy chain comprising a HVR-H1 comprising the amino acid sequence of SEQ ID NO:49, HVR-H2 comprising the amino acid sequence of SEQ ID NO:73, and HVR-H3 comprising the amino acid sequence of SEQ ID NO:97; and/or b) a light chain comprising a HVR-L1 comprising the amino acid sequence of SEQ ID NO: 13, HVR-L2 comprising the amino acid sequence of SEQ ID NO:25, and HVR-L3 comprising the amino acid sequence of SEQ ID NO:37. In some embodiments, the heavy chain comprising a HVR-H1 comprising the amino acid sequence of SEQ ID NO:61, HVR-H2 comprising the amino acid sequence of SEQ ID NO:85, and HVR-H3 comprising the amino acid sequence of SEQ ID NO: 109. In some embodiments, the antibody comprises a VH sequence having at least about any of 90%, 91%, 92%, 93%, 94%, 95%, 96%, 97%, 98%, 99%, or 100% sequence identity to the amino acid sequence of SEQ ID NO: 133 and/or a VL sequence having at least about any of 90%, 91%, 92%, 93%, 94%, 95%, 96%, 97%, 98%, 99%, or 100% sequence identity to the amino acid sequence of SEQ ID NO: 132. In some embodiments, the antibody comprises a VH sequence of SEQ ID NO: 133 and/or a VL sequence of SEQ ID NO: 132. In some embodiments of any of the antibodies, the antibody comprises six HVRs of 6D2. In some embodiments, the antibody comprises VH domain and VL domain of 6D2. In some embodiments, the antibody binds an isoform c-specific region of the extracellular domain of FcRH5c (e.g., Ig-like domain 9). In some embodiments, the antibody is cross reactive with full length human and cyno FcRH5. In some embodiments, the antibody does not significantly cross react with FcRH1, FcRH2, FcRH3, and/or FcRH4. In some embodiments, the antibody binds to endogenous FcRH5. In some embodiments, the antibody binds B-cells. In some embodiments, the antibody does not significantly bind NK cells and/or monocytes.

In a further aspect provided herein, an anti-FcRH5 antibody according to any of the above embodiments is a monoclonal antibody, including a chimeric, humanized or human antibody. In one embodiment, an anti-FcRH5 antibody is an antibody fragment, e.g., a Fv, Fab, Fab', scFv, diabody, or $F(ab')_2$ fragment. In another embodiment, the antibody is a substantially full length antibody, e.g., an IgG1 antibody or other antibody class or isotype as defined herein.

In a further aspect, the invention provides an antibody that binds to the same epitope as an anti-FcRH5 antibody provided herein. In certain embodiments, an antibody is provided that binds an isoform c-specific region of the extracellular domain of FcRH5c from, within, or overlapping amino acids 754-835 of SEQ ID NO:1.

In some embodiments of any of the anti-FcRH5 antibodies, the FcRH5 antibody, particularly an FcRH5 bispecific (e.g., anti-CD3/anti-FcRH5 bispecific), may have features, singly or in combination, based upon HEK cell line assays (HEK cells reconstituted with necessary signaling components for the TCR triggering as described in James and Valle, *Nature* 487:64-69 (2012), which is incorporated by reference in its entirety. In some embodiments, the features, singly or in combination, may include tumor cell interphase/immunological synapse, Lck-mediated TCR phosphorylation, ZAP70 activity including phosphorylation state and localization, CD58 activity including localization and binding, $\beta_2$Ar activity including localization and binding, CAAX activity including localization and binding CD45 activity including localization, pMHC activity including localization, and/or TCR activity and triggering features.

In a further aspect, an anti-FcRH5 antibody according to any of the above embodiments may incorporate any of the features, singly or in combination, as described in (a)-(e) and/or Sections 1-7 below.

(a) Binds an Isoform c-Specific Region of the Extracellular Domain of FcRH5c

Methods of determining whether an anti-FcRH5 antibody binds to an isoform c-specific region of the extracellular domain of FcRH5c are known in the art. In some embodiments, binding of an anti-FcRH5 antibody to an isoform c-specific region of the extracellular domain of FcRH5c may be determined by expressing FcRH5 polypeptides with N- and C-terminal deletions in 293 cells and/or SVT2 cells and testing by FACS as described in the Examples binding of the antibody to the truncated polypeptides. In some embodiments, a substantial reduction (≥70% reduction) or elimination of binding of the antibody to a truncated polypeptide relative to binding to full-length FcRH5 expressed in 293 cells indicates that the antibody does not bind to that truncated polypeptide.

In some embodiments, the isoform c-specific region comprises Ig-like domain 9. In some embodiments, the Ig-like domain 9 is also called Ig-like C2-type 8. In some embodiments, the isoform c-specific region comprises amino acids 754-835 of SEQ ID NO: 1. In some embodiments, the isoform c-specific region comprises amino acids 752-834 of SEQ ID NO: 1. In some embodiments, the isoform c-specific region comprises amino acids 743-850 of SEQ ID NO: 1. In some embodiments, the isoform c-specific region comprises amino acids 745-851 of SEQ ID NO: 1. In some embodiments, the isoform c-specific region comprises amino acids about any of 1, 2, 3, 4, 5, 6, 7, 8, 9, 10, 11, 12, 13, 14, or 15 from the N-terminal and/or C-terminal boundary. In some embodiments, the isoform c-specific region comprises amino acids from about any of 750, 751, 752, 753, or 754 to about any of 830, 831, 832, 833, 834, 835, or 836 of SEQ ID NO: 1. In some embodiments, FcRH5 is human FcRH5. In some embodiments, FcRH5 is human FcRH5 or cynomolgus monkey FcRH5.

(b) Cross Reacts with (Binds) Human and Cyno FcRH5 with an Affinity of ≤5 nM, or ≤4 nM, or ≤3 nM, or ≤2 nM, or ≤1 nM, and Optionally ≥0.0001 nM, or ≥0.001 nM, or ≥0.01 nM Methods of determining binding affinity are known in the art. In some embodiments, the binding affinity may be determined according to a BIAcore© assay, ELISA, Facs, and IHC, for example, as described in the Examples.

In some embodiments, the anti-FcRH5 antibody binds human and/or cyno FcRH5 with an affinity of about any of ≤5 nM, or ≤4 nM, or ≤3 nM, or ≤2 nM, or ≤1 nM. In some embodiments, the anti-FcRH5 antibody binds human and/or cyno FcRH5 with an affinity of about ≤5. In some embodiments, the anti-FcRH5 antibody binds human and/or cyno FcRH5 with an affinity of about ≤4 nM. In some embodiments, the anti-FcRH5 antibody binds human and/or cyno FcRH5 with an affinity of about ≤3 nM. In some embodiments, the anti-FcRH5 antibody binds human and/or cyno FcRH5 with an affinity of about ≤2 nM. In some embodiments, FcRH5 is human FcRH5. In some embodiments, FcRH5 is cynomolgus monkey FcRH5.

(c) Does not Cross React with (does not Bind) FcRH1, FcRH2, FcRH3, and or FcRH4

Methods of determining binding are known in the art. In some embodiments, the binding affinity may be determined according to a BIAcore® assay, Facs, ELISA, and IHC, for example, as described in the Examples.

In some embodiments, the anti-FcRH5 antibody binds FcRH5 with an affinity of more than about any of 2, 5, 10, 20, 50, 100, 500, or 1000-fold greater than FcRH1, FcRH2, FcRH3, and/or FcRH4. In some embodiments, FcRH is human FcRH.

(d) does not Cross React with (does not Bind) FcRH5a

Methods of determining binding are known in the art. In some embodiments, the binding affinity may be determined according to a BIAcore® assay, Facs, ELISA, and IHC, for example, as described in the Examples.

In some embodiments, the anti-FcRH5 antibody binds FcRH5c with an affinity of more than about any of 2, 5, 10, 20, 50, 100, 500, or 1000-fold greater than FcRH5a. In some embodiments, FcRH is human FcRH.

(e) does not Cross React with Another Ig-Like Domain (does not Bind) of FcRH5

Methods of determining binding are known in the art. In some embodiments, the binding affinity may be determined according to a BIAcore® assay, Facs, ELISA, and IHC, for example, as described in the Examples.

In some embodiments, the anti-FcRH5 antibody binds Ig-like domain 9 of FcRH5 with an affinity of more than about any of 2, 5, 10, 20, 50, 100, 500, or 1000-fold greater than Ig-like domain 1, 2, 3, 4, 5, 6, 7, and/or 8 of FcRH5. In some embodiments, FcRH is human FcRH. In some embodiments, the Ig-like domain is Ig-like domain 1 (aa 23-100 of SEQ ID NO: 1), Ig-like domain 2 (aa 105-185 of SEQ ID NO: 1), Ig-like domain 3 (aa 188-271 of SEQ ID NO: 1), Ig-like domain 4 (287-373 of SEQ ID NO: 1), Ig-like domain 5 (aa 380-466 of SEQ ID NO: 1), Ig-like domain 6 (aa 490-555 of SEQ ID NO: 1), Ig-like domain 7 (aa 568-652 of SEQ ID NO:1), Ig-like domain 8 (aa 658-731 of SEQ ID NO: 1).

Binding Assays and Other Assays

In one aspect, an anti-FcRH5 antibody is tested for its antigen binding activity. For example, in certain embodiments, an anti-FcRH5 antibody is tested for its ability to bind to FcRH5 expressed on the surface of a cell. A FACS assay may be used for such testing.

In an exemplary competition assay, immobilized FcRH5 is incubated in a solution comprising a first labeled antibody that binds to FcRH5 and a second unlabeled antibody that is being tested for its ability to compete with the first antibody for binding to FcRH5. The second antibody may be present in a hybridoma supernatant. As a control, immobilized FcRH5 is incubated in a solution comprising the first labeled antibody but not the second unlabeled antibody. After incubation under conditions permissive for binding of the first antibody to FcRH5, excess unbound antibody is removed, and the amount of label associated with immobilized FcRH5 is measured. If the amount of label associated with immobilized FcRH5 is substantially reduced in the test sample relative to the control sample, then that indicates that the second antibody is competing with the first antibody for binding to FcRH5. In certain embodiments, immobilized FcRH5 is present on the surface of a cell or in a membrane preparation obtained from a cell expressing FcRH5 on its surface.

In one aspect, purified anti-FcRH5 antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion. In one embodiment, contemplated are an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, Annu. Rev. Immunol. 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM, and optionally is $\geq 10^{-13}$ M. (e.g. $10^{-8}$ M or less, e.g. from $10^{-8}$M to $10^{-13}$ M, e.g., from $10^{-9}$ M to $10^{-13}$ M).

In some embodiments, Kd may be measured by a radiolabeled antigen binding assay (RIA) performed with the Fab version of an antibody of interest and its antigen as described by the following assay. Solution binding affinity of Fabs for antigen may be measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) may be coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures may be transferred to the capture plate for incubation at room temperature (e.g., for one hour). The solution may be then removed and the plate washed eight times with 0.1% polysorbate 20 (TWEEN-20®) in PBS. When the plates have dried, 150 μL/well of scintillant (MICROSCINT-20™; Packard) may be added, and the plates may be counted on a TOPCOUNT™ gamma counter (Packard) for ten minutes. Concentrations of each Fab that give less than or equal to 20% of maximal binding may be chosen for use in competitive binding assays.

According to another embodiment, Kd is measured using surface plasmon resonance assays using a BIACORE®-2000 or a BIACORE®-3000 (BIAcore, Inc., Piscataway, NJ) at 25° C. with immobilized antigen CM5 chips at ~10 response units (RU). Briefly, carboxymethylated dextran biosensor chips (CM5, BIACORE, Inc.) may be activated with N-ethyl-N'-(3-dimethylaminopropyl)-carbodiimide hydrochloride (EDC) and N-hydroxysuccinimide (NHS) according to the supplier's instructions. Antigen may be diluted with 10 mM sodium acetate, pH 4.8, to 5 μg/ml (~0.2 μM) before injection at a flow rate of 5 μL/minute to achieve approximately 10 response units (RU) of coupled protein. Following the injection of antigen, 1 M ethanolamine may be injected to block unreacted groups. For kinetics measurements, two-fold serial dilutions of Fab (0.78 nM to 500 nM) may be injected in PBS with 0.05% polysorbate 20 (TWEEN-20™) surfactant (PBST) at 25° C. at a flow rate of approximately 25 μL/min. Association rates ($k_{on}$) and dissociation rates ($k_{off}$) may be calculated using a simple one-to-one Langmuir binding model (BIACORE® Evaluation Software version 3.2) by simultaneously fitting the association and dissociation sensorgrams. The equilibrium dissociation constant (Kd) may be calculated as the ratio $k_{off}/k_{on}$ See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate may be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, $F(ab')_2$, Fv, and scFv fragments, and other fragments described below. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J Biol. Chem.* 272:10678-10684 (1997) and Rosok et al., *J Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications*, pp. 51-63 (Marcel Dekker, Inc., New York, 1987); and Boerner et al., *J Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies provided herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments.

Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for FcRH5 and the other is for any other antigen. In certain embodiments, one of the binding specificities is for FcRH5 and the other is for CD3. See, e.g., U.S. Pat. No. 5,821,337. In certain embodiments, bispecific antibodies may bind to two different epitopes of FcRH5. Bispecific antibodies may also be used to localize cytotoxic agents to cells which express FcRH5. Bispecific antibodies can be prepared as full length antibodies or antibody fragments.

In some embodiments, the FcRH5 antibodies are FcRH5 bispecific antibodies. Bispecific antibodies are antibodies that have binding specificities for at least two different epitopes. Exemplary bispecific antibodies may bind to two different epitopes of an FcRH5 protein as described herein. Other such antibodies may combine an FcRH5 binding site with a binding site for another protein. Alternatively, an anti-FcRH5 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the FcRH5-expressing cell. Bispecific antibodies may also be used to localize cytotoxic agents to cells which express FcRH5. These antibodies possess an FcRH5-binding arm and an arm which binds the cytotoxic agent (e.g., saporin, anti-interferon α vinca alkaloid, ricin A chain, methotrexate or radioactive isotope hapten). Bispecific antibodies can be prepared as full length antibodies or antibody fragments (e.g., $F(ab')_2$ bispecific antibodies). In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In some embodiments, the FcRH5 bispecific antibody comprises a first arm, wherein the first arm binds FcRH5 and a second arm, wherein the second arm binds a Fc. The second arm of the FcRH5 bispecific antibody may be any anti-Fc antibody known in the art. For example, WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In some embodiments, the FcRH5 bispecific antibody comprises a first arm, wherein the first arm binds FcRH5 and a second arm, wherein the second arm binds CD3. The second arm of the FcRH5 bispecific antibody may be any anti-CD3 antibody known in the art. U.S. Pat. Nos. 5,821,337 and 6,407,213 teach bispecific anti-ErbB2/anti-CD3 antibodies. Additional bispecific antibodies that bind an epitope on the CD3 antigen and a second epitope have been described. See, for example, U.S. Pat. No. 5,078,998 (anti-CD3/tumor cell antigen); U.S. Pat. No. 5,601,819 (anti-CD3/IL-2R; anti-CD3/CD28; anti-CD3/CD45); U.S. Pat. No. 6,129,914 (anti-CD3/malignant B-cell antigen); U.S. Pat. No. 7,112,324 (anti-CD3/CD19); U.S. Pat. No. 6,723,538 (anti-CD3/CCR5); U.S. Pat. No. 7,235,641 (anti-CD3/EpCAM); U.S. Pat. No. 7,262,276 (anti-CD3/ovarian tumor antigen); and U.S. Pat. No. 5,731,168 (anti-CD3/CD4IgG), which are incorporated by reference in their entirety. In some embodiments, the anti-CD3 antibody of the second arm is an antibody described in any one of WO 2005/118635, WO2007/042261, WO2008/119567, U.S. Pat. Nos. 5,929,212, 6,750,325, 6,491,916, 7,994,289, 7,993,641, 6,706,265, 5,585,097, 5,968,509, 5,932,448, 6,129,914, 7,381,803, 5,834,597, and US7862813, which are incorporated by reference in their entirety. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to FcRH5 as well as another, different antigen (see, US 2008/0069820, for example).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In some embodiments, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. Bispecific antibodies produced in accordance with this approach are referred to herein as "protuberance-into-cavity" antibodies.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments from *E. coli* can be directly recovered and chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and V domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

Antibodies with more than two valencies are contemplated. For example, trispecific antibodies can be prepared. Tutt et al., *J. Immunol.* 147:60 (1991).

8. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody provided herein may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96© non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half-lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-FcRH5 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-FcRH5 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-FcRH5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

C. Assays

Anti-FcRH5 antibodies provided herein may be identified, screened for, or characterized for their physical/chemical properties and/or biological activities by various assays known in the art.

In one aspect, an antibody provided herein may be tested for its antigen binding activity, e.g., by known methods such as ELISA, BIACore®, FACS, or Western blot.

In another aspect, competition assays may be used to identify an antibody that competes with any of the antibodies described herein for binding to FcRH5. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized FcRH5 is incubated in a solution comprising a first labeled antibody that binds to FcRH5 (e.g., any of the antibodies described herein) and a second unlabeled antibody that is being tested for its ability to compete with the first antibody for binding to FcRH5. The second antibody may be present in a hybridoma supernatant. As a control, immobilized FcRH5 is incubated in a solution comprising the first labeled antibody but not the second unlabeled antibody. After incubation under conditions permissive for binding of the first antibody to FcRH5, excess unbound antibody is removed, and the amount of label associated with immobilized FcRH5 is measured. If the amount of label associated with immobilized FcRH5 is substantially reduced in the test sample relative to the control sample, then that indicates that the second antibody is competing with the first antibody for binding to FcRH5. See Harlow and Lane (1988) *Antibodies: A Laboratory Manual* ch. 14 (Cold Spring Harbor Laboratory, Cold Spring Harbor, NY). In some embodiments, the FcRH5 is FcRH5c. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

D. Immunoconjugates

Also provided herein are immunoconjugates comprising an anti-FcRH5 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate). In some embodiments, the anti-FcRH5 antibody binds an isoform c-specific region of the extracellular domain of FcRH5c. In some embodiments, the anti-FcRH5 antibodies binds Ig-like domain 9 of FcRH5c.

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds provided herein include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) provided herein selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

$$\text{Ab-(L-D)}_p \qquad \text{I}$$

where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

$$-A_a-W_w-Y_y- \qquad \text{II}$$

wherein A is a "stretcher unit", and a is an integer from 0 to 1; W is an "amino acid unit", and w is an integer from 0 to 12; Y is a "spacer unit", and y is 0, 1, or 2. An ADC comprising the linker of Formula II has the Formula I(A): Ab-($A_a$-$W_w$-$Y_y$-D)p, wherein Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

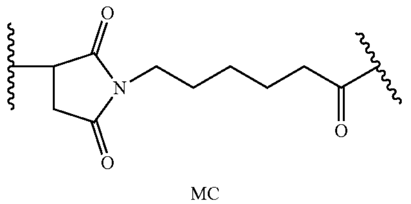

MC

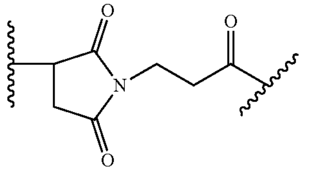

MP

-continued

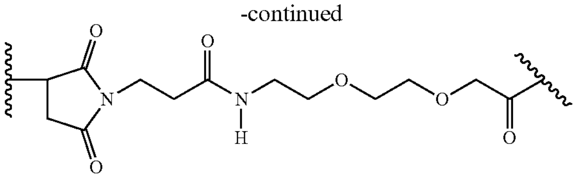

mPEG

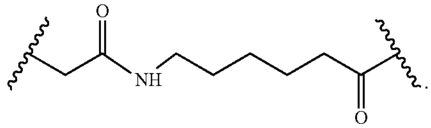

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline. Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schroder and K. Lubke (1965) "*The Peptides*", volume 1, pp 76-136, Academic Press).

In some embodiments, a linker component comprises a "spacer unit" (Y) that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). In some embodiments, the spacer unit comprises p-aminobenzyloxycarbonyl (PAB). In some embodiments, an ADC comprising a self-immolative linker has the structure:

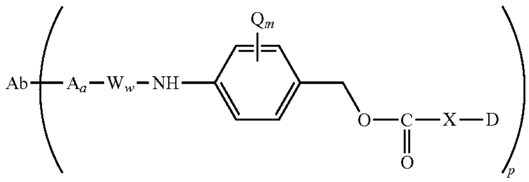

wherein Q is —$C_1$-$C_8$ alkyl, —O—($C_1$-$C_8$ alkyl), -halogen, -nitro, or -cyano; m is an integer ranging from 0 to 4; X may be one or more additional spacer units or may be absent; and p ranges from 1 to about 20. In some embodiments, p ranges from 1 to 10, 1 to 7, 1 to 5, or 1 to 4. Nonlimiting exemplary X spacer units include:

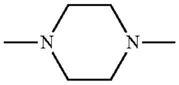
and
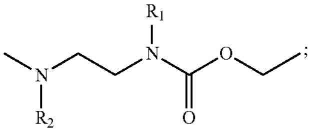
;

wherein $R_1$ and $R_2$ are independently selected from H and $C_1$-$C_6$ alkyl. In some embodiments, R1 and R2 are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J. Amer. Chem. Soc.* 94:5815) and 2-aminophenylpropionic acid amides (Amsberry, et al (1990) *J. Org. Chem.* 55:5867). Linkage of a drug to the α-carbon of a glycine residue is another example of a self-immolative spacer that may be useful in ADC (Kingsbury et al (1984) *J. Med. Chem.* 27:1447).

In some embodiments, linker L may be a dendritic type linker for covalent attachment of more than one drug moiety to an antibody through a branching, multifunctional linker moiety (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I

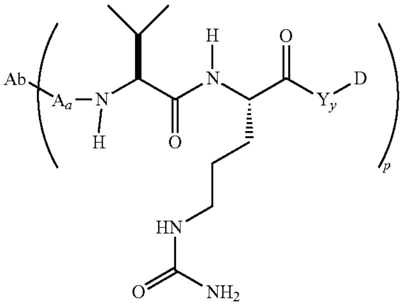

val-cit

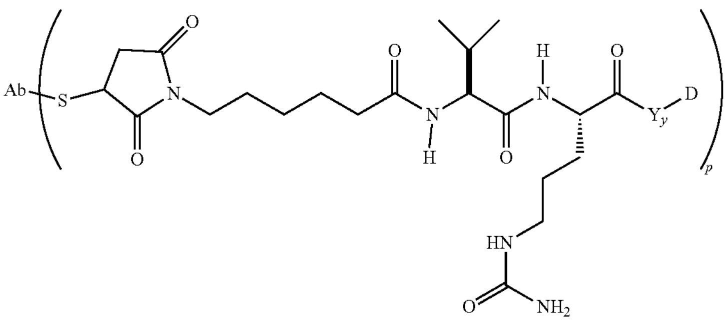

MC-val-cit

-continued
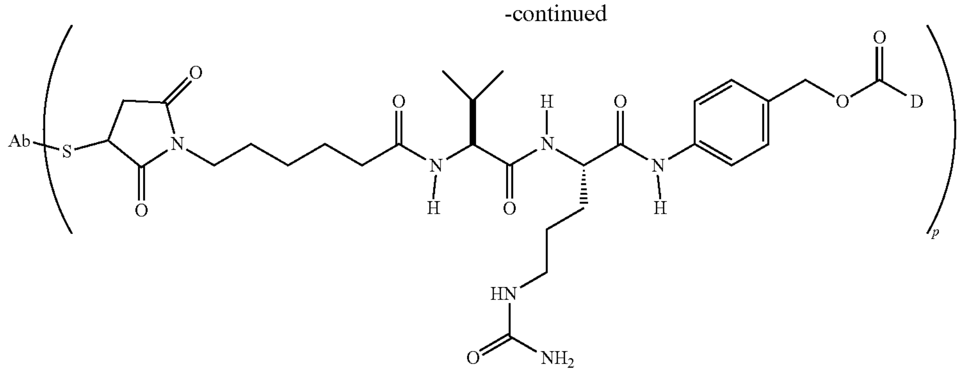
MC-val-cit-PAB
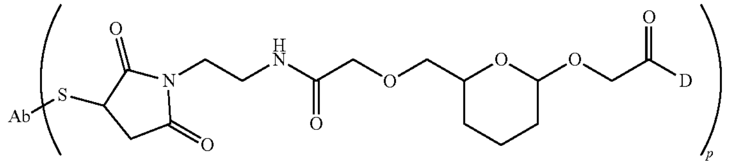
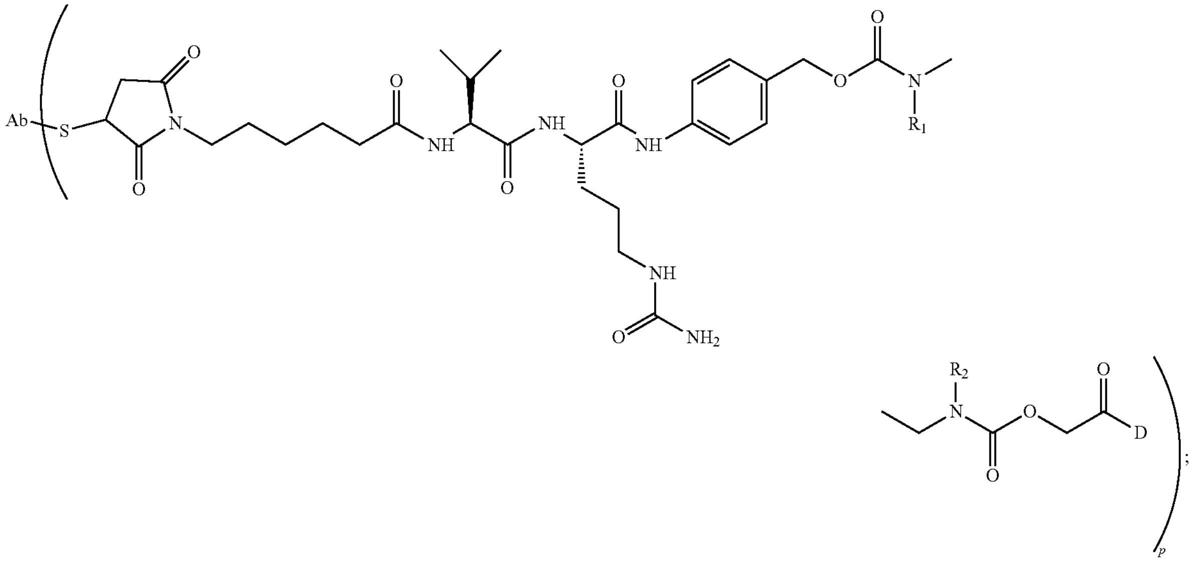
wherein $R_1$ and $R_2$ are independently selected from H and $C_1$-$C_6$ alkyl. In some embodiments, R1 and R2 are each —$CH_3$.
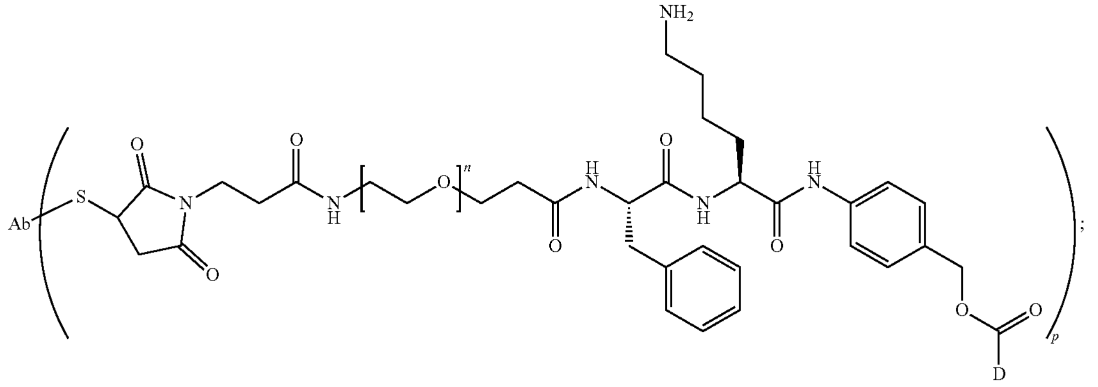
Phe-homoLys-PAB-Ab wherein n is 0 to 12. In some embodiments, n is 2 to 10.

In some embodiments, n is 4 to 8.

Further nonlimiting exemplary ADCs include the structures:

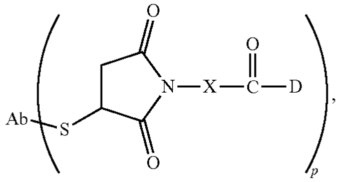

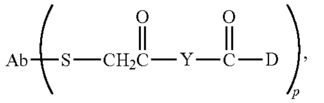

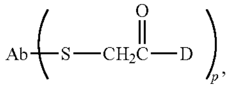

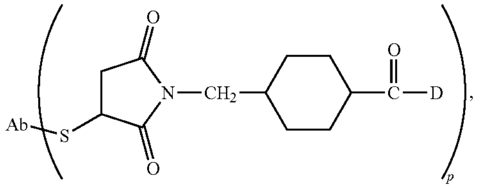

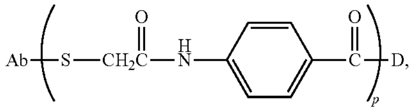

where X is: 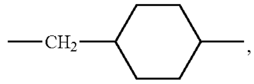, $-(Ch_2)_n-$, $-(CH_2CH_2O)_n-$,

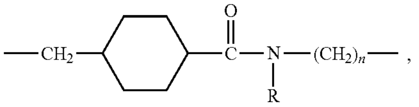

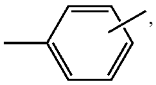, 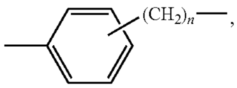

or

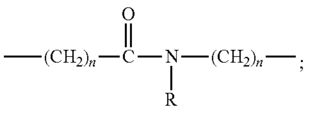

Y is:

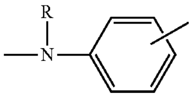 or 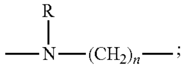

each R is independently H or $C_1$-$C_6$ alkyl; and n is 1 to 12.

In some embodiments, a linker is substituted with groups that modulate solubility and/or reactivity. As a nonlimiting example, a charged substituent such as sulfonate ($-SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)[a] is coupled to drug-(linker portion)[b] to form the ADC of Formula I.

The compounds provided herein expressly contemplate, but are not limited to, ADC prepared with the following linker reagents: bis-maleimido-trioxyethylene glycol (BMPEO), N-(D-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl)aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone) benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), $BM(PEG)_2$ (shown below), and $BM(PEG)_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

$BM(PEG)_2$

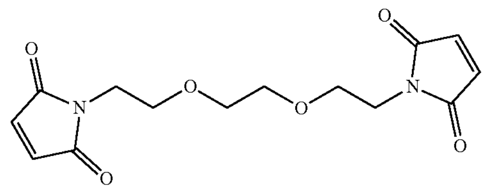

$BM(PEG)_3$

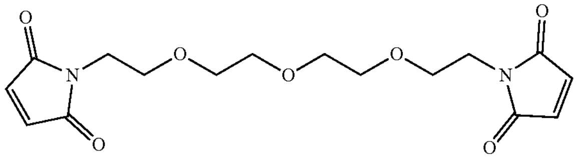

Certain useful linker reagents can be obtained from various commercial sources, such as Pierce Biotechnology, Inc. (Rockford, IL), Molecular Biosciences Inc. (Boulder, CO), or synthesized in accordance with procedures described in the art; for example, in Toki et al (2002) *J Org. Chem.* 67:1866-1872; Dubowchik, et al. (1997) *Tetrahedron Letters,* 38:5257-60; Walker, M. A. (1995) *J. Org. Chem.*

60:5352-5355; Frisch et al (1996) *Bioconjugate Chem.* 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Maytansinoid drug moieties also include those having modifications such as: C-9-SH (U.S. Pat. No. 4,424,219) (prepared, for example, by the reaction of maytansinol with $H_2S$ or $P_2S_5$); C-14-alkoxymethyl(demethoxy/$CH_2$ OR) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

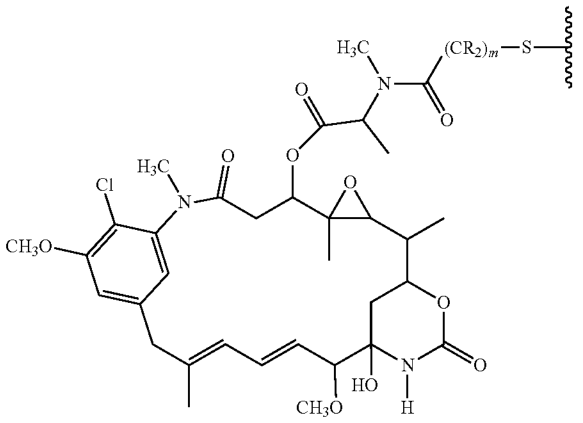

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC provided herein, i.e. any combination of R and S configurations at the chiral carbons (U.S. Pat. Nos. 7,276,497; 6,913,748; 6,441,163; 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

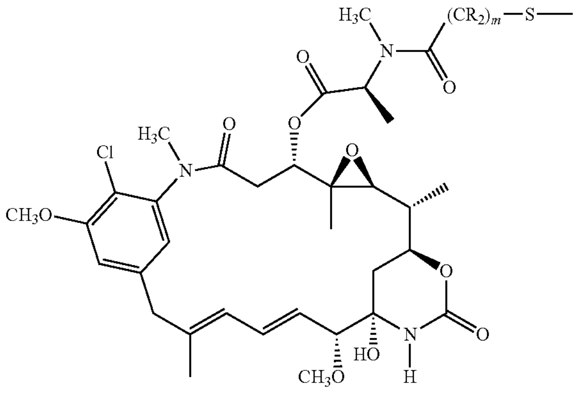

Exemplary embodiments of maytansinoid drug moieties include, but are not limited to, DM1; DM3; and DM4, having the structures:

DM1

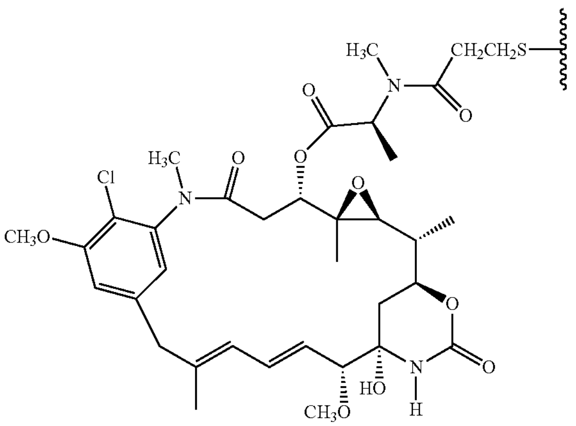

DM3

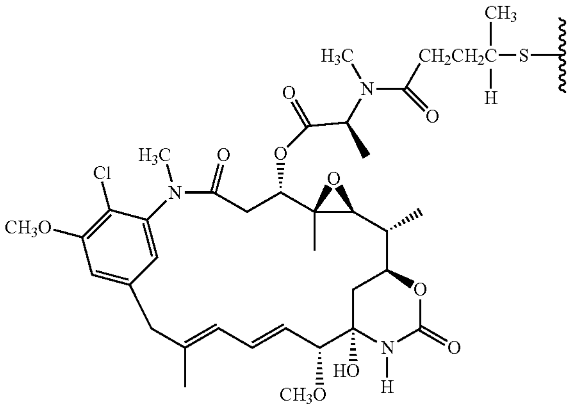

-continued

DM4

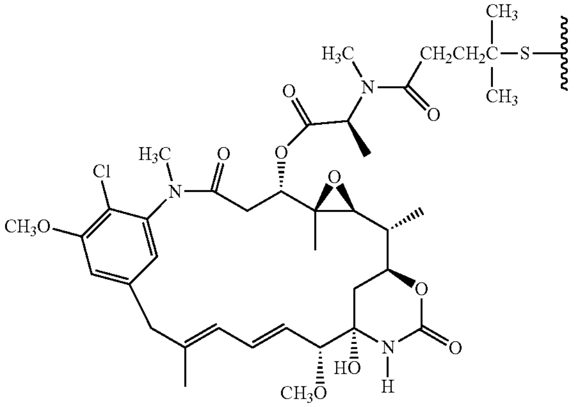

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

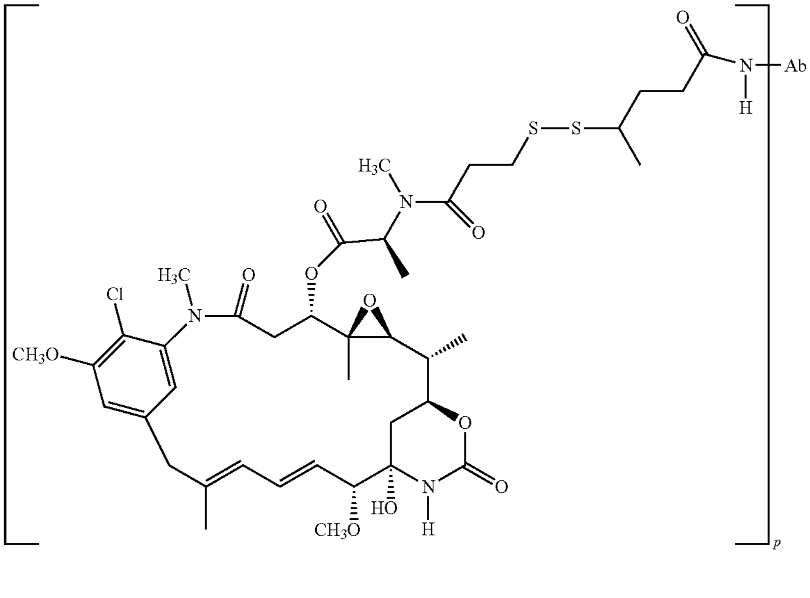

Ab -SPP-DM1

-continued

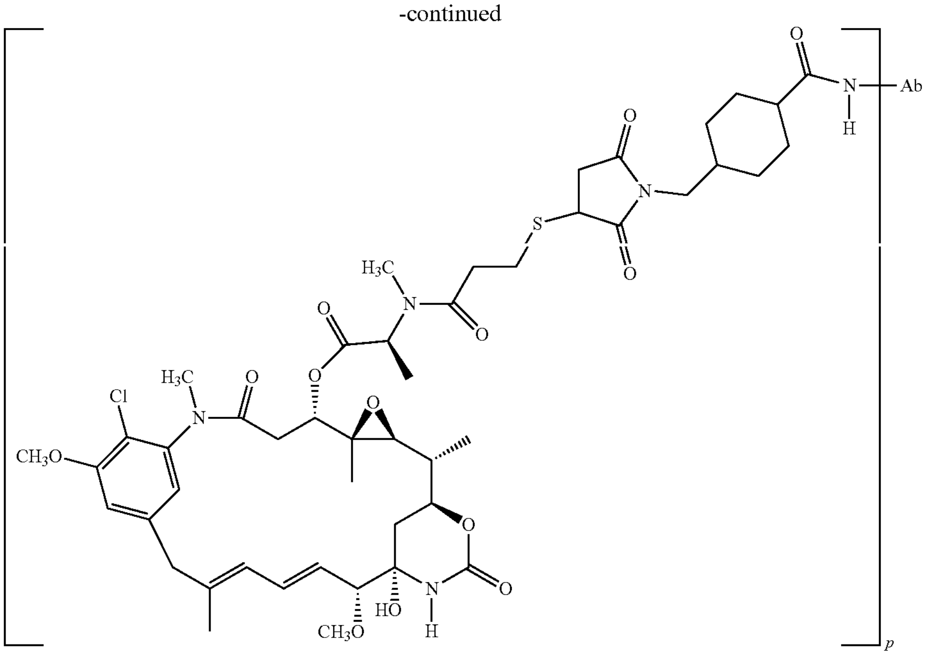

Ab-SMCC-DM1

Exemplary antibody-drug conjugates where DM1 is linked through a BMPEO linker to a thiol group of the antibody have the structure and abbreviation:

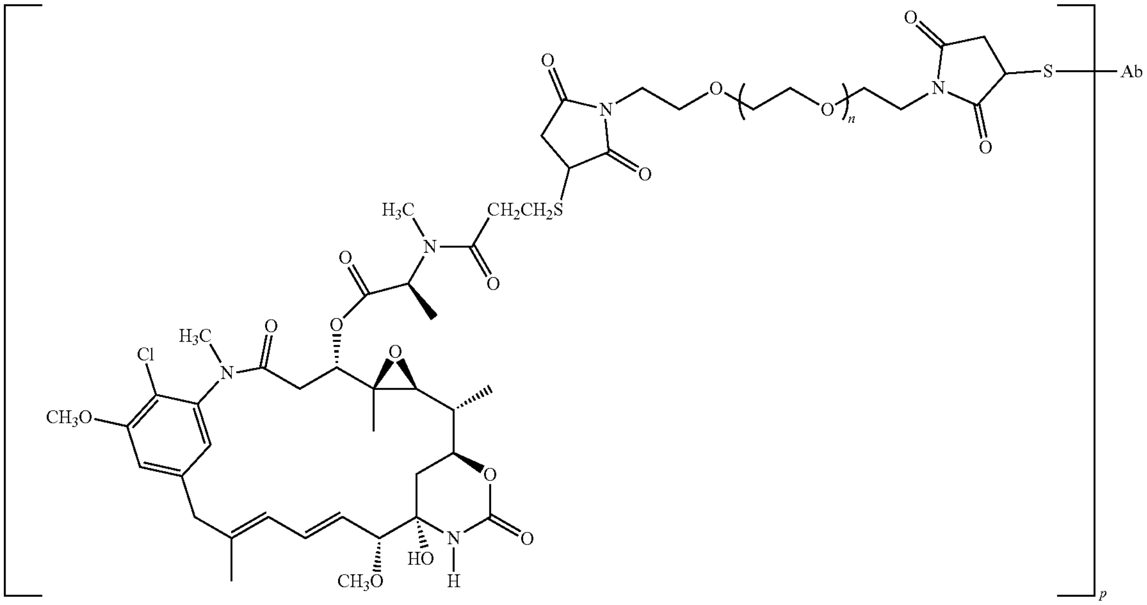

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. Nos. 5,635,483; 5,780,588; 5,767,237; 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465).

Exemplary auristatin embodiments include the N-terminus linked monomethylauristatin drug moieties $D_E$ and $D_F$, disclosed in U.S. Pat. Nos. 7,498,298 and 7,659,241, the disclosures of which are expressly incorporated by reference in their entirety:

$R^5$ is selected from H and methyl;

or $R^4$ and $R^5$ jointly form a carbocyclic ring and have the formula $-(CR^aR^b)_n-$ wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, $-(R^{13}O)_m-R^{14}$, or $-(R^{13}O)_m-CH(R^5)_2$;

m is an integer ranging from 1-1000;

$R^{13}$ is $C_2$-$C_8$ alkyl;

$R^{14}$ is H or $C_1$-$C_8$ alkyl;

each occurrence of $R^5$ is independently H, COOH, $-(CH_2)_n-N(R^{16})_2$, $-(CH_2)_n-SO_3H$, or $-(CH_2)_n-SO_3-C_1$-$C_8$ alkyl;

each occurrence of $R^{16}$ is independently H, $C_1$-$C_8$ alkyl, or $-(CH_2)_n-COOH$;

$R^{18}$ is selected from $-C(R^8)_2-C(R^8)_2$-aryl, $-C(R^8)_2-C(R^8)_2-(C_3$-$C_8$ heterocycle), and $-C(R^8)_2-C(R^8)_2-(C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl.

In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is $-OCH_3$.

$D_E$

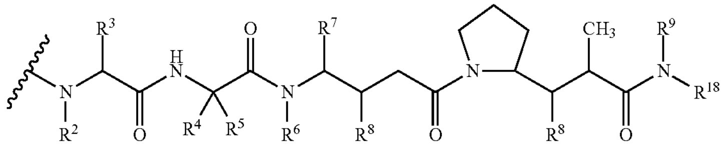

$D_F$

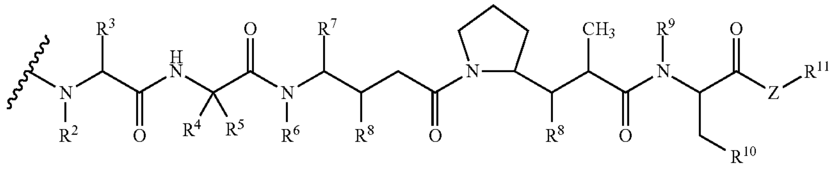

wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

In some embodiments, $R^3$ and $R^4$ are each isopropyl, $R^2$ and $R^6$ are each methyl, R is —H, $R^7$ is sec-butyl, each occurrence of $R^8$ is $-OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is $-CH(R^{11})_2$, wherein $R^{11}$ is $-(CH_2)_n-N(R^{16})_2$, and $R^{16}$ is $-C_1$-$C_8$ alkyl or $-(CH_2)_n-COOH$.

In another embodiment, when Z is —NH, $R^{11}$ is $-CH(R^{15})_2$, wherein $R^{15}$ is $-(CH_2)_n-SO_3H$.

An exemplary auristatin embodiment of formula $D_E$ is MMAE, wherein the wavy line indicates the covalent attachment to a linker (L) of an antibody-drug conjugate:

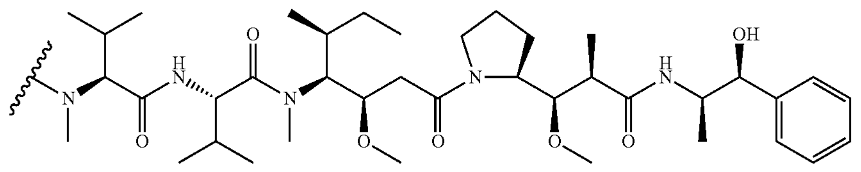

MMAE

An exemplary auristatin embodiment of formula $D_F$ is MMAF, wherein the wavy line indicates the covalent attachment to a linker (L) of an antibody-drug conjugate:

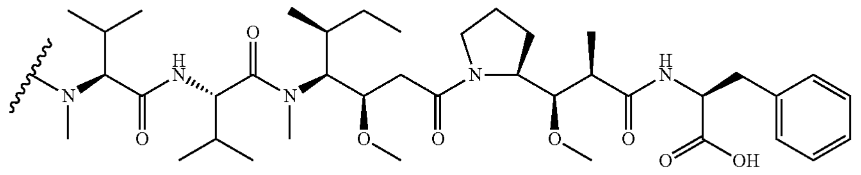

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein “Ab” is an antibody; p is 1 to about 8, “Val-Cit” is a valine-citrulline dipeptide; and “S” is a sulfur atom:

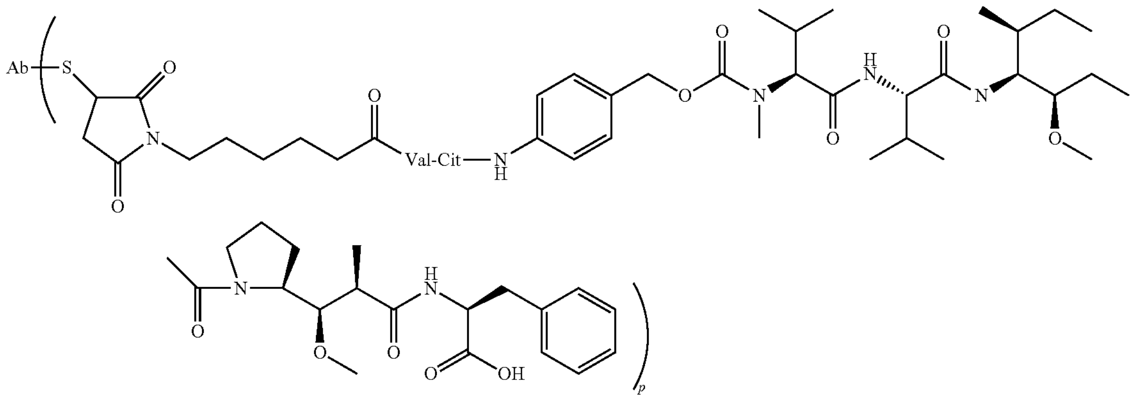

Ab-MC-vc-PAB-MMAF

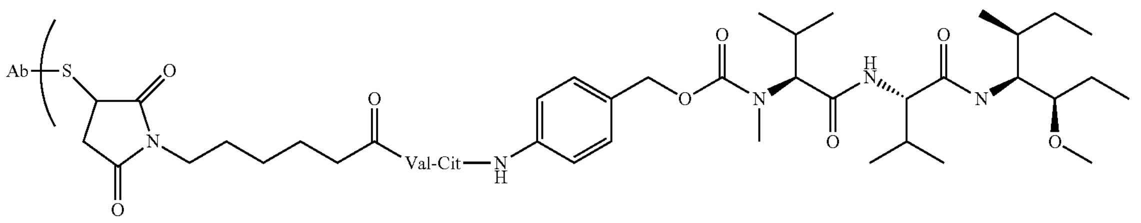

-continued

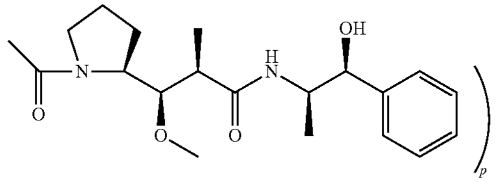

Ab-MC-vc-PAB-MMAE

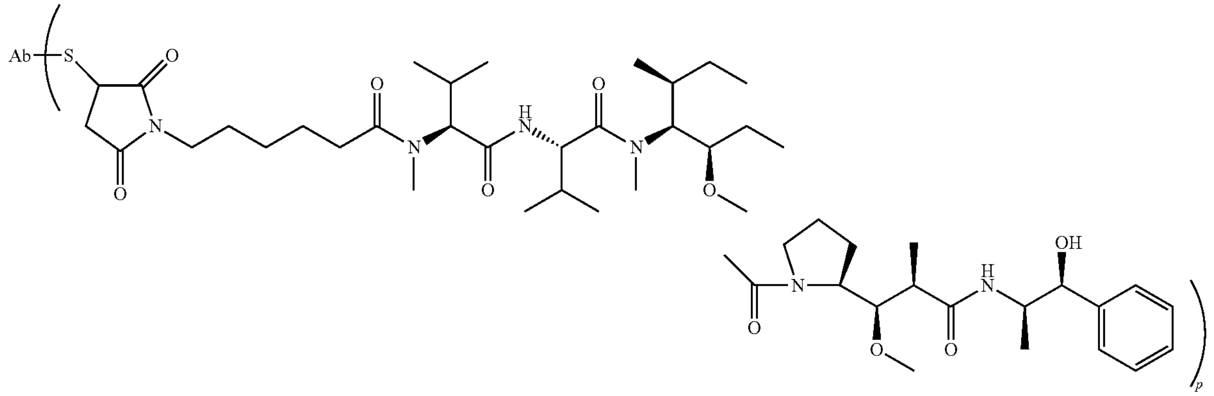

Ab-MC-MMAE

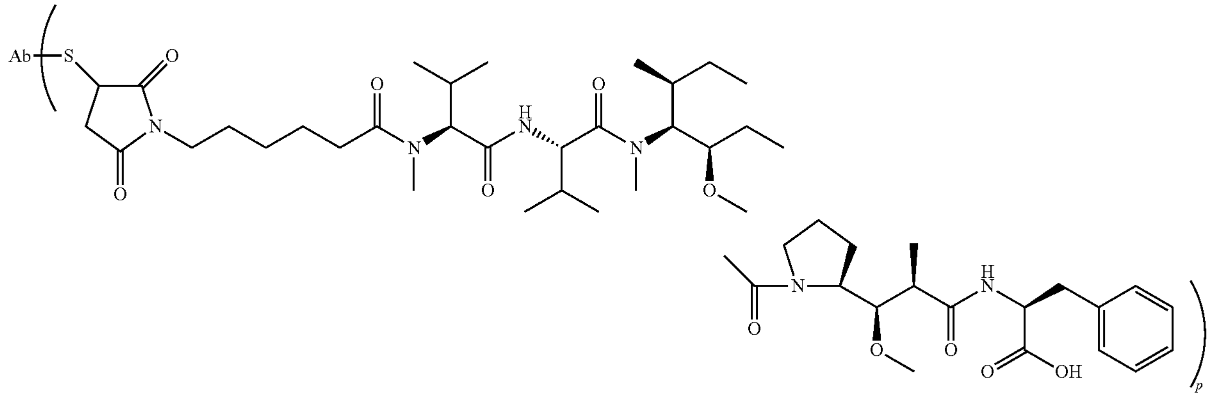

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) *Bioconjugate Chem.* 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lubke, "The Peptides", volume 1, pp 76-136, 1965, Academic Press). Auristatin/dolastatin drug moieties may, in some embodiments, be prepared according to the methods of: U.S. Pat. Nos. 7,498,298; 5,635,483; 5,780,588; Pettit et al (1989) *J. Am. Chem. Soc.* 111:5463-5465; Pettit et al (1998) *Anti-Cancer Drug Design* 13:243-277; Pettit, G. R., et al. *Synthesis,* 1996, 719-725; Pettit et al (1996) *J Chem. Soc. Perkin Trans.* 1 5:859-863; and Doronina (2003) *Nat. Biotechnol.* 21(7):778-784.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) *Bioconjugate Chem.* 17:114-124; and Doronina et al. (2003) *Nat. Biotech.* 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. Nos. 5,712,374; 5,714,586; 5,739,116; and 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J Am. Chem. Soc.,* 87:5793-5795; Leimgruber, et al., (1965) *J Am. Chem. Soc.,* 87:5791-5793). Since then, a number of PBDs, both naturally-occurring and analogues, have been reported (Thurston, et al., (1994) *Chem. Rev.* 1994, 433-465 including dimers of the tricyclic PBD scaffold (U.S. Pat. Nos. 6,884,799; 7,049,311; 7,067,511; 7,265,105; 7,511,032; 7,528,126; 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.,* 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

PBD dimers have been conjugated to antibodies and the resulting ADC shown to have anti-cancer properties. Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

$R^7$ is independently selected from H, R, OH, OR, SH, SR, $NH_2$, NHR, NRR', $NO_2$, $Me_3Sn$ and halo;

Q is independently selected from O, S and NH;

$R^{11}$ is either H, or R or, where Q is O, $SO_3M$, where M is a metal cation;

R and R' are each independently selected from optionally substituted $C_{1-s}$ alkyl, $C_{1-12}$ alkyl, $C_{3-8}$ heterocyclyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted $C_{1-12}$ alkyl, $C_{3-20}$ heterocycle, and $C_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.

In some embodiments, $R^6$ and $R^{16}$ are H.

In some embodiments, $R^7$ are $R^{17}$ are both $OR^{7A}$, where $R^{7A}$ is optionally substituted $C_{1-4}$ alkyl. In some embodiments, $R^{7A}$ is Me. In some embodiments, $R^{7A}$ is is $Ch_2Ph$, where Ph is a phenyl group.

In some embodiments, X is O.

In some embodiments, $R^{11}$ is H.

In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted $C_{5-20}$ aryl or $C_{5-7}$ aryl or $C_{8-10}$ aryl. In some embodiments, $R^2$ and $R^{12}$ are inde-

A

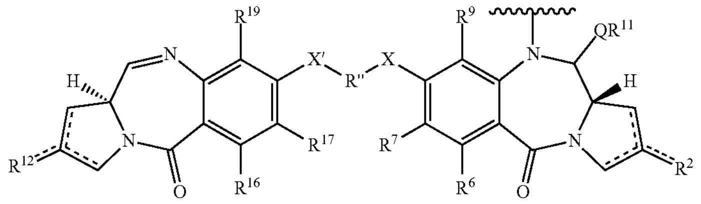

and salts and solvates thereof, wherein:

the wavy line indicates the covalent attachment site to the linker;

the dotted lines indicate the optional presence of a double bond between C1 and C2 or C2 and C3;

$R^2$ is independently selected from H, OH, $=O$, $=CH_2$, CN, R, OR, $=CH-R^D$, $=C(R^D)_2$, $O-SO_2-R$, $CO_2R$ and COR, and optionally further selected from halo or dihalo, wherein $R^D$ is independently selected from R, $CO_2R$, COR, CHO, $CO_2H$, and halo;

$R^6$ and $R^9$ are independently selected from H, R, OH, OR, SH, SR, $NH_2$, NHR, NRR', $NO_2$, $Me_3Sn$ and halo;

pendently optionally substituted phenyl, thienyl, napthyl, pyridyl, quinolinyl, or isoquinolinyl. In some embodiments, $R^2$ and $R^{12}$ are independently selected from $=O$, $=CH_2$, $=CH-R^D$, and $=C(R^D)_2$. In some embodiments, $R^2$ and $R^{12}$ each $=CH_2$. In some embodiments, $R^2$ and $R^{12}$ are each H. In some embodiments, $R^2$ and $R^{12}$ are each $=O$. In some embodiments, $R^2$ and $R^{12}$ are each $=CF_2$. In some embodiments, $R^2$ and/or $R^{12}$ are independently $=C(R^D)_2$. In some embodiments, $R^2$ and/or $R^{12}$ are independently $=CH-R^D$.

In some embodiments, when $R^2$ and/or $R^{12}$ is $=CH-R^D$, each group may independently have either configuration shown below:

(I)

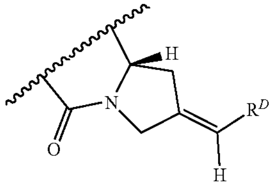

(II)

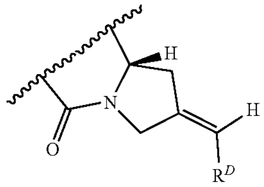

In some embodiments, a =CH—$R^D$ is in configuration (I).

In some embodiments, R" is a $C_3$ alkylene group or a $C_5$ alkylene group.

In some embodiments, an exemplary PBD dimer component of an ADC has the structure of Formula

A(I)

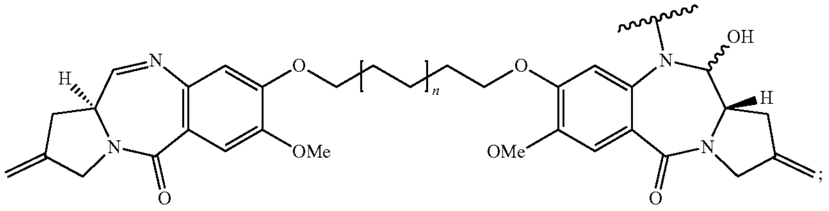

wherein n is 0 or 1.

In some embodiments, an exemplary PBD dimer component of an ADC has the structure of Formula A(II):

A(II)

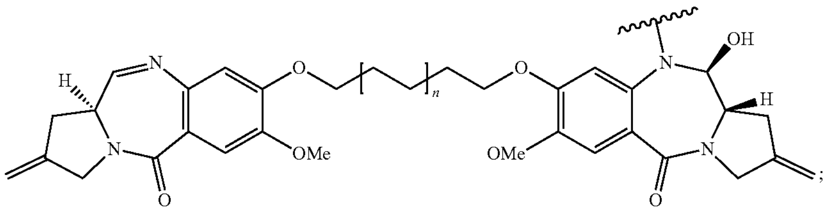

wherein n is 0 or 1.

In some embodiments, an exemplary PBD dimer component of an ADC has the structure of Formula A(III):

A(III)

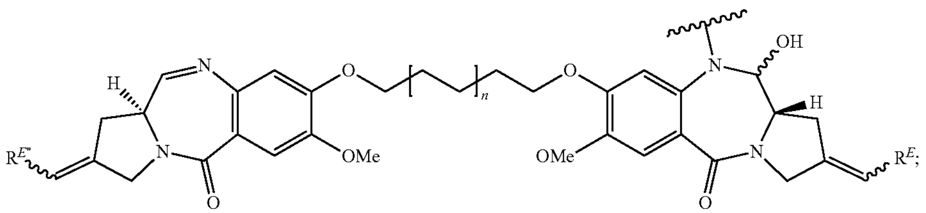

wherein $R^E$ and $R^{E''}$ are each independently selected from H or $R^D$, wherein $R^D$ is defined as above; and wherein n is 0 or 1.

In some embodiments, n is 0. In some embodiments, n is 1. In some embodiments, $R^E$ and/or $R^{E''}$ i H. In some embodiments, RE and $R^{E''}$ are H. In some embodiments, RE and/or $R^{E''}$ is $R^D$, wherein $R^D$ is optionally substituted $C_{1-12}$ alkyl. In some embodiments, RE and/or $R^{E''}$ is $R^D$, wherein $R^D$ is methyl.

In some embodiments, an exemplary PBD dimer component of an ADC has the structure of Formula A(IV):

A(IV)

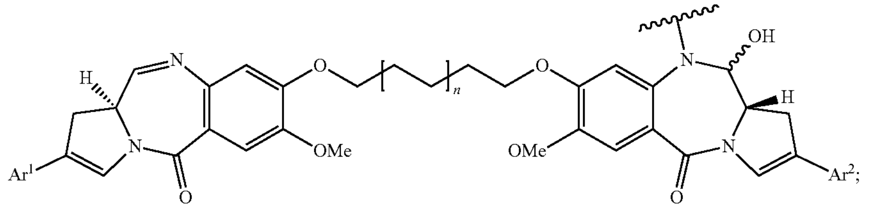

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, an exemplary PBD dimer component of an ADC has the structure of Formula A(V):

A(V)

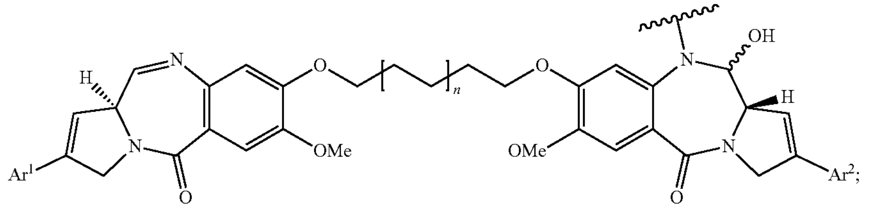

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, $Ar^1$ and $Ar^2$ are each independently selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

B

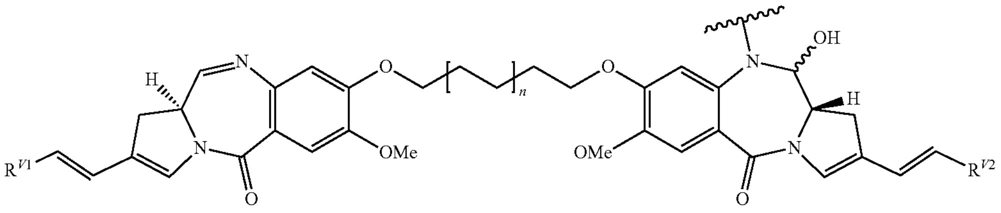

and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

-continued

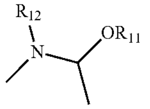

Protected Carbinolamine wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, —$NH_2$, —NHMe, —OH, and —SH, where, in some embodiments, alkyl, alkenyl and alkynyl chains comprise up to 5 carbon atoms;

C(I)

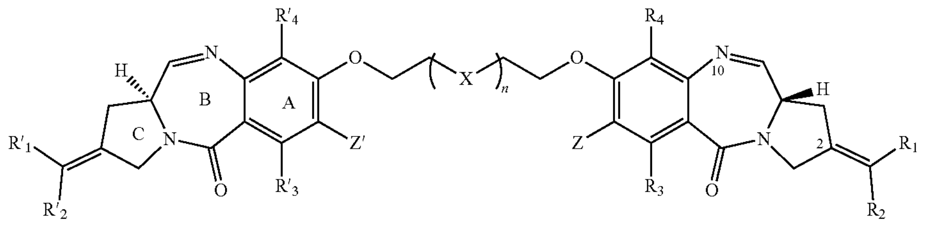

C(II)

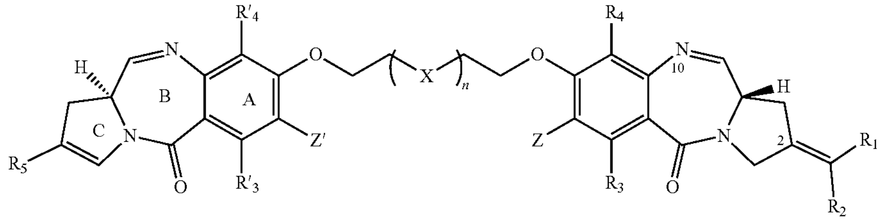

Formulas C(I) and C(II) are shown in their N10-C11 imine form. Exemplary PBD drug moieties also include the carbinolamine and protected carbinolamine forms as well, as shown in the table below:

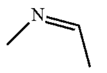

Imine

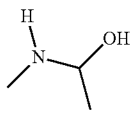

Carbinolamine $R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is is H, $C_1$-$C_8$ alkyl, or a protecting group;

wherein a hydrogen of one of $R_1$, $R'_1$, $R_2$, $R'_2$, or $R_{12}$ or a hydrogen of the —$OCH_2CH_2(X)_n CH_2CH_2O$— spacer between the A rings is replaced with a bond connected to the linker of the ADC.

Exemplary PDB dimer portions of ADC include, but are not limited to (the wavy line indicates the site of covalent attachment to the linker):

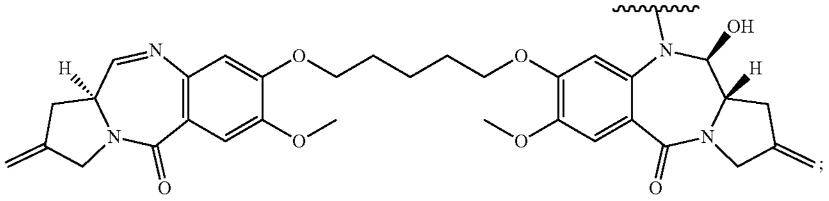
PBD dimer
Nonlimiting exemplary embodiments of ADCs comprising PBD dimers have the following structures:
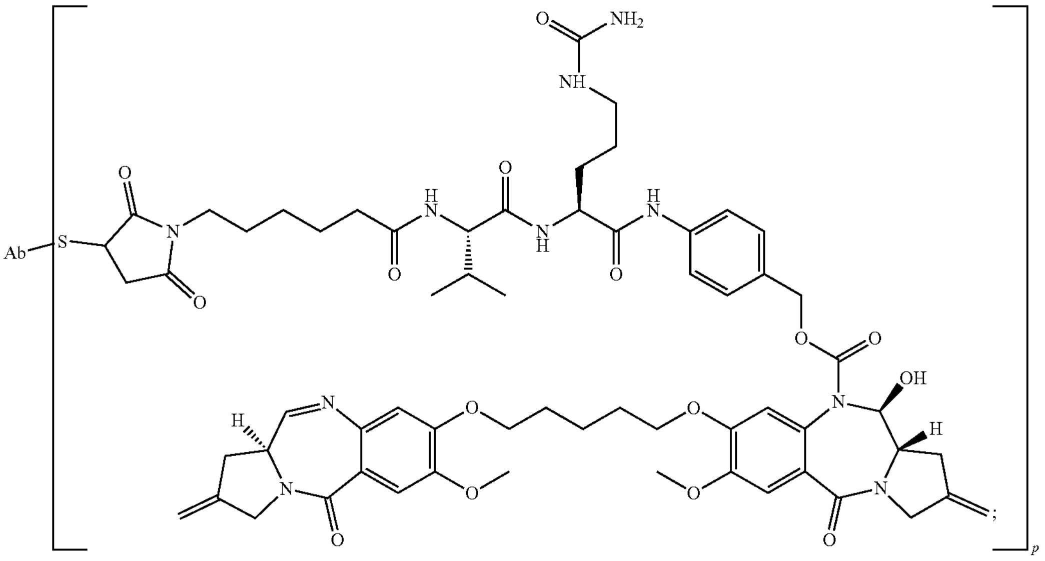
PBD dimer-val-cit-PAB-Ab
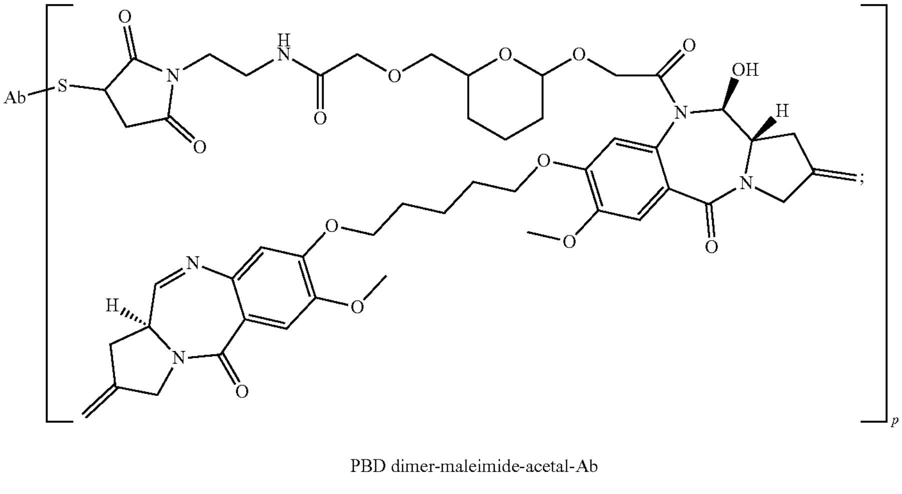
PBD dimer-maleimide-acetal-Ab -continued

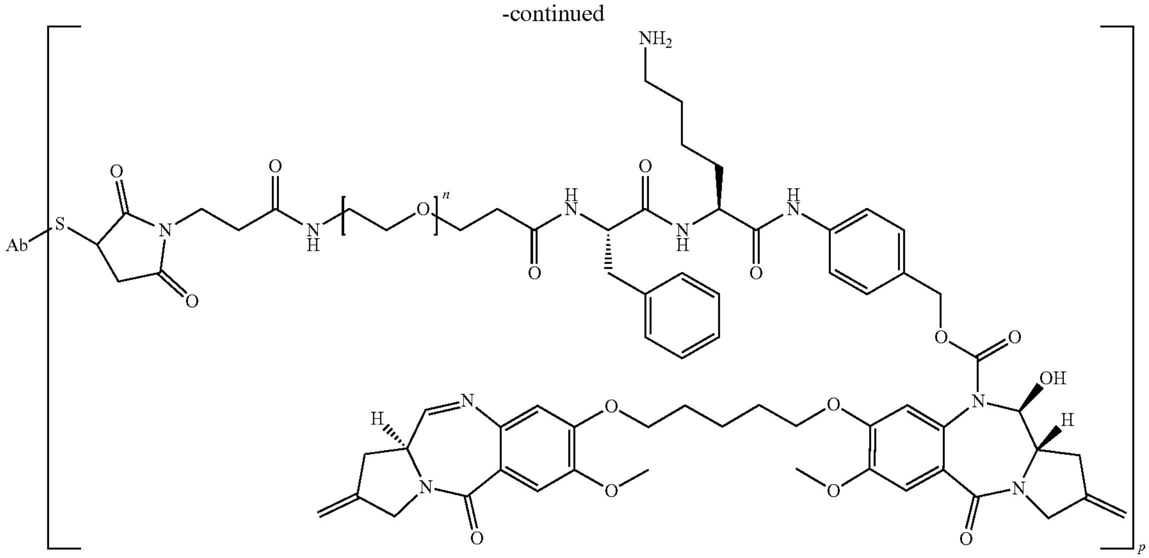

PBD dimer-Phe-homoLys-PAB-Ab, wherein: n is 0 to 12. In some embodiments, n is 2 to 10. In some embodiments, n is 4 to 8. In some embodiments, n is selected from 4, 5, 6, 7, and 8.

The linkers of PBD dimer-val-cit-PAB-Ab and the PBD dimer-Phe-homoLys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703), including phase II/III trials for hepatocellular carcinoma (Sun et al (2003) *Proceedings of the American Society for Clinical Oncology* 22, Abs1448; Quintieri (2003) *Proceedings of the American Association of Cancer Research,* 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

(Ia)

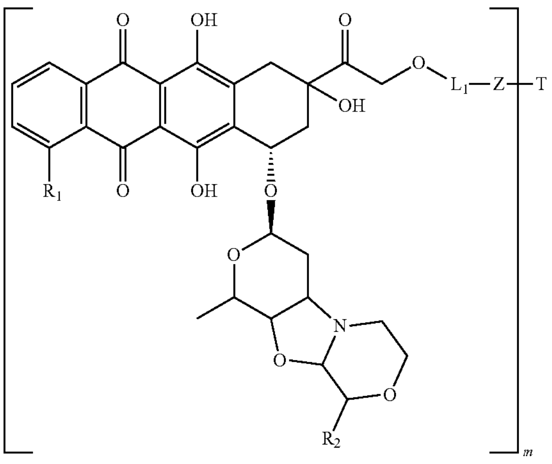

wherein $R_1$ is hydrogen atom, hydroxy or methoxy group and $R_2$ is a $C_1$-$C_8$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

(Ib)

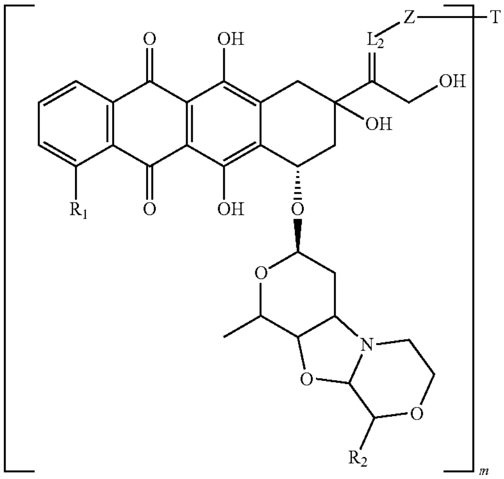

wherein $R_1$ is hydrogen atom, hydroxy or methoxy group and $R_2$ is a $C_1$-$C_8$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

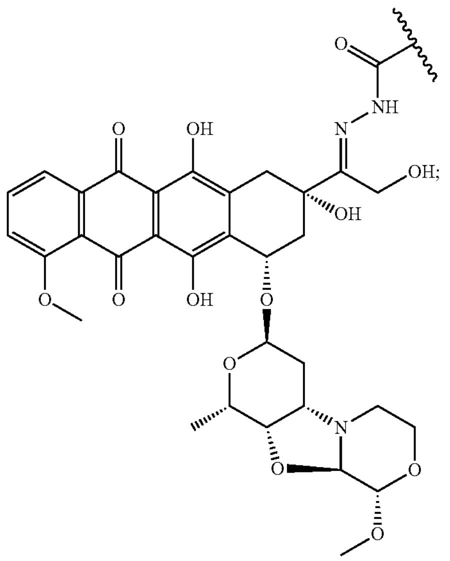

or

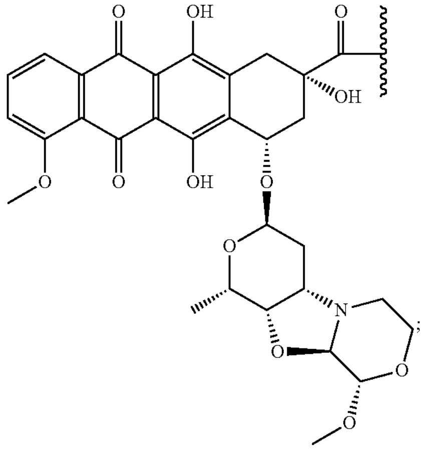

;

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

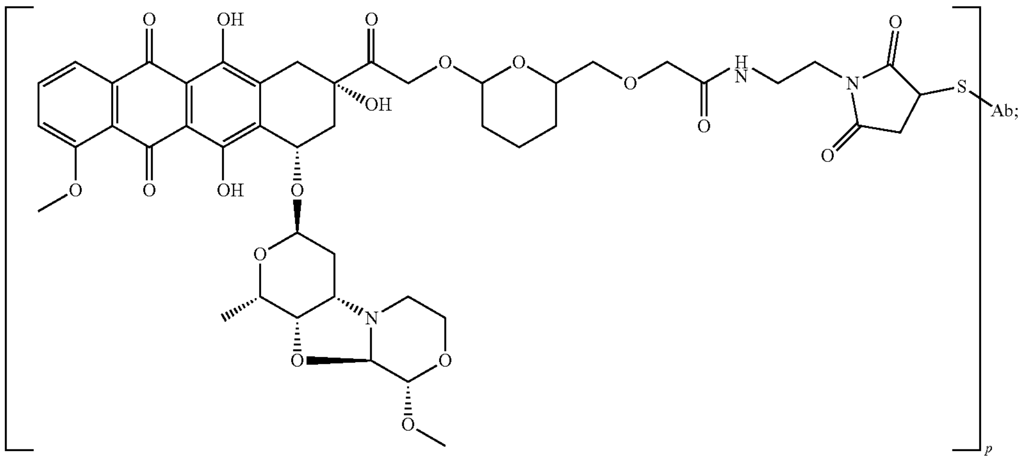
PNU-159682 maleimide acetal-Ab
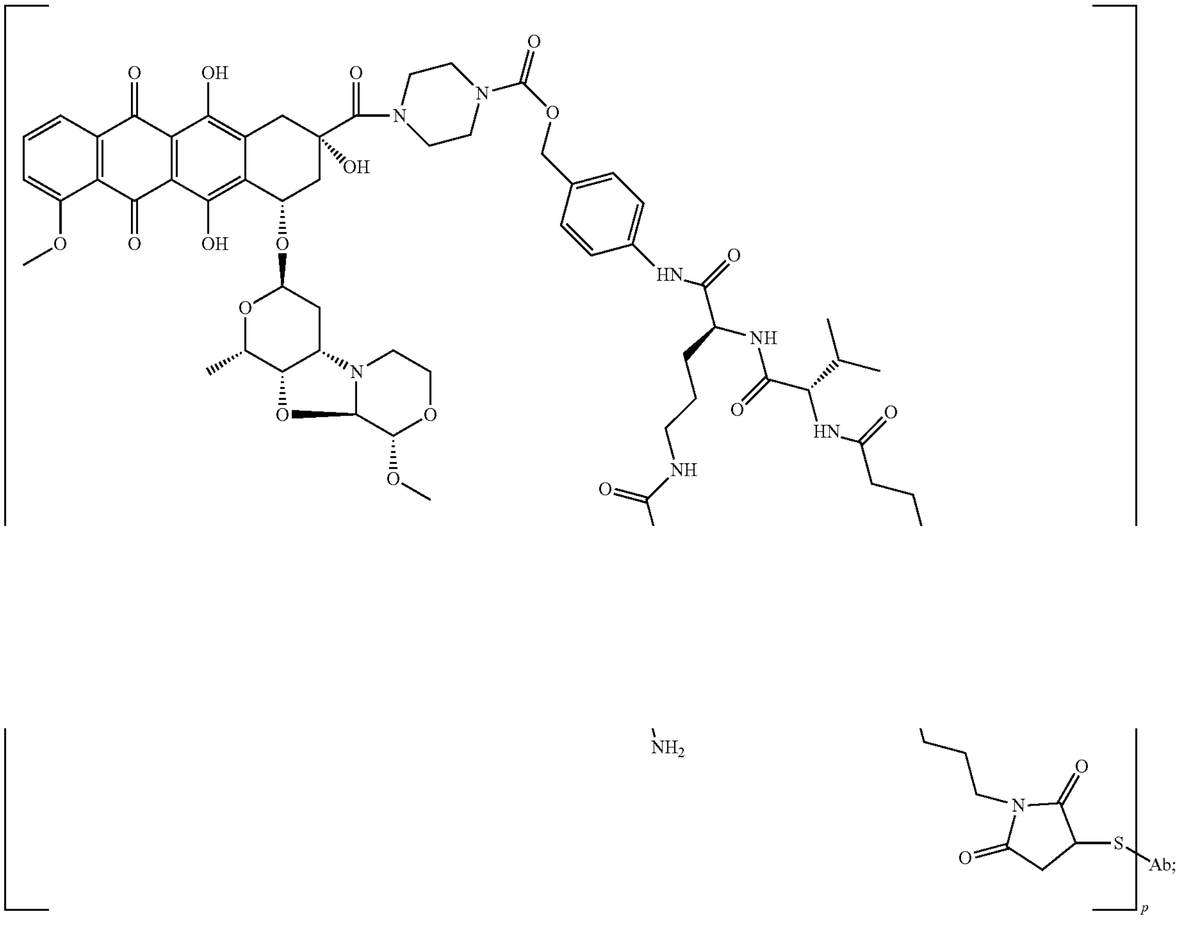
PNU-159682-val-cit-PAB-Ab -continued
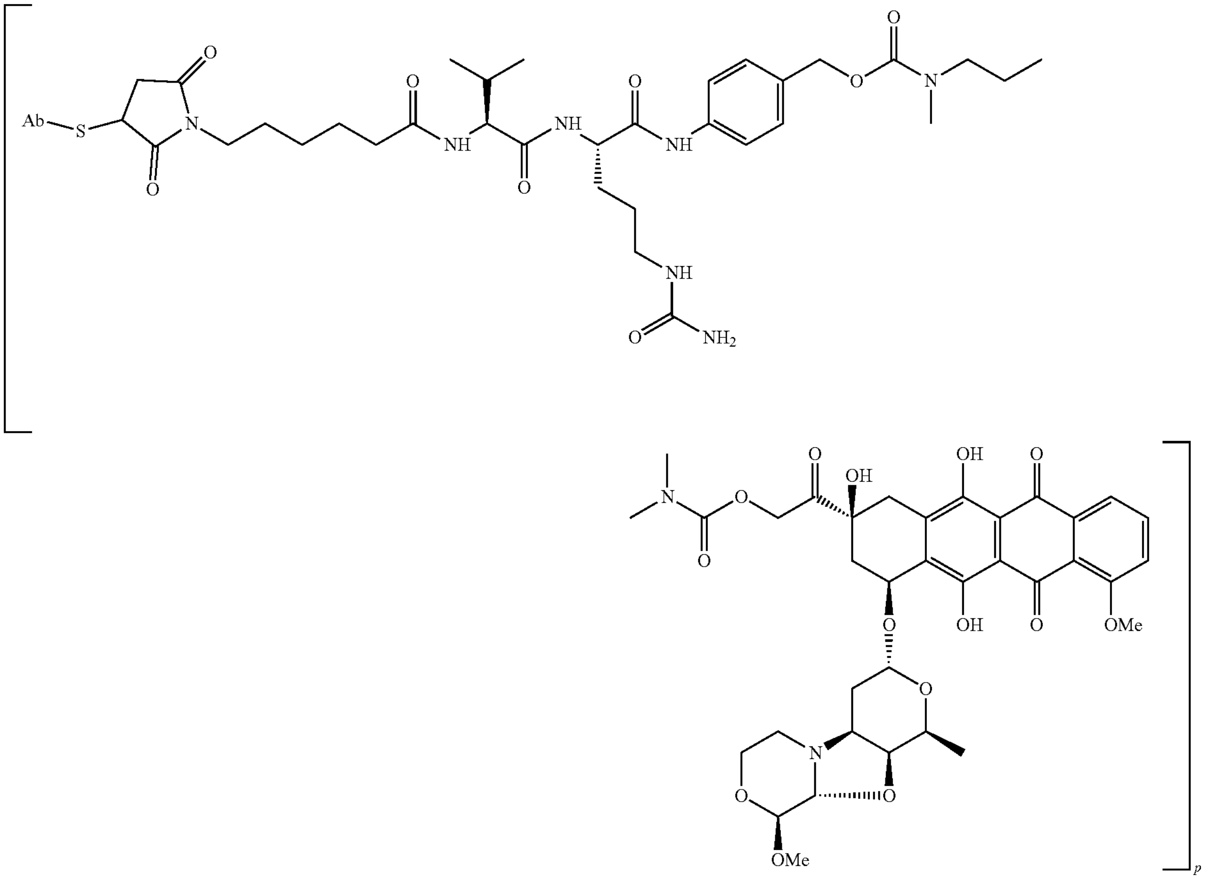
PNU-159682-val-cit-PAB-spacer-Ab
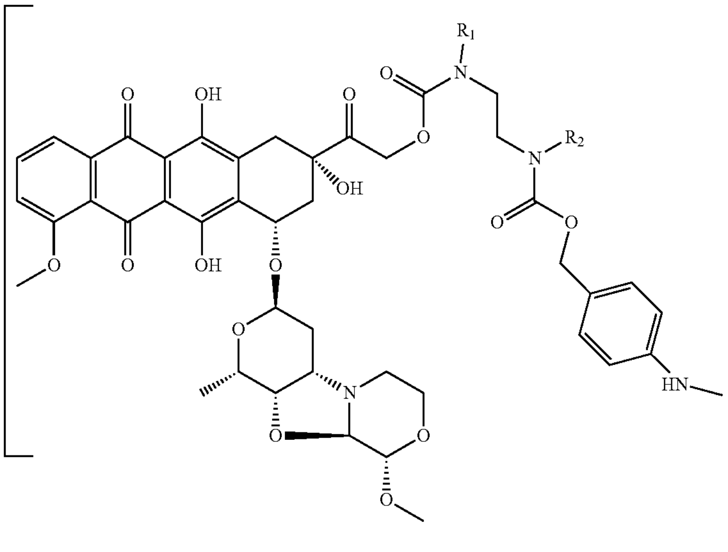

-continued

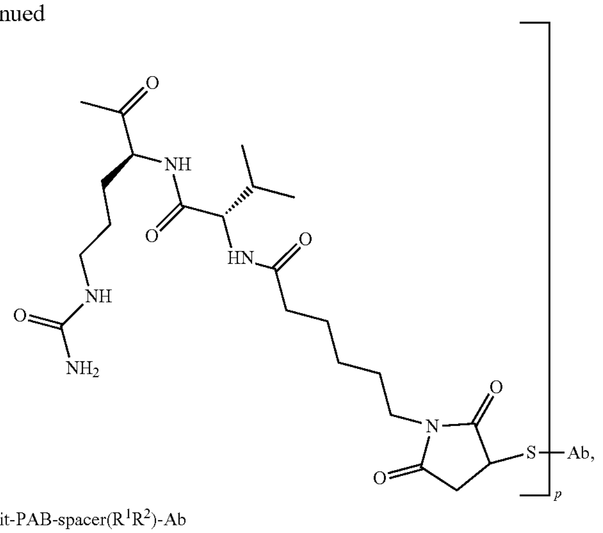

PNU-159682-val-cit-PAB-spacer($R^1R^2$)-Ab $R_1$ and $R_2$ are independently selected from H and $C_1$-$C_6$ alkyl; and

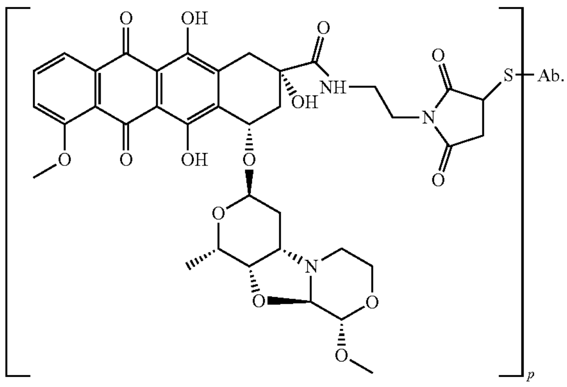

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer($R^1R^2$)-Ab are protease cleavable.

(6) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{21}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, March 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates provided herein may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled “Exemplary Linkers.” Methods of using such cross-linker reagents to link two moieties, including a proteinaceous moiety and a chemical moiety are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a “receptor” (such as streptavidin) for utilization in tumor pre-targeting wherein the antibody-receptor conjugate is administered to the patient, followed by removal of unbound conjugate from the circulation using a clearing agent and then administration of a “ligand” (e.g., avidin) which is conjugated to a cytotoxic agent (e.g., a drug or radionucleotide).

E. Methods and Compositions for Diagnostics and Detection

In certain embodiments, any of the anti-FcRH5 antibodies provided herein is useful for detecting the presence of FcRH5 (e.g., FcRH5) in a biological sample. The term “detecting” as used herein encompasses quantitative or qualitative detection. In certain embodiments, a biological sample comprises a cell or tissue. In certain embodiments, such tissues include normal and/or cancerous tissues that express FcRH5 at higher levels relative to other tissues, for example, B-cells and/or B-cell associated tissues. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In one aspect, provided herein are methods of detecting the presence of FcRH5 in a biological sample. In certain embodiments, the method comprises contacting the biological sample with an anti-FcRH5 antibody under conditions permissive for binding of the anti-FcRH5 antibody to FcRH5, and detecting whether a complex is formed between the anti-FcRH5 antibody and FcRH5. In one aspect, the invention provides a method of diagnosing a disorder associated with increased expression of FcRH5. In certain embodiments, the method comprises contacting a test cell with an anti-FcRH5 antibody; determining the level of expression (either quantitatively or qualitatively) of FcRH5 by the test cell by detecting binding of the anti-FcRH5 antibody to FcRH5; and comparing the level of expression of FcRH5 by the test cell with the level of expression of FcRH5 by a control cell (e.g., a normal cell of the same tissue origin as the test cell or a cell that expresses FcRH5 at levels comparable to such a normal cell), wherein a higher level of expression of FcRH5 by the test cell as compared to the control cell indicates the presence of a disorder associated with increased expression of FcRH5. In certain embodiments, the test cell is obtained from an individual suspected of having a disorder associated with increased expression of FcRH5. In certain embodiments, the disorder is a cell proliferative disorder, such as a cancer or a tumor. In some embodiments, the FcRH5 is FcRH5c. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

Exemplary cell proliferative disorders that may be diagnosed using an antibody described herein include a B-cell disorder and/or a B-cell proliferative disorder including, but not limited to, lymphoma, multiple myeloma non-Hodgkin’s lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and mantle cell lymphoma.

In one embodiment, an anti-FcRH5 antibody for use in a method of diagnosis or detection is provided. In a further aspect, a method of detecting the presence of FcRH5 in a biological sample is provided. In certain embodiments, the method comprises contacting the biological sample with an anti-FcRH5 antibody as described herein under conditions permissive for binding of the anti-FcRH5 antibody to FcRH5, and detecting whether a complex is formed between the anti-FcRH5 antibody and FcRH5 in the biological sample. Such method may be an in vitro or in vivo method. In one embodiment, an anti-FcRH5 antibody is used to select subjects eligible for therapy with an anti-FcRH5 antibody, e.g. where FcRH5 is a biomarker for selection of patients. In a further embodiment, the biological sample is a cell or tissue (e.g., biopsy material). In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In a further embodiment, an anti-FcRH5 antibody is used in vivo to detect, e.g., by in vivo imaging, an FcRH5-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The*

*Oncologist* 12:1379-1389 (2007) and Verel et al., *J Nucl. Med.* 44:1271-1281 (2003). In such embodiments, a method is provided for detecting an FcRH5-positive cancer in a subject, the method comprising administering a labeled anti-FcRH5 antibody to a subject having or suspected of having an FcRH5-positive cancer, and detecting the labeled anti-FcRH5 antibody in the subject, wherein detection of the labeled anti-FcRH5 antibody indicates an FcRH5-positive cancer in the subject. In certain of such embodiments, the labeled anti-FcRH5 antibody comprises an anti-FcRH5 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In further embodiments, a method of diagnosis or detection comprises contacting a first anti-FcRH5 antibody immobilized to a substrate with a biological sample to be tested for the presence of FcRH5, exposing the substrate to a second anti-FcRH5 antibody, and detecting whether the second anti-FcRH5 is bound to a complex between the first anti-FcRH5 antibody and FcRH5 in the biological sample. A substrate may be any supportive medium, e.g., glass, metal, ceramic, polymeric beads, slides, chips, and other substrates. In certain embodiments, a biological sample comprises a cell, blood, or tissue (e.g., biopsy material)

Exemplary disorders that may be diagnosed or detected according to any of the above embodiments include FcRH5-positive cancers, such as FcRH5-positive B-cell proliferative disease, FcRH5-positive plasma cell neoplasm, and FcRH5-positive multiple myeloma. In some embodiments, an FcRH5-positive cancer is detected by anti-FcRH5 immunohistochemistry (IHC) or in situ hybridization (ISH). In some embodiments, an FcRH5-positive cancer is a cancer that expresses FcRH5 according to a reverse-transcriptase PCR (RT-PCR) assay that detects FcRH5 mRNA. In some embodiments, the RT-PCR is quantitative RT-PCR.

In certain embodiments, labeled anti-FcRH5 antibodies are provided. In some embodiments, the anti-FcRH5 antibody binds an isoform c-specific region of the extracellular domain of FcRH5c. In some embodiments, the anti-FcRH5 antibodies binds Ig-like domain 9 of FcRH5c. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$, $^{3}$H, and $^{131}$I, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-FcRH5 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions.

Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody and/or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-FcRH5 antibodies (e.g., FcRH5 bispecific antibodies) and/or immunoconjugates provided herein may be used in methods, e.g., therapeutic methods. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In one aspect, an anti-FcRH5 antibody (e.g., FcRH5 bispecific antibody) and/or immunoconjugate provided herein is used in a method of inhibiting proliferation of an FcRH5-positive cell, the method comprising exposing the cell to the anti-FcRH5 antibody (e.g., FcRH5 bispecific antibody) and/or immunoconjugate under conditions permissive for binding of the anti-FcRH5 antibody (e.g., FcRH5 bispecific antibody) and/or immunoconjugate to FcRH5 (e.g., FcRH5c) on the surface of the cell, thereby inhibiting the proliferation of the cell. In certain embodiments, the method is an in vitro or an in vivo method. In further embodiments, the cell is a B-cell proliferative disorder. In certain embodiments, the cell proliferative disorder is associated with increased expression and/or activity of FcRH5 (e.g., FcRH5c). For example, in certain embodiments, the B-cell proliferative disorder is associated with increased expression of FcRH5 on the surface of a B-cell. In certain embodiments, the B-cell proliferative disorder is a tumor or a cancer. In some embodiments, the B-cell proliferative disorder is a plasma cell neoplasm. In some embodiments, the plasma cell neoplasm is multiple myeloma, plasmacytoma, and/or MGUS. Examples of B-cell proliferative disorders to be treated by the antibodies and/or immunoconjugates of the invention include, but are not limited to, lymphoma, multiple myelomanon-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), and/or mantle cell lymphoma.

Presence of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like, RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

Inhibition of cell proliferation in vitro may be assayed using the CellTiter-Glo™ Luminescent Cell Viability Assay, which is commercially available from Promega (Madison, WI). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *Anti Cancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-FcRH5 antibody (e.g., FcRH5 bispecific antibody) and/or immunoconjugate for use as a medicament is provided. In further aspects, an anti-FcRH5 antibody (e.g., FcRH5 bispecific antibody) and/or immunoconjugate for use in a method of treatment is provided. In certain embodiments, an anti-FcRH5 antibody (e.g., FcRH5 bispecific antibody) and/or immunoconjugate for use in treating FcRH5 (e.g., FcRH5c)-positive cancer is provided. In certain embodiments, provided herein the anti-FcRH5 antibody (including FcRH5 bispecific antibody) and/or immunoconjugate for use in a method of treating an individual having an FcRH5 (e.g., FcRH5c)-positive cancer, the method comprising administering to the individual an effective amount of the anti-FcRH5 antibody and/or immunoconjugate. In some embodiments, the anti-FcRH5 antibody binds an isoform c-specific region of the extracellular domain of FcRH5c. In some embodiments, the anti-FcRH5 antibodies binds Ig-like domain 9 of FcRH5c. In one such embodiment, the method further comprises administering to the individual an effective amount of at least one additional therapeutic agent, e.g., as described below.

In a further aspect, provided herein are uses of an anti-FcRH5 antibody (e.g., FcRH5 bispecific antibody) and/or immunoconjugate in the manufacture or preparation of a medicament. In one embodiment, the medicament is for treatment of FcRH5 (e.g., FcRH5c)-positive cancer. In a further embodiment, the medicament is for use in a method of treating FcRH5 (e.g., FcRH5c)-positive cancer, the method comprising administering to an individual having FcRH5 (e.g., FcRH5c)-positive cancer an effective amount of the medicament. In one such embodiment, the method further comprises administering to the individual an effective amount of at least one additional therapeutic agent, e.g., as described below. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

In a further aspect, provided herein are methods for treating FcRH5 (e.g., FcRH5c)-positive cancer. In one embodiment, the method comprises administering to an individual having such FcRH5 (e.g., FcRH5c)-positive cancer an effective amount of an anti-FcRH5 antibody (e.g., FcRH5 bispecific antibody) and/or immunoconjugate. In one such embodiment, the method further comprises administering to the individual an effective amount of at least one additional therapeutic agent, as described below. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

An FcRH5-positive cancer according to any of the above embodiments may be, e.g., FcRH5-positive B-cell proliferative disorder, FcRH5-positive plasma cell neoplasm, and/or FcRH5-positive multiple myeloma. In some embodiments, an FcRH5-positive cancer is detected by anti-FcRH5 immunohistochemistry (IHC) or in situ hybridization (ISH). In some embodiments, an FcRH5-positive cancer is a cancer that expresses FcRH5 according to a reverse-transcriptase PCR (RT-PCR) assay that detects FcRH5 mRNA. In some embodiments, the RT-PCR is quantitative RT-PCR.

In some embodiments of any of the above embodiments, the individual may be a human.

In a further aspect, provided herein are pharmaceutical formulations comprising any of the anti-FcRH5 antibodies and/or immunoconjugate provided herein, e.g., for use in any of the above therapeutic methods. In one embodiment, a pharmaceutical formulation comprises any of the anti-FcRH5 antibodies (e.g., bispecific antibodies) and/or immunoconjugates provided herein and a pharmaceutically acceptable carrier. In another embodiment, a pharmaceutical formulation comprises any of the anti-FcRH5 antibodies (e.g., bispecific antibodies) and/or immunoconjugates provided herein and at least one additional therapeutic agent, e.g., as described below.

Antibodies (e.g., bispecific antibodies) and/or immunoconjugates provided herein can be used either alone or in combination with other agents in a therapy. Such combination therapies noted above encompass combined administration (where two or more therapeutic agents are included in the same or separate formulations), and separate administration, in which case, administration of the antibody or immunoconjugate provided herein can occur prior to, simultaneously, and/or following, administration of the additional therapeutic agent and/or adjuvant. Antibodies and/or immunoconjugates provided herein can also be used in combination with radiation therapy.

An antibody (including bispecific antibody) and/or immunoconjugate provided herein (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies (e.g., bispecific antibodies) and/or immunoconjugates provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody (e.g., bispecific antibodies) and/or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody (e.g., bispecific antibody) and/or immunoconjugate provided herein (when used alone or in combination with one or more other additional therapeutic agents) will depend on the type of disease to be treated, the type of antibody or immunoconjugate, the severity and course of the disease, whether the antibody (e.g., bispecific antibody) and/or immunoconjugate is administered for preventive or therapeutic purposes, previous therapy, the patient's clinical history and response to the antibody or immunoconjugate, and the discretion of the attending physician. The antibody (e.g., bispecific antibody) and/or immunoconjugate are suitably administered to the patient at one time or over a series of treatments. Depending on the type and severity of the disease, about 1 μg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody (e.g., bispecific antibody) and/or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate provided herein and an anti-FcRH5 antibody. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

H. Articles of Manufacture

In another aspect provided herein, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate provided herein. The label or package insert indicates that the composition is used for treating the condition of choice.

Moreover, the article of manufacture may comprise (a) a first container with a composition contained therein, wherein the composition comprises an FcRH5 antibody (e.g., bispecific antibody) and/or FcRH5 immunoconjugate provided herein; and (b) a second container with a composition contained therein, wherein the composition comprises a further cytotoxic or otherwise therapeutic agent. The article of manufacture in this embodiment provided herein may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes. In some embodiments, the anti-FcRH5 antibody binds an isoform c-specific region of the extracellular domain of FcRH5c. In some embodiments, the anti-FcRH5 antibodies binds Ig-like domain 9 of FcRH5c.

III. Examples

The following are examples of methods and compositions of the invention. It is understood that various other embodiments may be practiced, given the general description provided above.

Materials and Methods

Immunogen (E11-Flag)

Amino acids 745-850 of human FcRH5c (SEQ ID NO:1) were cloned into mammalian expression vector pRK5.NT.Flag using standard protocols and expressed transiently in CHO cells. The recombinant protein with N-terminal Flag-expression tag was purified using anti-flag and size exclusion chromatography on an S200 Superdex column.

Development and Characterization of Mouse Anti-FcRH5 E11 Antibodies

Balb/c mice (Charles River, Hollister, CA) were immunized with 2 μg human FcRH5 E11 ECD protein (amino acid residues 743-850 of SEQ ID NO: 1) (Genentech, South San Francisco, CA) mixed with MPL+TDM (Ribi) adjuvant via footpad injection. Mice received nine doses, followed by a prefusion boost in PBS alone via footpad and IV routes three days prior to fusion.

Popliteal lymph nodes were harvested and lymphocytes from these mice, all of whose sera demonstrated strong binding titers to the immunization protein by ELISA and showed strong FACS reactivity to SVT2 cells transfected with the human FcRH5 E11 ECD, were fused with X63-Ag8.653 mouse myeloma cells (American Type Culture Collection, Rockville, MD) via electrofusion (Harvard Apparatus, Holliston, MA). Fused cells were incubated at 37° C., 7% $CO_2$, overnight in Medium C (StemCell Technologies, Vancouver, BC, Canada), before resuspension in semi-solid Medium D (StemCell Technologies) containing 0.01 mg/ml FITC labeled anti-mouse IgG (Jackson ImmunoResearch, West Grove, PA) and plating into Omniwell trays (Thermo Fisher Scientific, Rochester, NY). Nine days after plating, fluorescent colonies were selected and transferred into 96-well plates containing Medium E (StemCell Technologies) using a Clonepix FL (Genetix, New Milton, Hampshire, UK). Supernatants were screened by ELISA against anti-mouse IgG (MP Biomedicals, Santa Ana, CA) seven days after picking.

Hybridomas demonstrating mouse IgG expression by ELISA were expanded and screened by FACS against SVT2 cells overexpressing full-length human FcRH5, cyno FcRH5, and human FcRH5 E11 ECD. Strong FACS positive clones were subcloned by single-cell sorting using a FACSAria (BD, Franklin Lakes, NJ). Final clones demonstrating the highest ELISA and FACS binding of interest after one or two rounds of subcloning were expanded for large-scale production in bioreactors (Integra Biosciences, Chur, Switzerland). Supernatants were then purified by Protein A affinity chromatography as previously described (Hongo et al. 2000).

Production of bisFabs

BisFabs were generated by crosslinking a Fab' of the anti-FcRH5 Mab to a Fab' of the anti-CD3 (UCHT1.v9) Mab at the hinge cysteine residues. To generate the Fab' 2 fragments from the hybridoma Abs different digestion conditions were used: Abs of the mIgG1 isotype were digested with 1:50 (w/w) pepsin at pH 3.5 for 1-2 H at 37° C.; mouse IgG2a Abs were digested with Lysin C endopeptidase at 1 1:500 (w/w) ratio, pH 8, for 2-4 h at 37° C.; and mouse IgG2b Abs were digested with Lysin C at a 1:100 (w/w) ratio overnight at 37° C. In all cases the $F(ab')_2$ fragment was isolated from the reaction mixture by capture with a SP column and elution with 10 column volumes of a lineal gradient (0-100%) of 1M sodium chloride. Under the digestion conditions mentioned above mIgG1 and mIgG2b produced a $F(ab')_2$ fragment containing three Cysteine residues in the hinge, while the $F(ab')_2$ from mIgG2a showed two cysteine residues in the hinge. To generate Fab' with a single reactive Cys two different methods were used. For fragments containing an odd (3) number of hinge cysteines (mIgG1 and mIgG2b) the isolated $F(ab')_2$s were reduced in 25 mM sodium acetate, pH 5, 150 mM sodium chloride, 2 mM EDTA, 2 mM TCEP for 2-6-H at RT. After the reduction step was complete, the sample was diluted to 0.2 mg/ml, the pH was raised to 7.5 by adding Tris pH 8 and 5 mM dehydroascorbic acid (DHAA) was added to drive re-oxidation of the cysteines. After an overnight incubation at room temperature the presence of reduced Thiols was evaluated by probing with an excess of NEM and analyzing the MW shift by mass spectrometry. After confirming the presence of only one reactive Cysteine per molecule, the Fab' was purified by gel filtration to remove small amounts of homodimers.

For $F(ab')_2$ fragments derived from mIgG2a and containing 2 Cysteine residues in the hinge, a single reactive Cysteine was produced by partial blocking with N-ethyl maleimide (NEM) as described in Scheer et al (in press). Briefly, the antibody was digested with pepsin (1% w/w) by treatment in sodium acetate buffer at pH 4.5. After digestion for 1 hour, the $F(ab')_2$ was isolated from the digestion mixture by capture on an SP-HP cation exchange resin and purified by a 10 CV salt gradient of 0-1 M NaCl. The $F(ab')_2$ was then reduced with 1 mM TCEP in a buffer containing 25 mm MES, pH 5.8, 2 mM EDTA, and 300 mM NaCl and the Fabs were oxidized by the addition of 5 mM dehydroacorbic acid (DHAA) to reform the disulfide bond between the heavy chain and light chain.

The effector arm of the bisfabs (UCHT1.v9) was generated by pepsin digestion, partial NEM blocking and conjugation to bismaleimide as described before (Scheer et al; in press). Briefly, the two thiols (cys residues) at the hinge were then reacted with 1 equivalent of N-ethylmaleimide (NEM) (Sigma Aldrich). The different anti-FCRH5 Fab's containing a single reactive Cysteine were incubated with the anti-CD3 Fab' conjugated to the bismaleimide crosslinker overnight at room temperature. The ~100 kDa crosslinked Fabs were separated from the unreacted species by gel filtration and then characterized by SDS-PAGE, mass spectrometry and analytical size exclusion chromatography.

TDB Expression and Purification

TDBs were produced by two different approaches: co-culture of bacteria expressing each of the two antibody arms or by expressing each arm separately and then anneling them in vitro. The strategies have been described in Christoph Spiess et al. 2012 and described in PCT/US10/58958 filed on 31 May 2011, which is incorporated by reference. Briefly for the coculture strategy *E. coli* expressing anti-CD3 (hole) and *E coli* expressing anti-tumor target (knob) were grown together in shaker flasks at a predetermined ratio such that it produced similar amounts of each hemimer. The cocultured bacterial broth was then harvested, the cells disrupted in a microfluidizer and the antibodies purified by Protein A affinity. It has been observed that during microfluidizing and protein A capture the two arms annealed and formed the hing inter-chain disulfide bridges (Christoph Spiess et al. 2012). Alternatively, the antibody hemimers were grown separately by high-cell density fermentation and independently isolated by Protein A chromatography. The purified hemimers were than combined at a 1:1 molar ration and incubated in 50 mM Tris, pH 8.5 in the presence of 2 mM DTT for 4 hours to allow annealing and the reduction of disulfides in the hing region. Dialysis against the same buffer without DTT for 24-48 hours resulted in the formation of the inter-chain disulfide bonds. For both production strategies the bispecific antibody was purified from contaminants by hydrophobic interaction chromatography (HIC) as described in Christoph Spiess et al. 2012. The resulting material was analyzed for endotoxin levels using an Endosafe protable etest system and when needed, the endotoxin content was reduced by washing the protein with 0.1% Triton X-114.

TDB Characterization

The molecular weight of the bispecific antibody was analyzed by mass spectrometry (LC-ESI/TCF) as described before (Jackman et al. 2010). The antibodies were also analyzed by analytical size exclusion chromatography in Zenix SEC-300 column (Sepax Technologies USA) using an Agilent 1:100 HPLC system. The presence of residual antibody fragments was quantified by electrophoresis using a 2100 Bioanalyzer and a Protein 230 Chip.

Blood Cell Fractionation

PBMCs were separated from the blood of healthy volunteers using lymphocyte separation medium (MP biomedicals, Solon, OH). CD8+ cells were extracted from PBMC using human CD8+ Isolation Kit from Miltenyi (#130-094-156) by negative selection.

In Vitro Cytotoxicity Assays (T Cell Killing)

For in vitro cytotoxicity assays $1\times10^4$ target cells were plated on 96 well plates and incubated overnight. $3\times10^4$ CD8+ T-cells were added with or without TDB or BisFab and incubated 48 hours in +37° C. T cells were removed by washing twice with growth media. Cell viability was measured using CellTiter-Glo® Luminescent Cell Viability Assay (Promega, Madison, WI).

Alternatively, in vitro cytotoxicity was monitored by flow cytometry. Target cells were labeled with carboxyfluorescein succinimidyl ester (CFSE) according to manufacturer's protocol (Invitrogen, #C34554). The CFSE-labeled target cells and purified CD8+ T cells from human PBMC were mixed in 3:1 E:T ratio and incubated with TDB or BisFab for 48 hours. At the end of the incubation, the cells were lifted by trypsin and collected from the plate. The cells were resuspended in equal volume of PBS+2% FBS+1 mM EDTA+propidium iodine (PI). Flow cytometry analysis was done on a FACSCalibur in automation format. The number of live target cells was counted by gating on CFSE+/PI negative cells. The percentage of cytotoxicity was calculated as follows: % cytotoxicity (live target cell number w/o TDB−live target cell number w/TDB)/(live target cell number w/o TDB)×100.

Analysis of T Cell Activation

Target cells and purified CD8+ T cells were mixed in the presence or absence of TDB and T cell activation was analyzed by flow cytometry. At the end of the incubation, cells were stained with CD8-FITC (BD Biosciences, 555634) and CD69-PE (BD Biosciences, 555531).

Binding of Subclone Supernatants, Monoclonal Antibodies, bisFabs and TDBs

To test binding to endogenously FcRH5 expressing cancer cells or FcRH5 transfected cancer cells, cells were lifted using EDTA/PBS. $1\times10^5$ cells were suspended in 100 ul and incubated h with primary antibodies (1 volume of non-IgG quantitated subclone supernatant, 4 ug/ml IgG quantified subclone supernatant or 2 ug/ul purified monoclonal antibodies). Cells were washed twice with FACS buffer (PBS 1% BSA 2 mM EDTA) and incubated with 1:1000 dilution of goat anti-mouse secondary labeled with PE or 1:100 of goat anti-mouse APC. Cells were washed twice with FACS buffer and Flow cytometry analysis was done on a FACSCalibur. Direct Xenon-labeling of antibodies was done according to manufacturer's protocol (Invitrogen), when indicated. To analyze binding to NK or B cells, 1 million human PBMC were incubated with 4 ug/ml IgG quantified subclone supernatants for 60 min, washed and incubated with 1:100 dilution of goat anti-mouse secondary labeled with APC. Cells were then washed again twice and stained using anti-CD56 (PE; BD Biosciences #555516) and anti-CD19 (PE; BD Biosciences #340364) prior flow cytometry and analysis of binding to human CD56+ and CD19+ cells.

Results

Initially to produce isoform specific antibodies for the membrane proximal Ig-domain, mice were immunized with recombinant baculovirus produced E11 protein (amino acids 745-848 of SEQ ID NO: 1) of human FcRH5c and C-terminal His-expression tag). This immunization strategy did not result to significant immune response to FcRH5 and failed to produce monoclonal anti-FcRH5 antibodies. The second immunization strategy was DNA-immunization with plasmid encoding amino acids 745-977 of FcRH5c (SEQ ID NO: 1) encoding membrane proximal Ig-domain, transmembrane domain and intracellular domains of human FcRH5. This immunization strategy did not result to significant immune response to FcRH5 and failed to produce monoclonal anti-FcRH5 antibodies. The third immunization strategy utilized peptides corresponding to membrane proximal Ig-domain of FcRH5, that were homologous to cyno FcRH5 and non-homologous to human FcRH1, FcRH2, FcRH3, and FcRH4. This immunization strategy did not result to significant immune response to FcRH5 and failed to produce monoclonal anti-FcRH5 antibodies.

For the fourth immunization strategy E11 protein was produced in CHO-cells consisting of the membrane proximal Ig-domain of human FcRH5 (amino acid residues 745-850 of SEQ ID NO: 1) with N-terminal Flag expression tag. The above recombinant protein was used to immunize mice. Immunization, development and characterization of mouse anti-FcRH5 E11 antibodies was performed as described in detail above.

After 6 doses of the recombinant E11 (amino acid residues 745-850 of SEQ ID NO: 1), serum was analyzed for FcRH5 binding antibodies using FACS. Significant reactivity was detected to SVT2 cells that express human full length FcRH5, cyno full length FcRH5, or the human E11 domain transmembrane domain and cytoplasmic domains but not vector transfected SVT2 cells indicating that FcRH5 reactive antibodies were present in the sera of all 5 immunized mice.

After 9 doses, lymphocytes from the immunized mice were electrofused with X63-Ag8.653 mouse myeloma cells. 323 IgG positive hybridoma subclones were selected for further screening. Clones were tested for binding to recombinant E11 protein (amino acid residues 745-850 of SEQ ID NO: 1) by ELISA (not shown) and binding to SVT2 cells that express human full length FcRH5, cyno full length FcRH5 or human E11 domain transmembrane domain and cytoplasmic domains of FcRH5 by FACS. A total of 26 clones were identified that bound to cells that express human FcRH5 and cells that express cyno FcRH5, indicative of cross-species reactivity (Table 2). Subclone supernatants were further characterized for binding to A) multiple myeloma cells transfected with human FcRH5, B) cells that express human FcRH5 endogenously (MOLP-2 myeloma cells, peripheral human CD19+ B-cells from healthy donors), C) SVT2 cells transfected to express human FcRH1, FcRH2, FcRH3 or FcRH4, D) 293 cells that express truncated version of human FcRH5 (lacking 4 Ig-domains including E11; amino acids 464-850 of SEQ ID NO: 1) and E) NK-cells. In addition, binding of supernatants to soluble FcRH5a was analyzed by ELISA. Based on these analysis monoclonal antibodies were selected for purification.

TABLE 2

| Sample | SVT2-huFcRH5 | SVT2-cyFcRH5 | SVT2-huE11 |
|---|---|---|---|
| 1B8 | +++ | ++ | ++ |
| 4H8 | +++ | ++ | ++ |
| 1H11 | +++ | ++ | + |
| 4G8 | ++ | + | + |
| 4D4 | + | + | + |
| 1C8 | +++ | ++ | + |
| 3C10 | +++ | ++ | ++ |
| 3A4 | +++ | ++ | ++ |
| 6D2 | +++ | +++ | + |
| 3G3 | ++ | + | +++ |
| 1F4 | ++ | + | + |
| 3F10 | ++ | + | +++ |
| 1G7 | +++ | ++ | ++ |
| 3B12 | ++ | + | +++ |
| 3G7 | +++ | ++ | + |
| 5A10 | +++ | ++ | ++ |
| 1C12 | ++ | + | + |
| 3D12 | ++ | + | ++ |
| 5H4 | ++ | ++ | + |
| 5H9 | ++ | ++ | +++ |
| 3C5 | ++ | ++ | + |
| 2D10 | + | + | +++ |
| 5B12 | ++ | + | ++ |
| 1H2 | + | + | + |
| 5F1 | ++ | ++ | ++ |
| 2H7 | ++ | +++ | ++ |

Figure 2A:
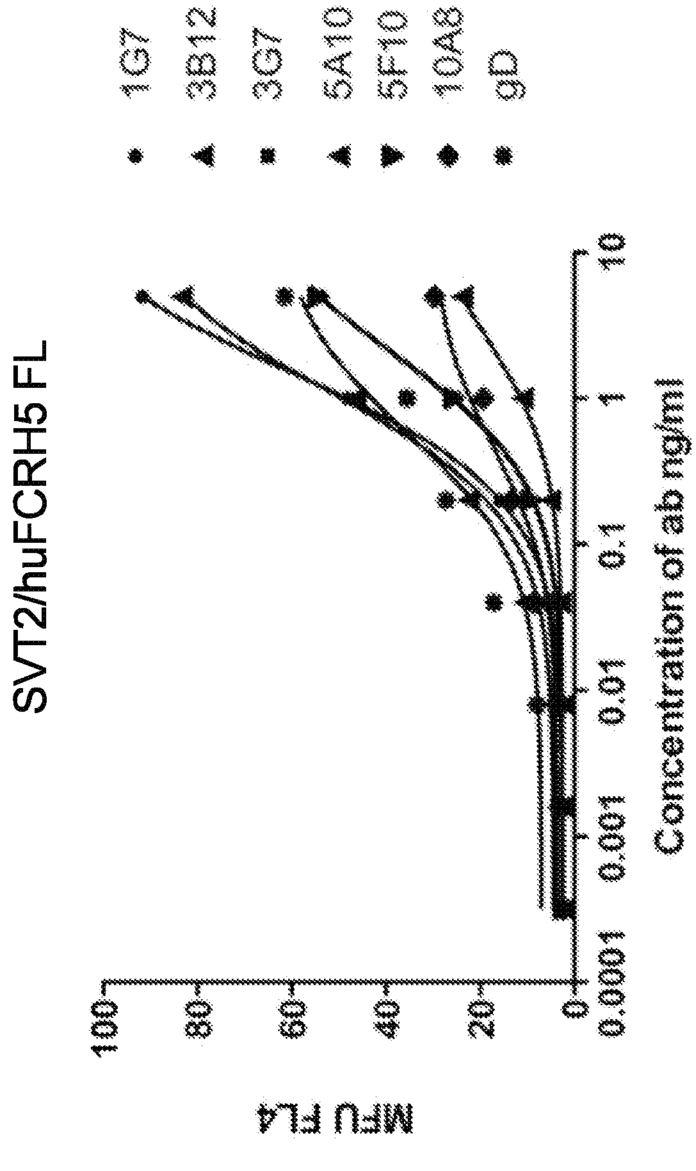
FIG. 2A shows binding of FcRH5 antibodies to SVT2 cells transfected with human FcRH5 in different concentrations.
Figure 2B:
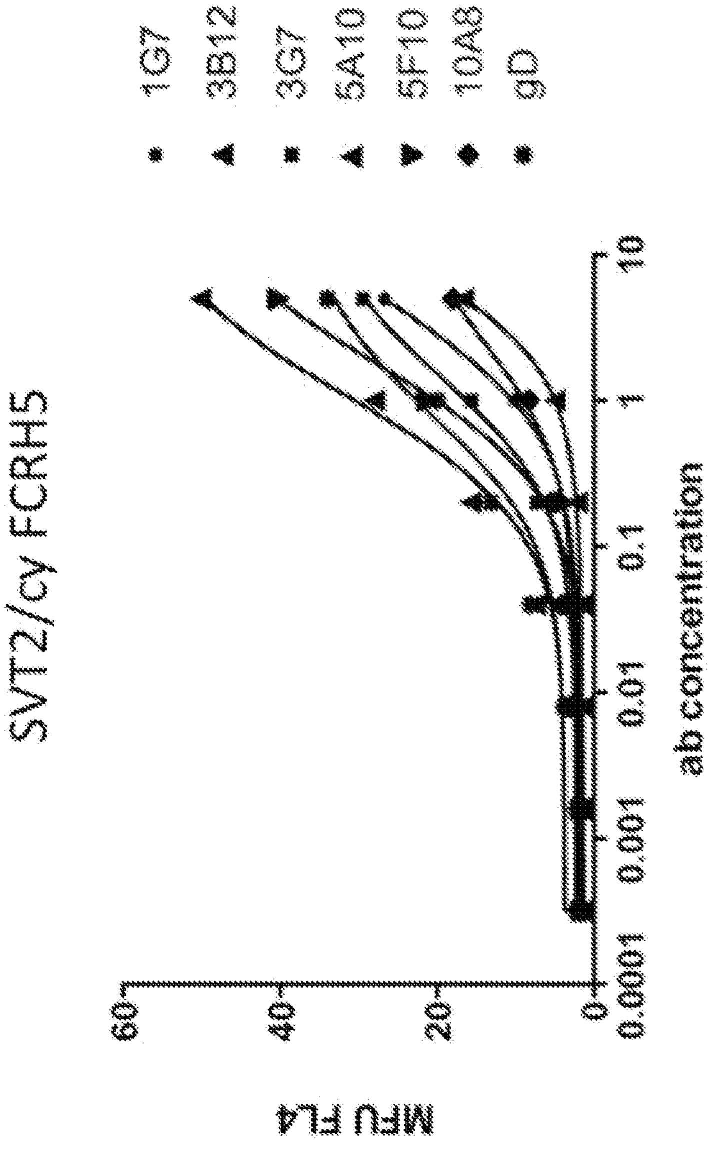
FIG. 2B shows binding of FcRH5 antibodies to SVT2 cells transfected with cyno FcRH5, in different concentrations.
Figure 3A:
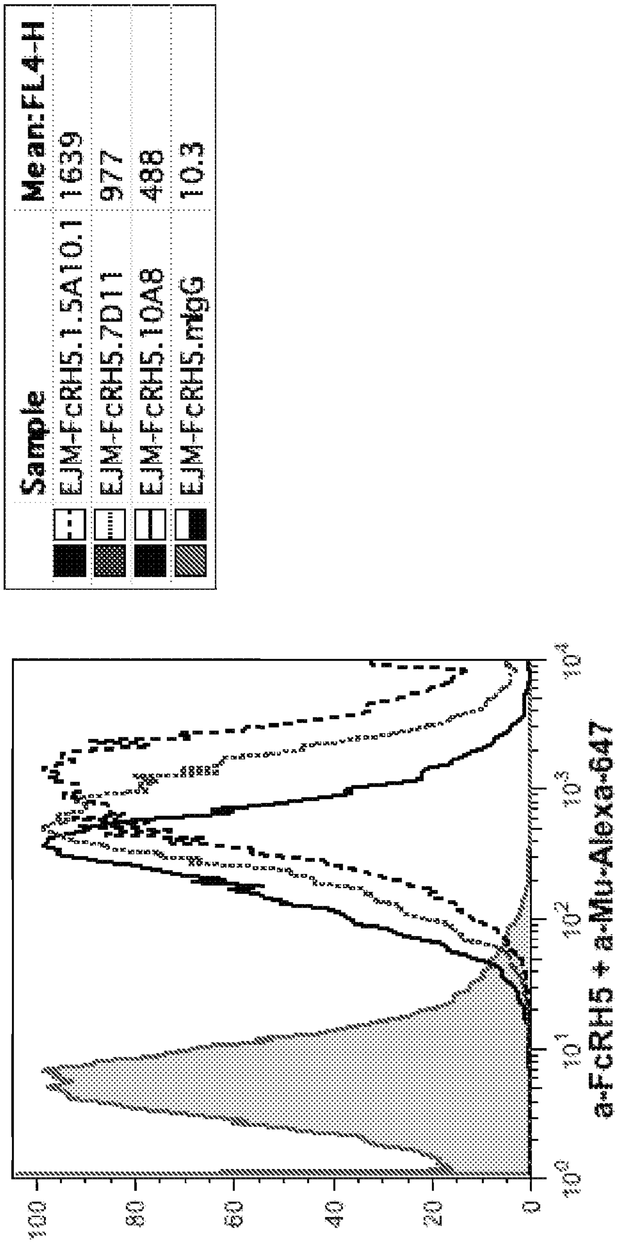
FIG. 3A shows binding of FcRH5 antibodies to EJM cells transfected with human FcRH5.
Figure 3B:
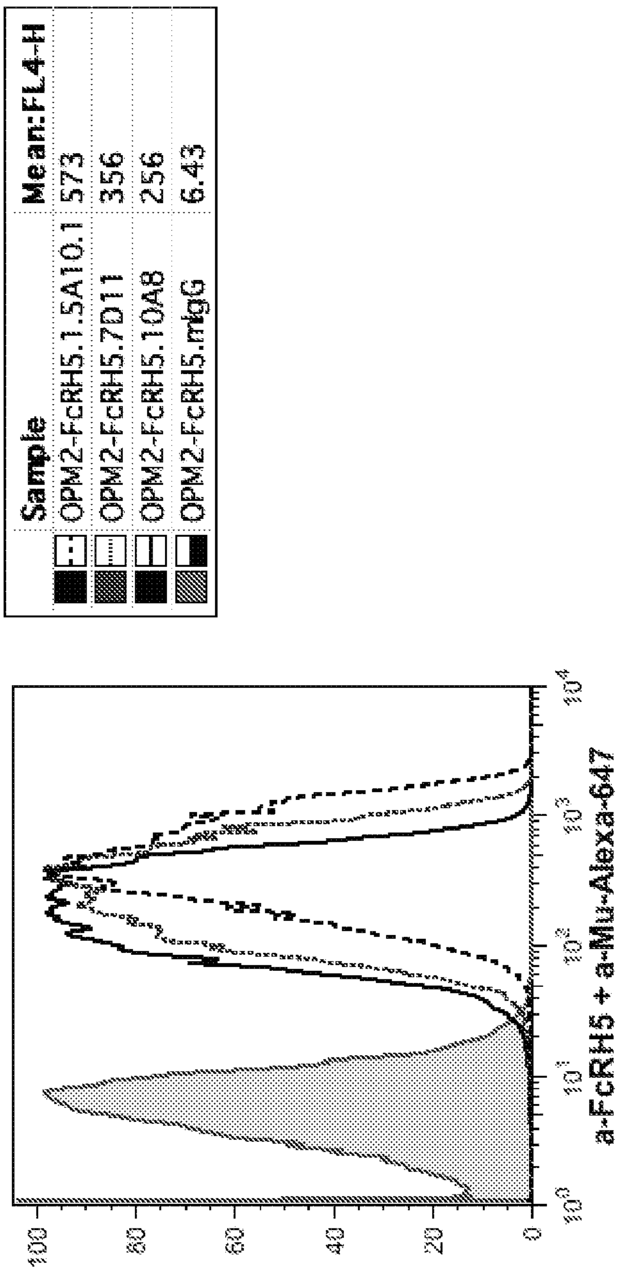
FIG. 3B shows binding of FcRH5 antibodies to OPM2 cells transfected with human FcRH5.
Figure 3C:
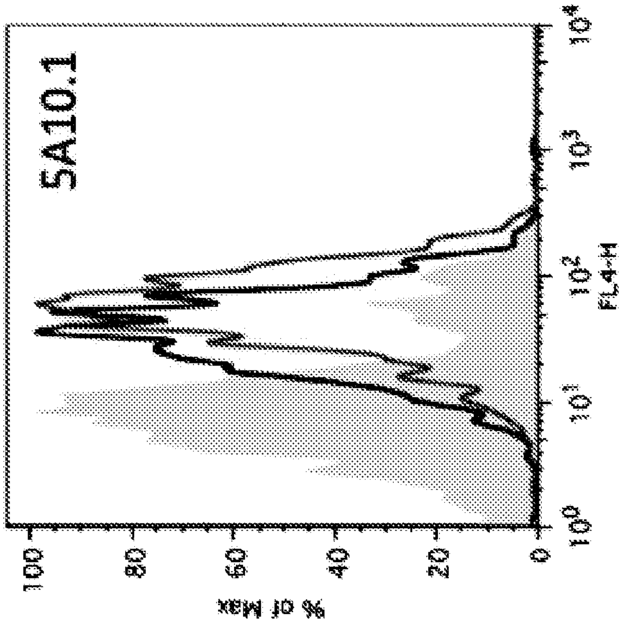
FIG. 3C shows binding of 5A10.1 subclone supernatants to MOLP2 cells which express FcRH5 endogenously.
Figure 3D:
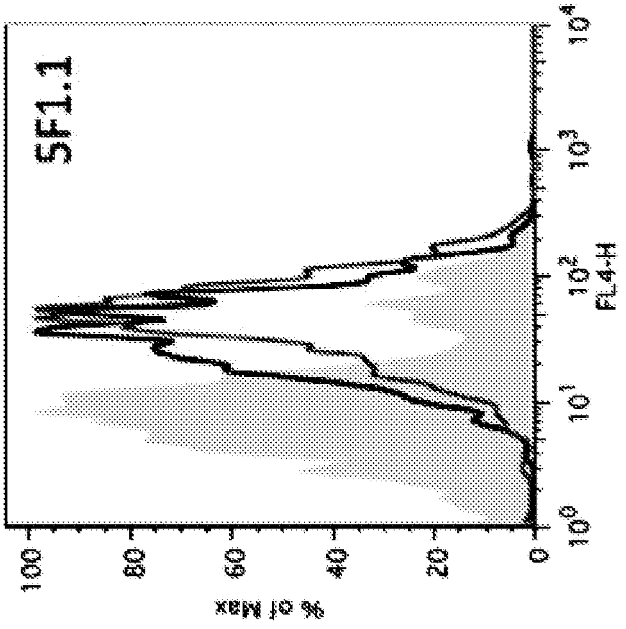
FIG. 3D shows binding of 5F1.1 subclone supernatants to MOLP2 cells which express FcRH5 endogenously.
Figure 3F:
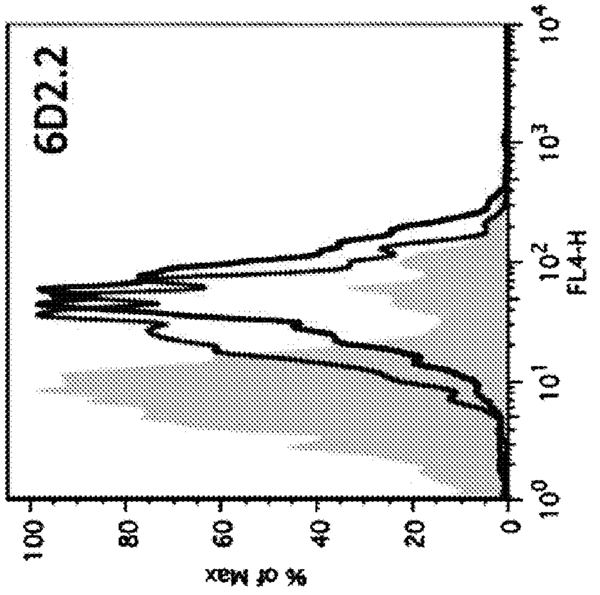
FIG. 3F shows binding of 6D2.2 subclone supernatants to MOLP2 cells which express FcRH5 endogenously.
Figure 3E:
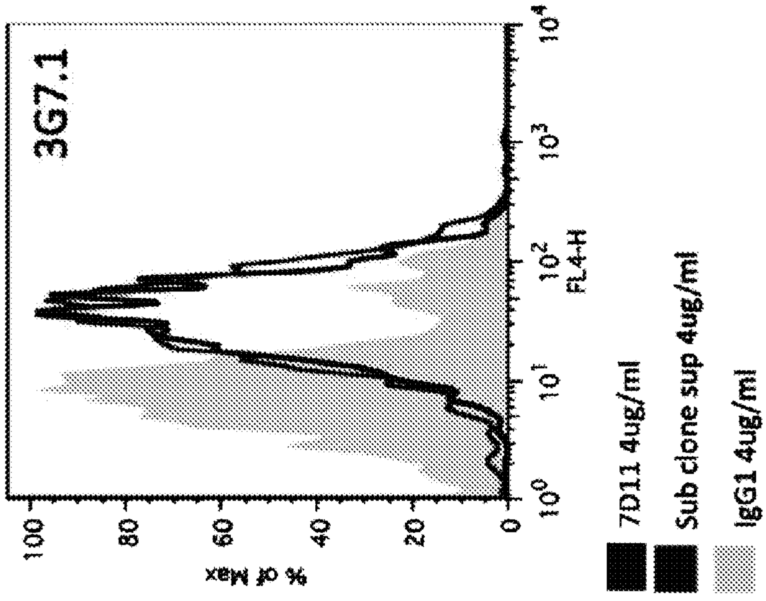
FIG. 3E shows binding of 3G7.1 subclone supernatants to MOLP2 cells which express FcRH5 endogenously.

FIG. 2 shows the dose-range of binding of five purified E11 antibodies, non-isoform selective anti-FcRH5 antibody 10A8 (which binds Ig-like domains 4-5 of FcRH5c) and a control antibody specific to the N-terminal gD-tag to the SVT2 cells expressing either human FcRH5 (FIG. 2A) or cyno FcRH5 (FIG. 2B). Antibodies in this assay were directly labeled with APC-fluorophore according to manufacturer's protocol (Invitrogen #z25051, z25151, z25251). Binding of representative E11 antibody 5A10 to human FcRH5 transfected EJM (FIG. 3A) and OPM2 (FIG. 3B) multiple myeloma cell lines was found to be similar or better compared previously described non-isoform selective FcRH5 antibodies 10A8 and 7D11 (both bind Ig-like domains 4-5 of FcRH5c) (Elkins et al., 2012; Polson et al., 2006). MOLP-2 cells are one of the very few known multiple myeloma cell lines that express low levels of FcRH5 endogenously. 5A10, 5F1, 3G7 and 6D2 subclone supernatants stained MOLP-2 cells with intensity similar to 7D11 (FIGS. 3C-F).

Figure 4A:
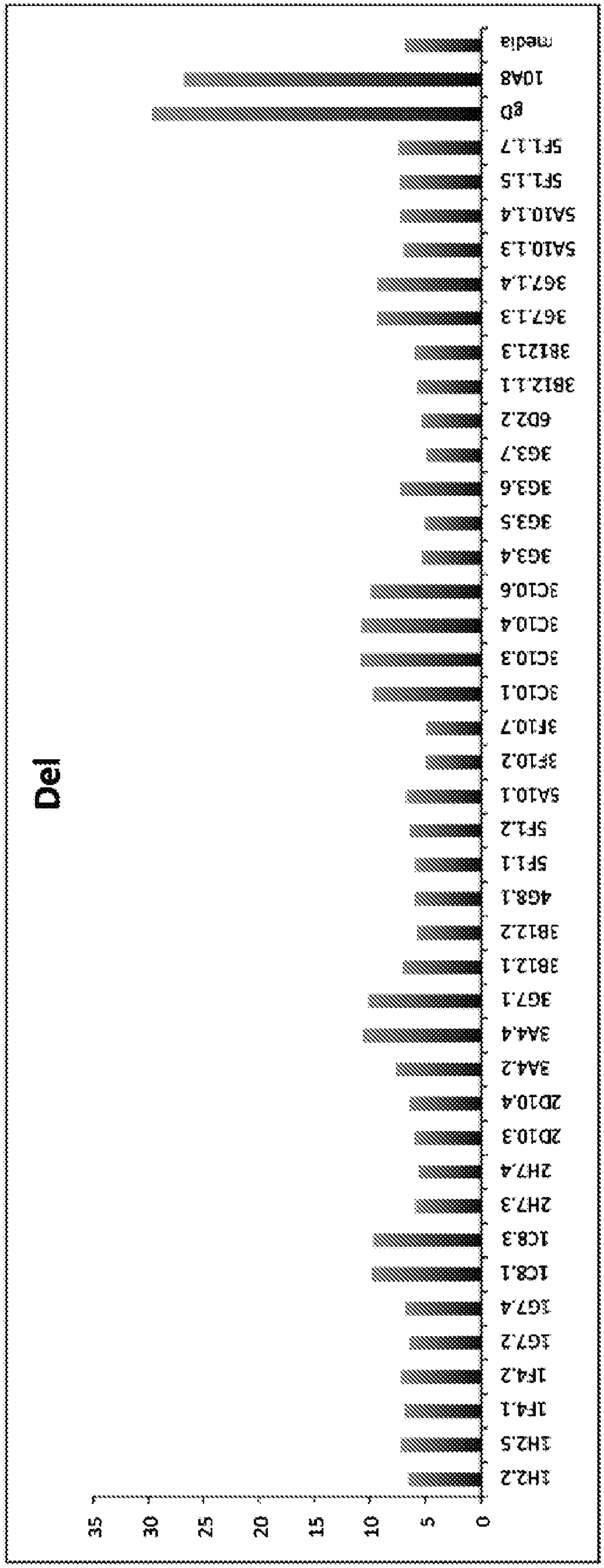
FIG. 4A shows binding of FcRH5 subclone supernatants to 293 cells transfected with mutant FcRH5 with deletion of 4 membrane proximal extracellular domains.
Figure 4B:
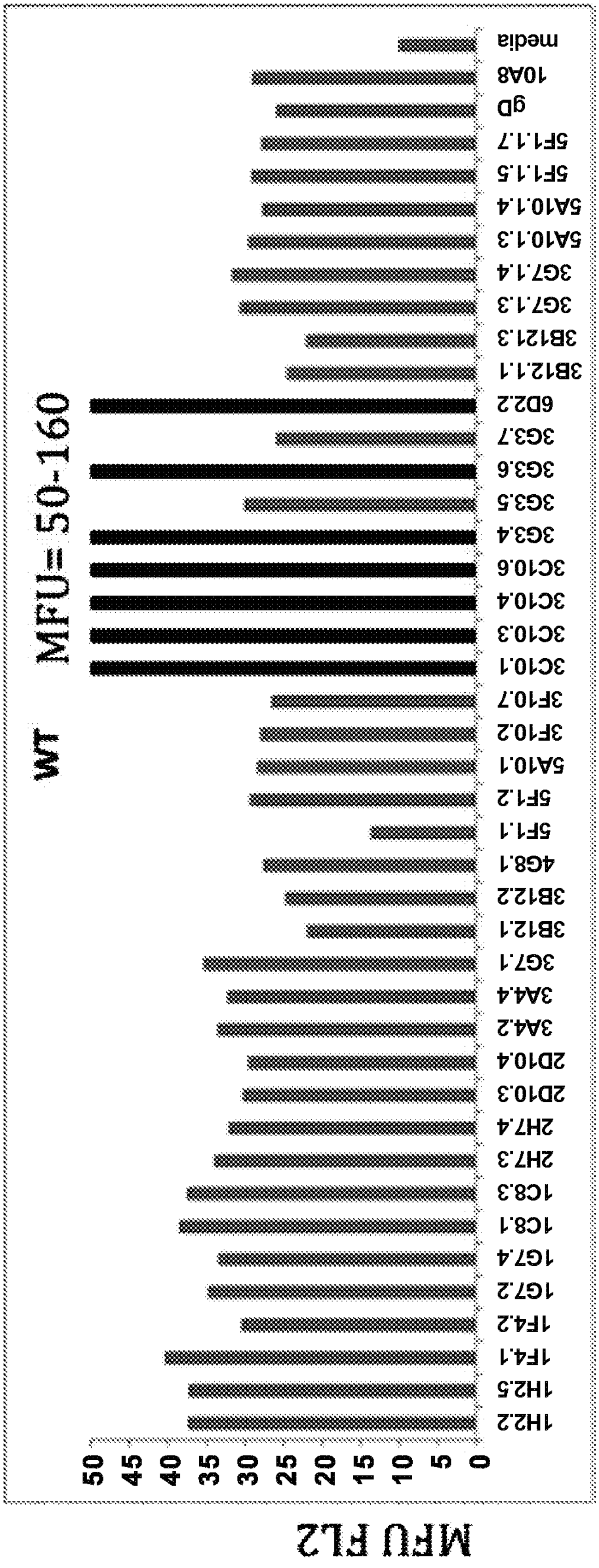
FIG. 4B shows binding of FcRH5 subclone supernatants to 293 cells transfected with WT

Two separate tests were designed to address dependency of binding on the presence of membrane proximal Ig-domain 9 (E11). First a truncated human FcRH5c mutant was generated that lacks Ig-domains 6-9 (amino acids 464-850 of SEQ ID NO:1) including the expected binding site for the antibodies derived from E11 immunization. This construct with N-terminal gD-tag was expressed in 293 cells and subjected to 2.5 ug/ml subclone supernatants followed by PE labeled goat anti-mouse secondary antibody (1:1000 dilution). None of the tested subclones bound to 293 cells that express the truncated human FcRH5c (FIG. 4A). In contrast binding was detected to 293 cells that express wild type human FcRH5c. Binding of gD or non-isoform selective antibody clone (10A8) was not altered by the mutation. This result demonstrates that binding site of the E11 antibodies was included in Ig-domains 6-9.

Figure 5A:
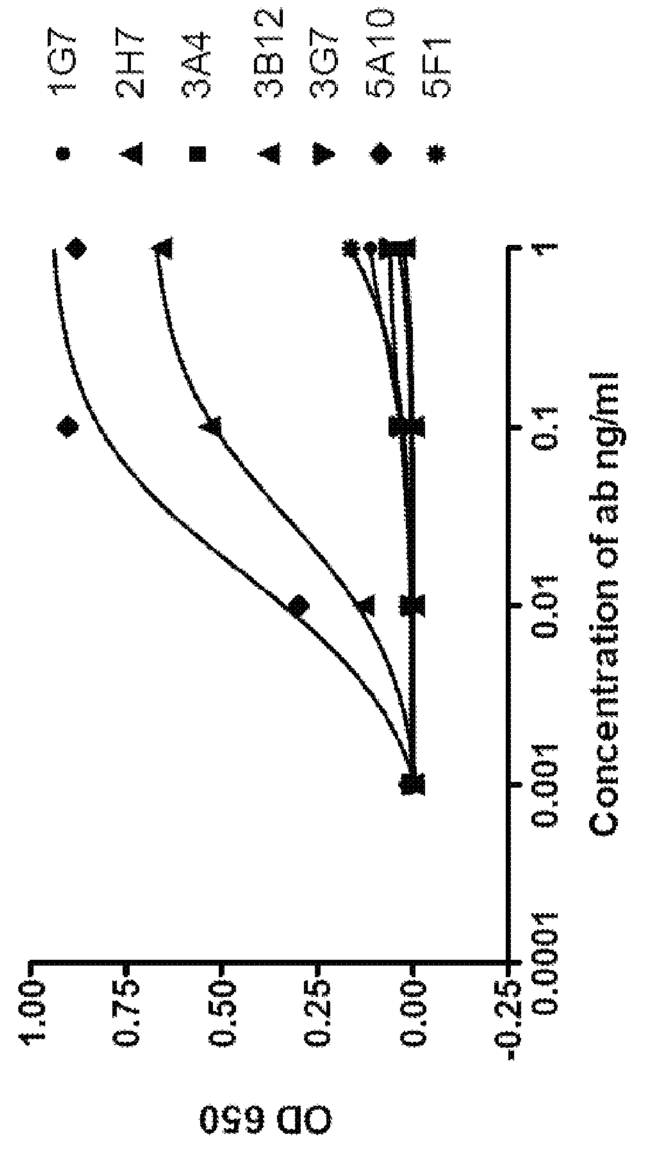
FIG. 5A shows binding of the FcRH5 antibodies to FcRH5a by ELISA.

Isoform selectivity was further demonstrated by testing binding to the soluble FcRH5a isoform. For this, 293 cells were transfected to express the soluble isoform with C-terminal IRS-expression tag. Expression of FcRH5a protein was confirmed with Western blot analysis using anti-HIS antibody. A 65 kD band was detected in conditioned media from FcRH5a but not vector transfected cells (not shown). For the ELISA, plates were coated with anti-HIS capture antibody and incubated 1 hour with 1:10 diluted conditioned media including the HIS-tagged soluble FcRH5a isoform. The E11 monoclonal antibodies were used for detection in 1-0.001 ug/ml concentration, incubated for 1 hour followed by incubation with goat anti-mouse HRP antibody and finally with TMB-substrate. While clones 2H7 and 5A10 demonstrate considerable reactivity to soluble FcRH5a, the other tested monoclonal antibodies do not show any detectable binding (FIG. 5A). This result confirms that the Ig-domain 9 (E11) is required for binding of the antibodies 1G7, 3A4, 3B12, 3G7 and 5F1, and therefore these antibodies are selective for full the length FcRH5 isoform (FcRH5c).

Figure 5B:
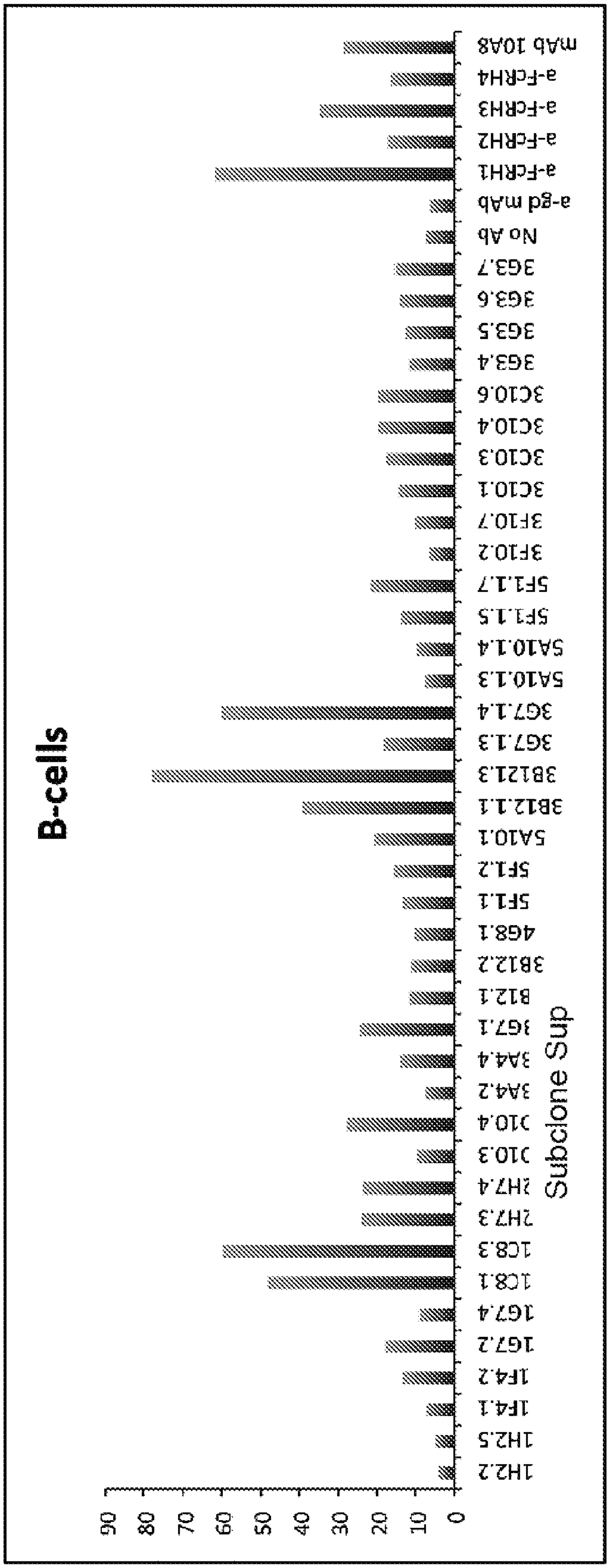
FIG. 5B shows binding of FcRH5 subclone supernatants to human B cells.

FcRH5 is expressed endogenously in B-cells (Hatzivassiliou et al., 2001; Polson et al., 2006). To evaluate binding of subclone supernatants to B-cells, PBMCs were extracted from the blood of healthy donors. 1 million human PBMC were incubated with 4 ug/ml subclone supernatants for 60 min, washed and incubated with 1:100 dilution of goat anti-mouse secondary labeled with APC. Cells were then washed again twice and stained PE-labeled anti-CD19 (BD Biosciences #340364) prior flow cytometry and analysis of binding to CD19+ cells. Most of the supernatants induced a significant shift in the APC signal in CD19+ cells (FIG. 5B) over the controls (no primary antibody, anti-gD) indicative of binding to B cells.

Figure 6A:
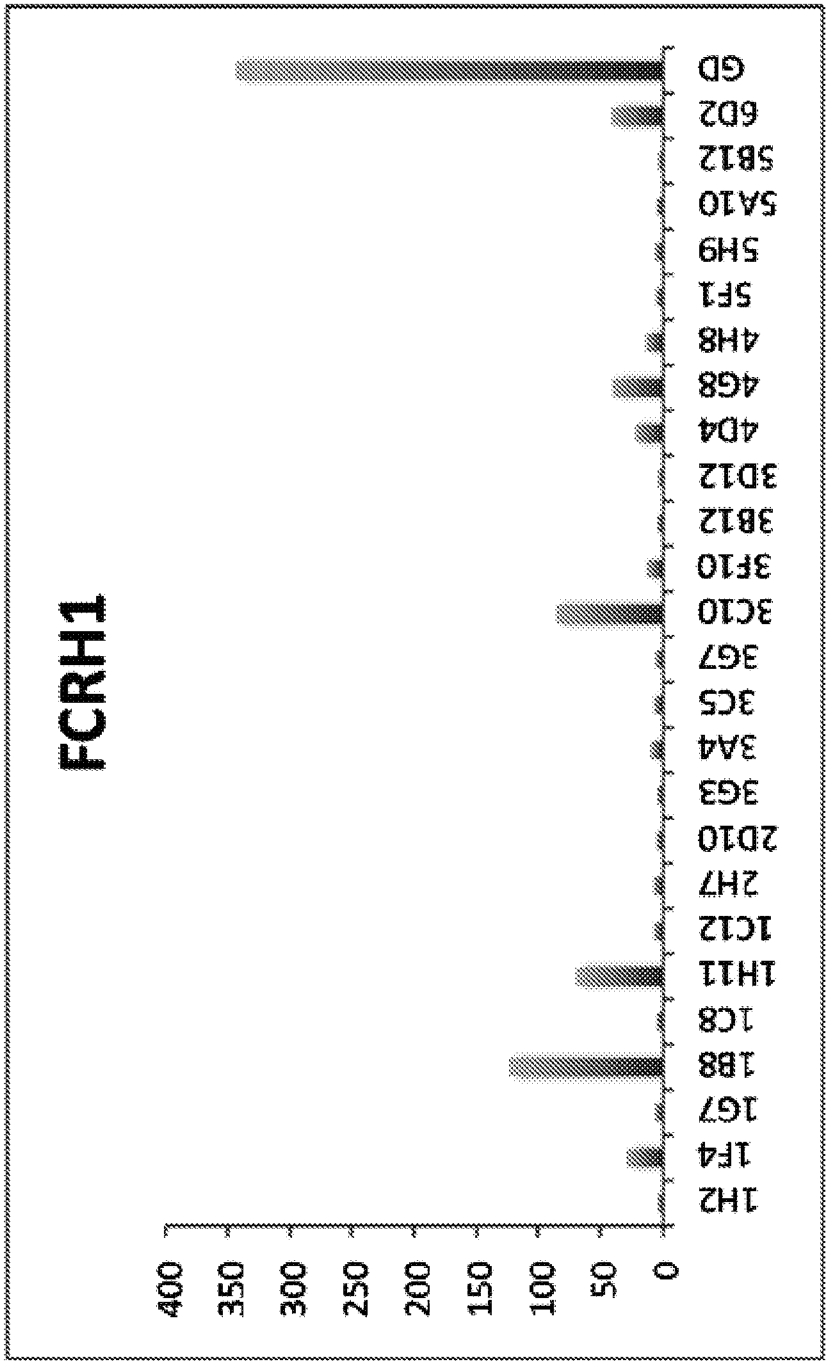
FIG. 6A shows binding of FcRH5 subclone supernatants to SVT2 cells transfected with FcRH1.
Figure 6B:
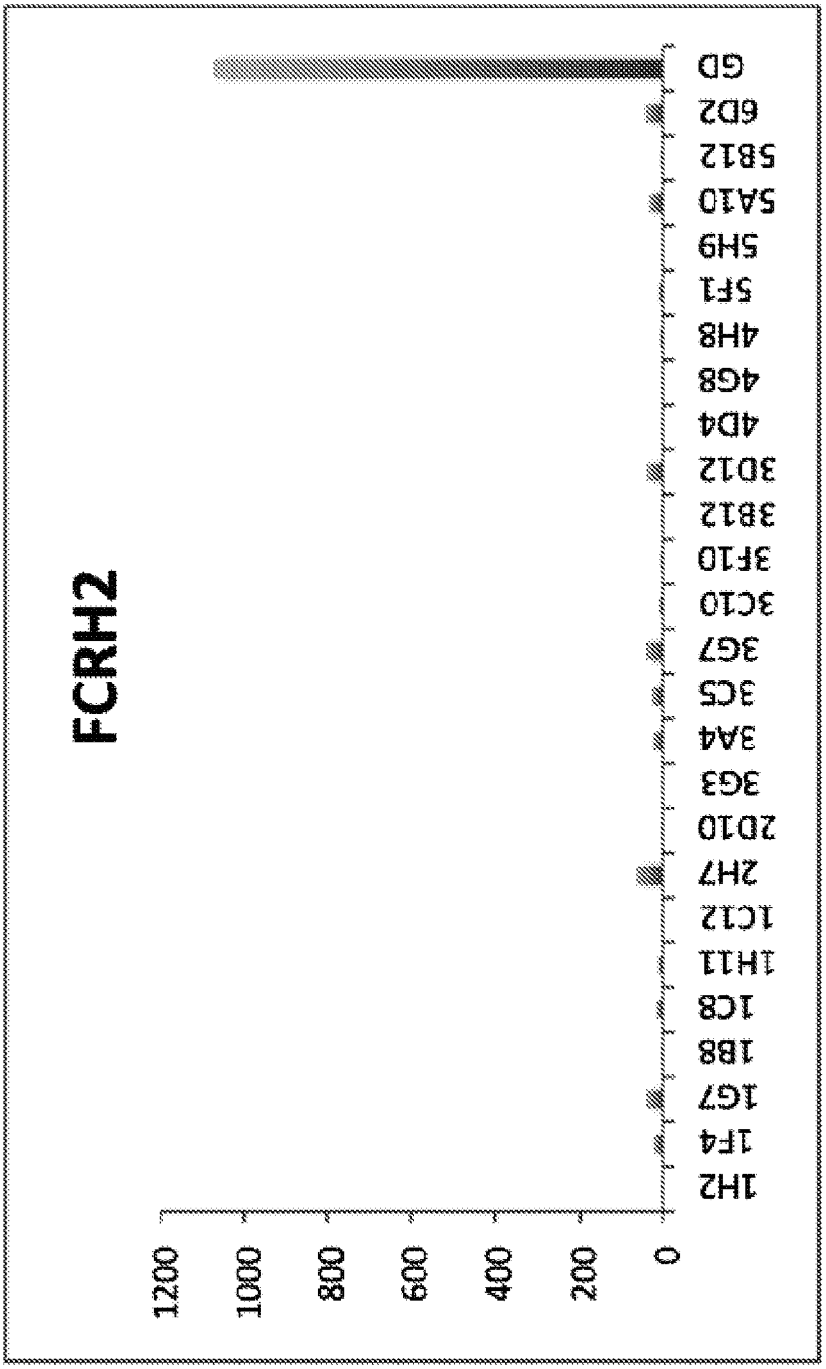
FIG. 6B shows binding of FcRH5 subclone supernatants to SVT2 cells transfected with FcRH2.
Figure 6C:
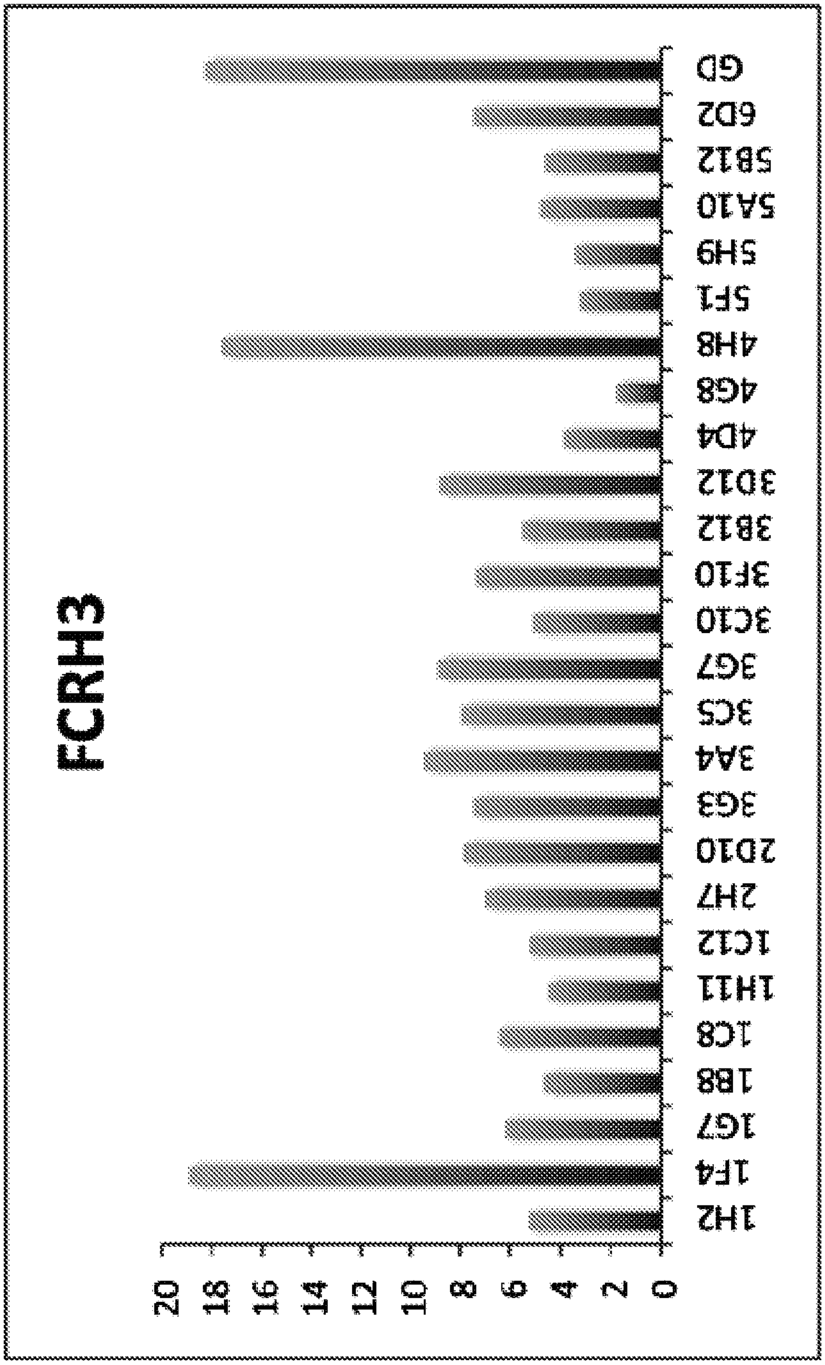
FIG. 6C shows binding of FcRH5 subclone supernatants to SVT2 cells transfected with FcRH3.
Figure 6D:
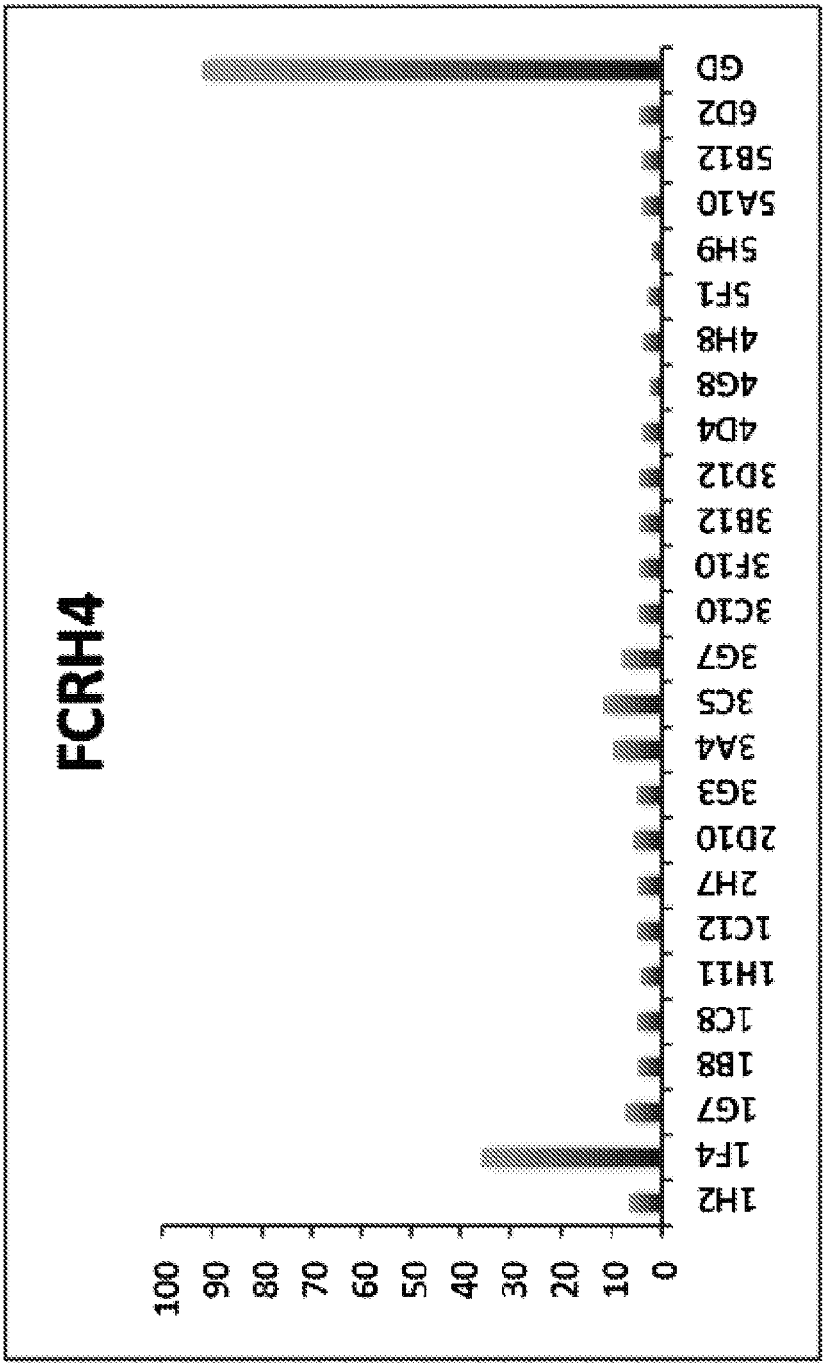
FIG. 6D shows binding of FcRH5 subclone supernatants to SVT2 cells transfected with FcRH4.

Fc receptor homolog (FcRH) family molecules have a high degree of homology to one another (Miller et al., 2002). The homology is especially high between the membrane proximal domains, which the E11 antibodies target (Miller et al., 2002). To investigate the cross reactivity to family members, FcRH1, FcRH2, FcRH3 and FcRH4 (all including an N-terminal gD-expression tag) were expressed in SVT2 cells and cells were stained with subclone supernatants and goat anti-mouse-PE secondary antibody. Expression of the transfected FcRH was confirmed by a signal from anti-gD antibody in all cell lines. None of the supernatants bound significantly to FcRH2 expressing cells as compared to staining with the gD antibody (FIG. 6B). 1B8, 1H11, 3C10, 4G8 and 6D2 demonstrated a low level of binding to FcRH1 (FIG. 6A) and 1F4 bound to FcRH4 (FIG. 6D). Overall, the signals from FcRH3-expressing SVT2 cells were low, including the gD control antibody, indicative of low expression level. Low level of binding to FcRH3-expressing SVT2 cells was detected for 1F4 and 4H8 supernatants (FIG. 6C).

Figure 7:
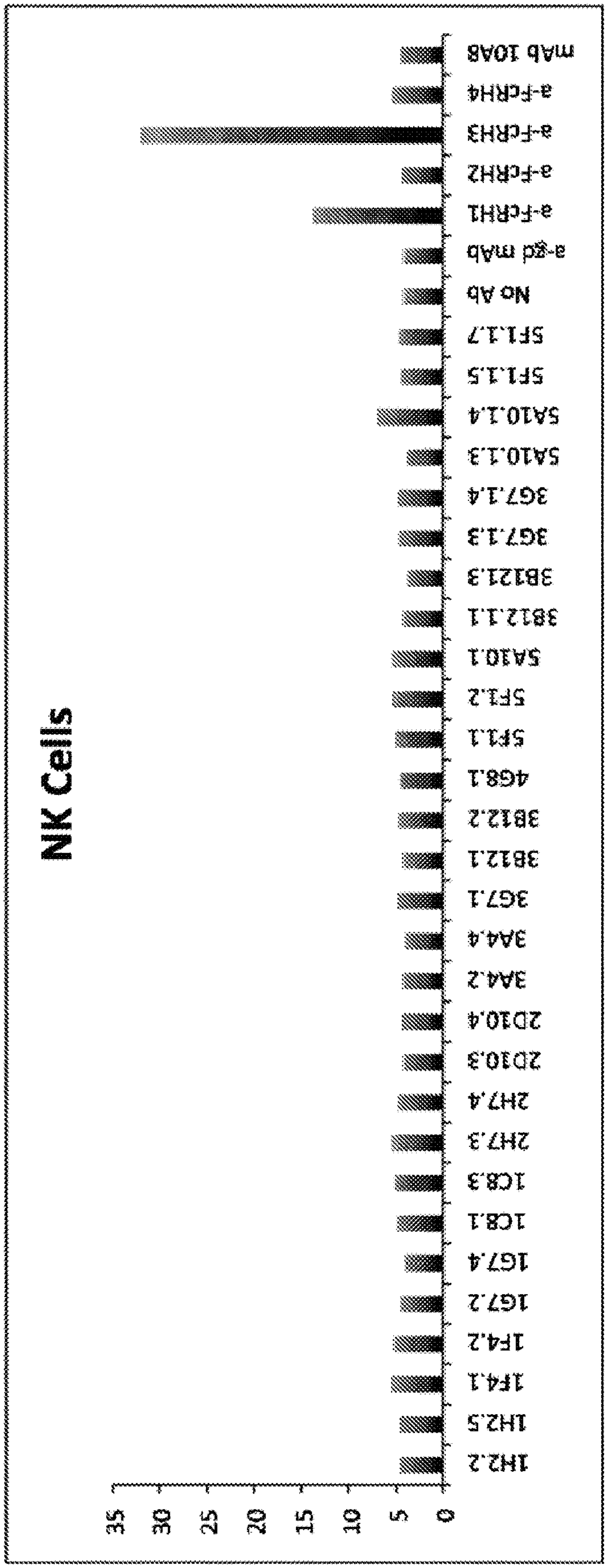
FIG. 7 shows the binding of FcRH5 antibody subclone supernatants to NK cells.

Since the overall signal in the FcRH3-expressing SVT2 cells was low, further testing was done using PBMCs from healthy donors. PBMCs were stained as described above, but instead of CD19, CD56 (BD Biosciences #555516) was used to gate the investigated cell population to NK cells. NK-cells express endogenously FcRH3 (Polson et al., 2006), and as expected, were stained by a previously described monoclonal anti-FcRH3 antibody (Polson et al., 2006). FcRH1 expression was also detected in CD56+ cells, but none of the E11 subclone supernatants significantly stained the NK cells (FIG. 7) demonstrating lack of cross reactivity to endogenously expressed FcRH3.

The cross reactivity of the family members were re-tested using the identical protocol described above in SVT2 cells but using fresh reagents and re-transfecting SVT2 cells with FcRH1, FcRH2, FcRH3, and FcRH4. Re-testing the purified antibodies as described above resulted in significantly different results than the first series of experiments. These updated results are summarized in Table 4. Rather than showing little to no cross-reactivity with other FcRH family members, all but one antibody (1G7) showed significant binding to both FcRH5 and at least one or more other family members. Without being bound by theory, this amount of antibody cross-reactivity is what would be expected, given the sequence similarity of the last Ig-like domain in the various FcRH family members.

CD8+ T cells are among the most potent immune effector cells. The activity of T cells can be recruited to kill tumor cells by using bispecific antibodies (or antibody fragments) that simultaneously bind both T cell and a tumor antigen. The dual binding can lead to a polyclonal activation of T cells and specific killing of tumor antigen expressing cells (Liu et al., 1985; Shalaby et al., 1992). Several tumor targets and several bispecific antibody platforms have demonstrated general flexibility and preclinical feasibility for this approach. Importantly, promising clinical activity has been demonstrated with a CD19 targeting, T cell activating bispecific scFv antibody fragment blinatumomab (MT103; MicroMet). Treatment with doses as low as 60 ug/m$^2$/day results in prolonged responses in clinical trials for treatment of relapsed non-Hodgkin's lymphoma and acute lymphoblastic leukemia (Bargou et al., 2008; Dreier et al., 2002)

The ability of the FcRH5 antibodies to activate T cell and mediate killing in bispecific antibody format was investigated by generating bispecific bisFab molecules. In short, these bispecific molecules are generated by proteolytical cleavage of the antibody, followed by reduction, re-oxidation reactions and conjugation of Fab-fragments using bismaleamide (Scheer et al., 2012b and as described above). Anti-CD3 antibody clone UCHT1 binds to human CD3 that incorporates to T cell receptor. UCHT1.v9 has previously been shown to be efficient T cell binding arm (Junttila et al., 2012 and as described above; Zhu et al., 1995) and therefore was used to the FcRH5 bisFabs. Nine anti-FcRH5 antibody clones (1G7, 2H7, 3G7, 5A10, 5F1, 6D2, 3B12, 3C10, 3F10) from the E11 immunization were chosen for the target arm and conjugated with UCHT1.v9 to result in CD3-FcRH5 bispecific bisFab molecules.

In addition to bisFab molecules, also full length bispecific antibodies (T cell dependent bispecific antibodies; TDBs) were produced using knobs-into-holes technology (Merchant et al., 1998), which relies on a pair of complementary engineered Fc regions that drive heterodimerization of antibody hemimers. As in the case of bisFabs, the UCHT1.v9 (Zhu et al., 1995) was used as the anti-CD3 (hole). For the target arm (knob), antibody clones from the FcRH5 E11-immunization, a non-isoform selective anti-FcRH5 clone (10A8) (Elkins et al., 2012) or anti-HER2 clone 4D5 (trastuzumab) (Carter et al., 1992) were used. Generation and purification of the TDBs has been described in detail (Junttila et al., 2012; Scheer et al., 2012a and as described above).

Figure 8A:
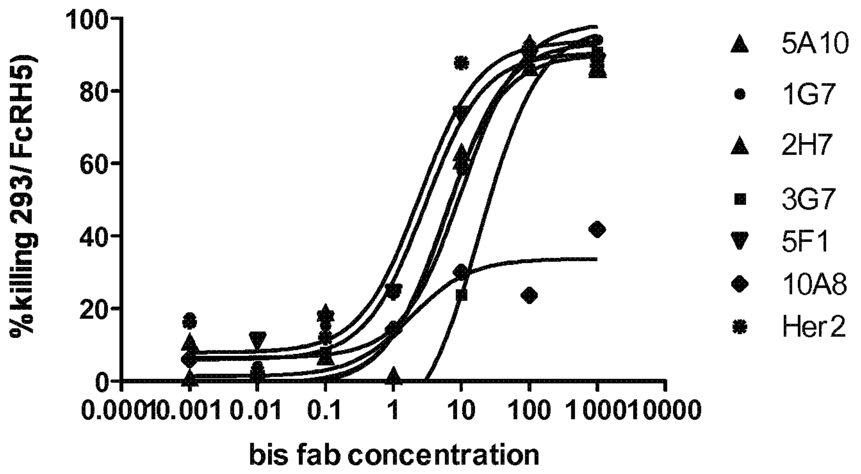
FIG. 8A shows killing activity of FcRH5 bisFabs, FcRH5-TDB (clone 10A8) and HER2-TDB on FcRH5 transfected 293 cells.
Figure 8B:
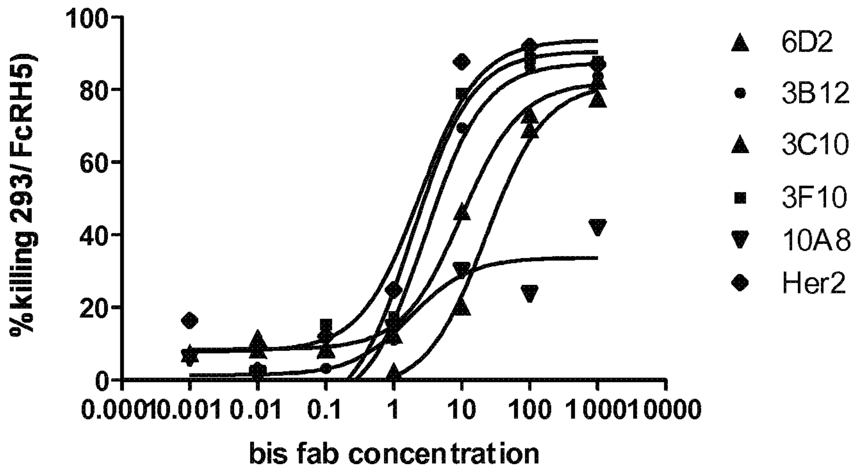
FIG. 8B shows killing activity of additional FcRH5 bisFabs in comparison with FCRH5-TDB and HER2-TDB on FcRH5 transfected 293 cells.
Figure 8C:
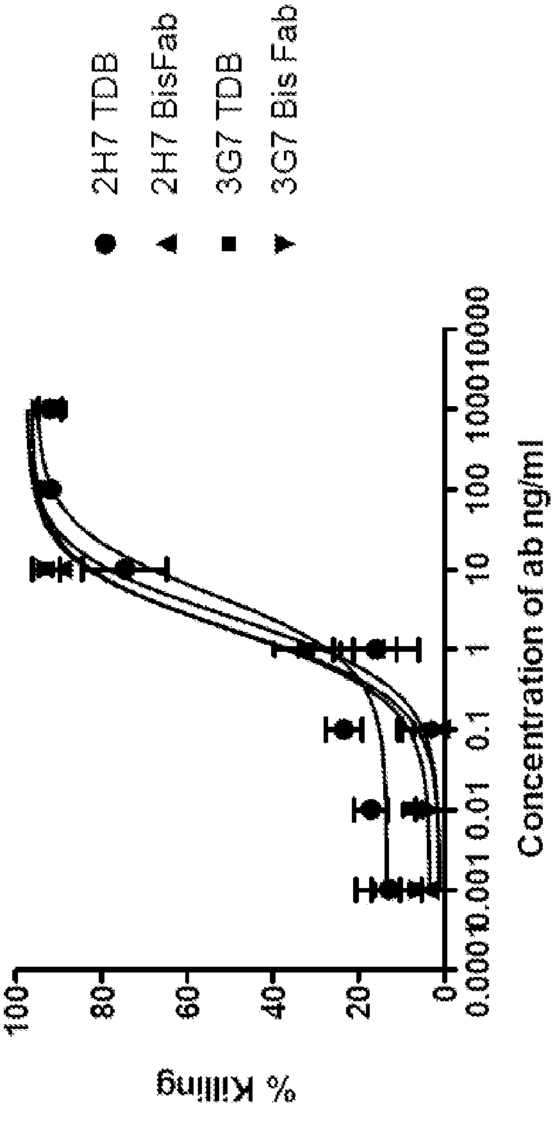
FIG. 8C shows killing activity of FcRH5-bisFabs and FcRH5-TDBs incorporating 2H7 or 3G7 as target arms on FcRH5 transfected 293 cells.
Figure 8D:
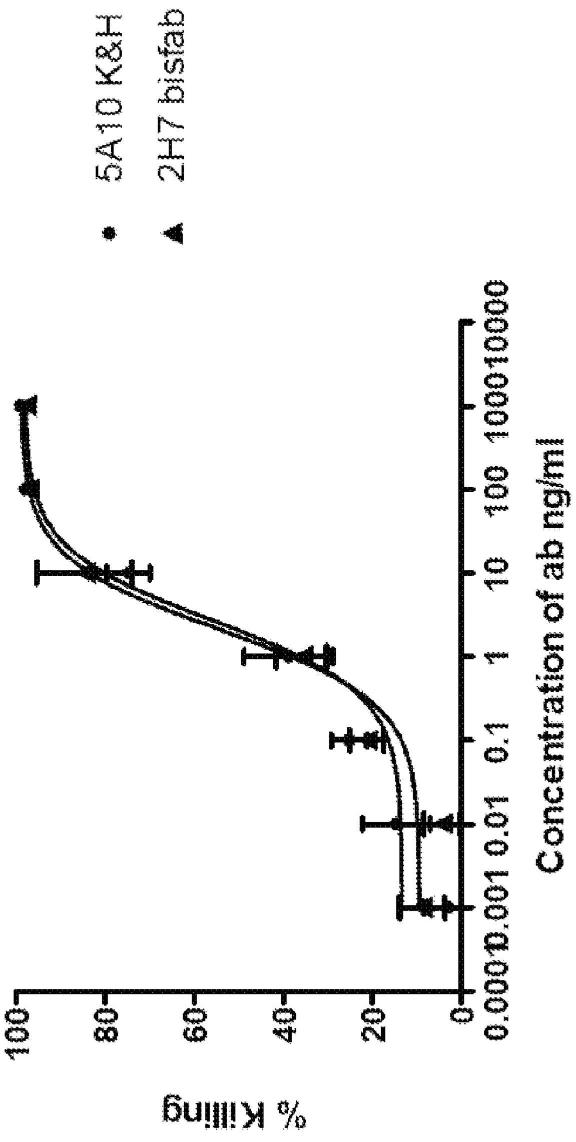
FIG. 8D shows killing activity of FcRH5-bisFabs incorporating 2H7 as target arms and FcRH5-TDBs incorporating 5A10 as target arms on FcRH5 transfected 293 cells.
Figure 9A:
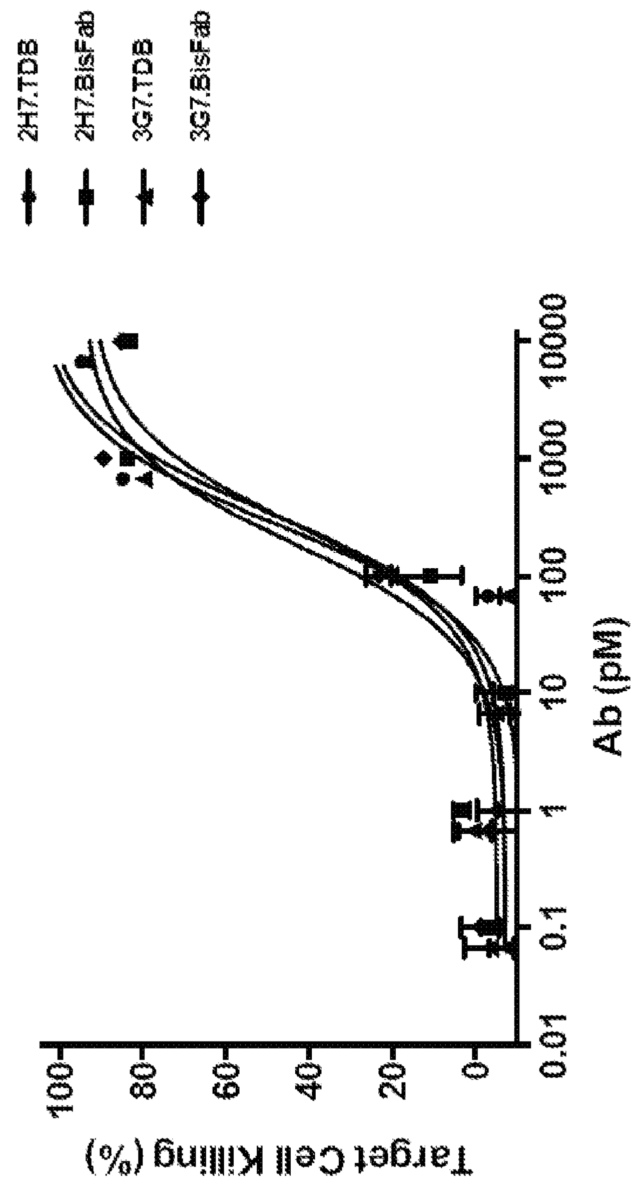
FIG. 9A shows killing activity of FcRH5 bis Fabs and FcRH5-TDBs on MOLP-2 cells.
Figure 9B:
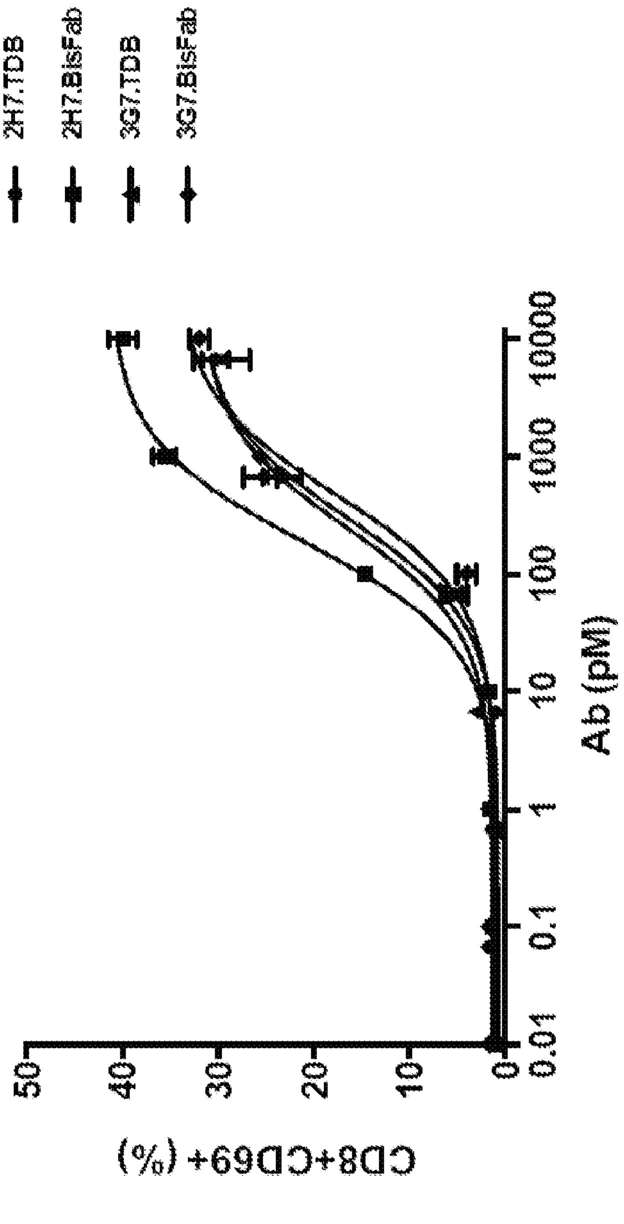
FIG. 9B shows T-cell activation of FcRH5 bisFabs and FcRH5-TDBs on MOLP-2 cells.

The ability of the bispecific molecules to mediate killing of FcRH5 transfected 293 target cells was investigated by incubating the targets with CD8+ T cells (effector cells) for 48 hours and measuring the killing activity using Cell Titer Glo assay or FACS killing assay (assays described above). All nine bisFabs that incorporated an anti-FcRH5 E11 target arm were efficient in mediating target cell killing (FIG. 8A-B). Killing activity was detected as low as 1-10 ng/ml concentrations and saturated at 10-100 ng/ml concentration. Maximal killing activity exceeded 80% for most of the clones. The killing activity was similar compared to the HER2-TDB (FIG. 8A-B). Human HER2 is expressed in the 293 cells on low level (data not shown). In contrast, killing activity far exceeded the non-isoform selective FcRH5-TDB (10A8), which was capable in killing only approximately 20% of the targets (FIG. 8A-B). Similar robust activity was detected using a full length TDB format incorporating 2H7, 3G7 and 5A10 FcRH5-E11 clones as target arms (FIG. 8C-D). No significant difference was detected between TDB and bisFab versions of 2H7 and 3G7 indicating that Fc is neither necessary for the activity nor inhibitory for the killing activity. FcRH5 bisFabs and full length TDBs incorporating 2H7 and 3G7 as target arm were also able to efficiently mediate killing of MOLP2 cells, which express endogenously low levels of FcRH5 (FIG. 9A). T cell activation was followed in the reactions measuring the proportion of CD8+ cells that express CD69 on the cell membrane. T cell activation corresponded the killing activity and was similar for both bisFabs and TDBs (FIG. 9B). A summary of the results are shown in Table 3.

TABLE 3

| Clone | IHC cell pellet | IHC tonils | Molp 2 | SVT2/ human | SVT2/ Cyno | SVT2/ FcRH1 | SVT2/ FcRH2 | SVT2/ FcRH3 | SVT2/ FcRH4 | 293/ huFCRH5 WT | 293/ Mutant | B-cell | Mono-cyte | NK cell | IRTA2a |
|---|---|---|---|---|---|---|---|---|---|---|---|---|---|---|---|
| 1H2.2 | − | − | + | +/− | + | − | − | − | − | + | − | − | − | − | − |
| 1H2.5 | − | − | + | +/− | +/− | − | − | − | − | + | − | − | − | − | − |
| 1F4.1 | − | − | +/− | +/− | +/− | − | − | − | − | + | − | +/− | − | − | − |

TABLE 3-continued

| Clone | IHC cell pellet | IHC tonils | Molp 2 | SVT2/ human | SVT2/ Cyno | SVT2/ FcRH1 | SVT2/ FcRH2 | SVT2/ FcRH3 | SVT2/ FcRH4 | 293/ huFCRH5 WT | 293/ Mutant | B-cell | Mono- cyte | NK cell | IRTA2a |
|---|---|---|---|---|---|---|---|---|---|---|---|---|---|---|---|
| 1F4.2 | − | − | + | +/− | +/− | − | − | − | − | + | − | + | − | − | − |
| 1G7.2 | − | − | ++ | ++ | + | − | − | − | − | + | − | + | − | − | − |
| 1G7.4 | − | − | + | ++ | + | − | − | − | − | + | − | +/− | − | − | − |
| 1C8.1 | + | − | + | ++ | ++ | − | − | − | − | + | − | ++ | − | − | +/− |
| 1C8.3 | + | − | + | ++ | ++ | − | − | − | − | + | − | ++ | − | − | +/− |
| 2H7.3 | + | + | + | +++ | +++ | − | +/− | − | − | + | − | + | − | − | ++ |
| 2H7.4 | + | − | ++ | +++ | +++ | − | +/− | − | − | + | − | + | − | − | ++ |
| 2D10.3 | + | + | + | + | +/− | − | | − | − | + | − | +/− | − | − | + |
| 2D10.4 | + | + | + | + | +/− | − | | − | − | + | − | + | − | − | − |
| 3F10.2 | + | − | + | + | + | − | | − | − | + | − | +/− | − | − | − |
| 3F10.7 | + | − | + | + | + | − | | − | − | + | − | + | − | − | − |
| 3A4.2 | − | − | + | ++ | ++ | − | − | − | − | + | − | + | − | − | ++ |
| 3A4.4 | − | − | ++ | ++ | ++ | − | − | − | − | + | − | + | − | − | ++ |
| 3G7.1 | − | − | ++ | + | ++ | − | − | − | − | + | − | ++ | − | − | + |
| 3B12.1 | + | + | + | ++ | + | − | − | − | − | + | − | ++ | − | − | − |
| 3B12.2 | + | + | + | ++ | + | − | − | − | − | + | − | ++ | − | − | − |
| 4G8.1 | + | − | + | ++ | +/− | − | − | − | − | + | − | + | − | − | − |
| 5F1.1 | − | − | ++ | ++ | ++ | − | − | − | − | +/− | − | + | − | − | − |
| 5F1.2 | − | − | + | ++ | ++ | − | − | − | − | + | − | + | − | − | − |
| 5A10.1 | + | + | ++ | +++ | +++ | − | − | − | − | + | − | + | − | − | +++ |
| 6D2.2 | − | − | ++ | ++ | ++ | − | − | − | − | + | − | + | − | − | + |
| 3G3.5 | + | − | + | + | + | − | − | − | − | + | − | + | − | − | − |
| 3G3.7 | + | − | + | + | + | − | − | − | − | ++ | − | + | − | − | − |
| 3C10.3 | + | + | + | ++ | + | − | − | − | − | ++ | − | + | − | − | + |
| 3C10.4 | + | + | + | ++ | + | − | − | − | − | ++ | − | + | − | − | + |

TABLE 4

| Clone | SVT2/ FcRH1 | SVT2/ FcRH2 | SVT2/ FcRH3 | SVT2/ FcRH4 | SVT2/ FcRH5 |
|---|---|---|---|---|---|
| 1G7.2.mIgG1 | − | − | − | − | +++ |
| 2H7.3.mIgG2b | − | +++ | +++ | − | +++ |
| 3G7.1.mIgG2a | − | ++ | +++ | − | +++ |
| 5F1.1.mIgG2a | +/− | +/− | +++ | − | +++ |
| 5A10.1.mIgG2b | − | +++ | +++ | − | +++ |
| 3B12.1.mIgG2b | − | − | +++ | − | +++ |
| 3A4.2.hIgG1 | − | ++ | +++ | − | +++ |
| 6D2.2.hIgG1 | − | +++ | ++ | − | +++ |
| 1C8.1.hIgG1 | − | ++ | +++ | − | +++ |
| 3C10.3.hIgG1 | +++ | +/− | − | − | +++ |
| 3F10.7.hIgG1 | − | − | ++ | − | ++ |

REFERENCES

Bargou, R. et al. (2008). Science 321, 974-977.

Carter, P. et al. (1992). Proc Natl Acad Sci USA 89, 4285-4289.

Dreier, T. et al. (2002). Int J Cancer 100, 690-697.

Elkins, K. et al. (2012). Mol Cancer Ther 11, 2222-2232.

Hatzivassiliou, G. et al. (2001). Immunity 14, 277-289.

Liu, M. A. et al. (1985). Proc Natl Acad Sci USA 82, 8648-8652.

Merchant, A. M. et al. (1998). Nat Biotechnol 16, 677-681.

Miller, I et al. (2002). Blood 99, 2662-2669.

Polson, A. G. et al. (2006). Expression pattern of the human FcRH/IRTA receptors in normal tissue and in B-chronic lymphocytic leukemia. International immunology 18, 1363-1373.

Shalaby, M. R. et al. (1992). J Exp Med 175, 217-225.

Zhu, Z. et al. (1995). Int J Cancer 62, 319-324.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| Variable Light Chain Domain |
|---|
| 1C8.1 |
| (SEQ ID NO: 110) |
| DIVMTQSQRFMSTSLGDRVSVTCKASQNVITNVAW |
| YQQKPGQSPKALIYSASYRYSGVPDRFTGSGSGTD |
| FTLTISNVQSEDLAEYFCQQYTNYPMWTFGGGTRL |
| EIKRTVA |
| 1G7.2 |
| (SEQ ID NO: 112) |
| DIVMTQSHKIIVISTSVGDRVSITCKASQDVSNIV |
| VWFQQKPGQSPNLLIYSASYRYTGVPDRFTGSGSG |
| TDFTFTISSVQAEDLAVYYCQQHYSSPYTFGGGTK |
| LEIKRTVAA |
| 2H7.3 |
| (SEQ ID NO: 114) |
| EIVLTQSPATLSVTPGDSVSLSCRASQNIRNNLHW |
| YQQKSHESPRLLIKFTSQSISGIPSRFTGSGSGTD |
| FTLSINSVETEDFGMYFCQQSNNWPQYTFGGGTKL |
| EIKRTVAA |
| 3A4.2 |
| (SEQ ID NO: 116) |
| DIQMTQSPATLSVTPGDSVSLSCRASQSISNNLHW |
| YQQKSHESPRLLIKFASQSISGIPSRFSGSGSGTD |
| FTLSINSVETEDFGMYFCQQSNNWPQYTFGGGTKL |
| ELKRTVAA |

| Variable Light Chain Domain |
|---|
| 3B12.1.1 (SEQ ID NO: 118) DIQMTQSPASLSASVGETVTITCRASENIYSNLAW YQLKQGKSPQLLVYGAANLAEGVPSRISGSGSGTQ YSLKINSLQSEDFGTYYCQHFWGIPWTFGGGTKLE IKRTVAA |
| 3C10 (SEQ ID NO: 120) DIQMTQTPLSLPVTLGDQASISCRSSQSLVHRNGN TYLHWYLQKPGQSPKLLIYKVSNRFSGVPDRFSGS GSGTDFTLKISRVEAEDLGVYFCSQSTHVPPTFGG GTKLELKRTVAA |
| 3F10 (SEQ ID NO: 122) DIVMTQSPASLSASVGETVTITCRASENIYSNLAW YQLKQGKSPQLLVYGAANLAEGVPSRISGSGSGTQ YSLKINSLQSEDFGTYYCQHFWGIPWTFGGGTKLE IKRTVAA |
| 3G3 (SEQ ID NO: 124) DIVMTQSPASLSASVGETVTITCRASENIYSNLAW YQLKQGKSPQLLVYGAANLAEGVPSRISGSGSGTQ YSLKINSLQSEDFGTYYCQHFWGIPWTFGGGTKLE IKRTVAA |
| 3G7.1.5 (SEQ ID NO: 126) DIVLIQSPATLSVTLGGSVSLSCRASQSISNNLHW YQQKSHESPRLLIKFASQSISGIPSRFRGSGSGTD FTLTINSVETEDFGIYFCQQSNNWPQYTFGGGTKL ELKRTVAA |
| 5A10.1.3 (SEQ ID NO: 128) DIVLTQSPANLSVIPGDSVSLSCRASQNIRNNLHW YQQKSQESPRLLIKFASQSMSGTPSRFTGSGSGTD FTLTINTVETEDFGMYFCQQSNNWPQYTFGGGTKL EIKRTVAA |
| 5F1.1.5 (SEQ ID NO: 130) QAVVTQESALTTSPGETVTLTCRSSTGTVTTSNFA NWVQEKPDHLFTGLIGGTSNRAPGVPARFSGSLIG DKAALTITGAQTEDEAIYFCVLWCSNLWVFGGGTK LTVLGQPKAA |
| 6D2 (SEQ ID NO: 132) DIVMTQSHKFMSTSVGDRVSITCKASQDVGTAVAW YQQKPGQSPKLLIFWPSTRHTGVPDRFTGSGSGTD |

| Variable Light Chain Domain |
|---|
| FTLTIGNVQSEDLADYFCQQFSSLPHTFGGGTKLE IKRTVAA |
| 1G7' (SEQ ID NO: 134) DIVMTQSHKIMSTSVGDRVSITCKASQDVSNIVVW FQQKPGQSPNLLIYSASYRYTGVPDRFTGSGSGTD FTFTISSVQAEDLAVYYCQQHYSSPYTFGGGTKLE IK |
| Variable Heavy Chain Domain |
| 1C8.1 (SEQ ID NO: 111) EVQLQQSGPELVKPGASMKISCEASGYSFTAYIMN WVKQSRGKNLEWIGLINPYNGETTYNQKFKGKATL TVDQSSSTAYMELLSLTSEDSAVYFCARGLYWFPY WGQGTLVTVSAASTKGPSVFPLAP |
| 1G7.2 (SEQ ID NO: 113) EVQLQESGPGLVQPSQSLSITCTVSGFSLTRFGVH WVRQSPGKGLEWLGVIWRGGSTDYNAAFMSRLTIT KDNSKSQVFFKLNSLKVDDTAIYYCSNHYYGSSDY ALDNWGQGTSVTVSSASTKGPSVFPLAP |
| 2H7.3 (SEQ ID NO: 115) EVQLQQSGPELWKPGASVKMSCKASGYTFTDYYMK WVKQTHGKSLEWIGDINPNNGETFYSQKFKGKATL TVDKSSTTAYMQLNSLTSEDSAVYYCARGLYRFDY WGQGTTLTVSSASTKGPSVFPLAP |
| 3A4.2 (SEQ ID NO: 117) EVQLQQSGPELVKSGASVKMSCKASGYTFTDYYMK WVKQSHGKSLEWIGDINPYNGETFYNQKLKGKATL TVDKSSNTVFMQLNSLTSEDSAVYYCARGLYFFAY WGQGTTLTVSSASTKGPSVFPLAP |
| 3B12.1.1 (SEQ ID NO: 119) EVQLQQSGPELVKPGASVKISCKTSGYTFTEYTIH WVKQSHGKSLERIGGINPNNDAVSYNQRFRGKATL TVDKSSSTAYMELRSLTSEDSAVYYCAKLGRGYYF DYWGQGTTLTVSSASTKGPSVFPLAP |
| 3C10 (SEQ ID NO: 121) QVQLQQPGAELVRPGASVKLSCKTSGYTFISYWIN WVKQRPGQGLEWIGNIYPSDSYTNYNQKFKDKATL TVDTSSSTAYMQLTSPTSEDSAVYYCTRSLYGYDA SYFDYWGQGTTLTVSSASTKGPSVFPLAP |

| Variable Light Chain Domain |
| --- |
| 3F10 (SEQ ID NO: 123) QVQLQQSGPELVKPGASVKISCKTSGYTFTEYTIH WVKQSHGKSLERIGGINPNNDAISYNQKFRGKATL TVDKSSSTAYMELRSLTSEDSAVYYCAKLGRGYYF DYWGRGTTLTVSSASTKGPSVFPLAP |
| 3G3 (SEQ ID NO: 125) EVQLQQSGPELVKPGASVKISCKTSGYTFTEYTIH WVKQSHGKSLERIGGINPNNDAISYNQKFRGKATL TVDKSSSTAYMELRSLTSEDSAVYYCAKLGRGYYF DYWGRGTTLTVSSASTKGPSVFPLAP |
| 3G7.1.5 (SEQ ID NO: 127) EVQLQQSGPELVKPGASVKMSCKASGYTFTDYYMK WVRQNHGKRLEWIGDINPYNGDTFYNQKFKDKATL TVDKSSSTAYMQFNSLTSEDSAVYYCARGLYFFHY WGQGTTLTVSSASTKGPSVFPLAP |
| 5A10.1.3 (SEQ ID NO: 129) EVQLQQSGPELWKPGASVKMSCKASGYTFTDYYMK WVKQSHGKSLEWIGDINPNNGETFYNQKFKGKATL TVDKSTSTAYMELNSLTTEDSAVYYCARGLYRFDY WGQGTTLTVSSAASTKGPSVFPLAP |
| 5F1.1.5 (SEQ ID NO: 131) QVQLQQSGADLVRPGTSVKVSCKASGYAFTNYLIE WVKQRPGQGLEWIGVINPGSGGTNYNEKFKGKATL TADKSSSTAYMQLSSLTSDDSAVYFCARTRNYGYV IDYWGQGTTLTVSSASTKGPSVFPLAP |
| 6D2 (SEQ ID NO: 133) QVQLQQSGPELVKPGASVKISCKASGFSFTAYFMN WVKQSHGKSPEWIGRINPYNGETFFNQNFKDKATL TVDKSSNTAHMELLSLTSDDSAVYYCGRGLYYLNY WGQGTTLTVSSASTKGPSVFPLAP |
| 1G7' (SEQ ID NO: 135) QVQLKQSGPGLVQPSQSLSITCTVSGFSLTRFGVH WVRQSPGKGLEWLGVIWRGGSTDYNAAFMSRLTIT |

| Variable Light Chain Domain |
| --- |
| KDNSKSQVFFKLNSLKVDDTAIYYCSNHYYGSSDY ALDNWGQGISVTVSS |
| FcRH5c (SEQ ID NO: 1) MLLWVILLVLAPVSGQFARTPRPIIFLQPPWTTVF QGERVTLTCKGFRFYSPQKTKWYHRYLGKEILRET PDNILEVQESGEYRCQAQGSPLSSPVHLDFSSASL ILQAPLSVFEGDSVVLRCRAKAEVTLNNTIYKNDN VLAFLNKRTDFHIPHACLKDNGAYRCTGYKESCCP VSSNTVKIQVQEPFTRPVLRASSFQPISGNPVTLT CETQLSLERSDVPLRFRFFRDDQTLGLGWSLSPNF QITAMWSKDSGFYWCKAATMPYSVISDSPRSWIQV QIPASHPVLTLSPEKALNFEGTKVTLHCETQEDSL RTLYRFYHEGVPLRHKSVRCERGASISFSLTTENS GNYYCTADNGLGAKPSKAVSLSVTVPVSHPVLNLS SPEDLIFEGAKVTLHCEAQRGSLPILYQFHHEGAA LERRSANSAGGVAISFSLTAEHSGNYYCTADNGFG PQRSKAVSLSVTVPVSHPVLTLSSAEALTFEGATV TLHCEVQRGSPQILYQFYHEDMPLWSSSTPSVGRV SFSFSLTEGHSGNYYCTADNGFGPQRSEVVSLFVT VPVSRPILTLRVPRAQAVVGDLLELHCEAPRGSPP ILYWFYHEDVTLGSSSAPSGGEASFNLSLTAEHSG NYSCEANNGLVAQHSDTISLSVIVPVSRPILTFRA PRAQAVVGDLLELHCEALRGSSPILYWFYHEDVTL GKISAPSGGGASFNLSLTTEHSGIYSCEADNGLEA QRSEMVTLKVAVPVSRPVLTLRAPGTHAAVGDLLE LHCEALRGSPLILYRFFHEDVTLGNRSSPSGGASL NLSLTAEHSGNYSCEADNGLGAQRSETVTLYITGL TANRSGPFATGVAGGLLSIAGLAAGALLLYCWLSR KAGRKPASDPARSPSDSDSQEPTYHNVPAWEELQP VYTNANPRGENVVYSEVRIIQEKKKHAVASDPRHL RNKGSPIIYSEVKVASTPVSGSLFLASSAPHR |

What is claimed is:

1. A method of treating an individual having an FcRH5-positive cancer, the method comprising administering to the individual an effective amount of an isolated anti-FcRH5 antibody that binds an isoform c-specific region of the extracellular domain of FcRH5c, wherein the isoform c-specific region comprises amino acids 745-850 of SEQ ID NO:1, and wherein the antibody comprises:

(a) a heavy chain comprising an HVR-H1 comprising the amino acid sequence of SEQ ID NO:39, an HVR-H2 comprising the amino acid sequence of SEQ ID NO:63, and an HVR-H3 comprising the amino acid sequence of SEQ ID NO:87, and a light chain comprising an HVR-L1 comprising the amino acid sequence of SEQ ID NO:3, an HVR-L2 comprising the amino acid sequence of SEQ ID NO:15, and an HVR-L3 comprising the amino acid sequence of SEQ ID NO:27;

(b) a heavy chain comprising an HVR-H1 comprising the amino acid sequence of SEQ ID NO:38, an HVR-H2 comprising the amino acid sequence of SEQ ID NO:62, and an HVR-H3 comprising the amino acid sequence of SEQ ID NO:86, and a light chain comprising an HVR-L1 comprising the amino acid sequence of SEQ ID NO:2, an HVR-L2 comprising the amino acid sequence of SEQ ID NO:14, and an HVR-L3 comprising the amino acid sequence of SEQ ID NO:26;

(c) a heavy chain comprising an HVR-H1 comprising the amino acid sequence of SEQ ID NO:41, an HVR-H2 comprising the amino acid sequence of SEQ ID NO:65, and an HVR-H3 comprising the amino acid sequence of SEQ ID NO:89, and a light chain comprising an HVR-L1 comprising the amino acid sequence of SEQ ID NO:5, an HVR-L2 comprising the amino acid sequence of SEQ ID NO:17, and an HVR-L3 comprising the amino acid sequence of SEQ ID NO:29;

(d) a heavy chain comprising an HVR-H1 comprising the amino acid sequence of SEQ ID NO:42, an HVR-H2 comprising the amino acid sequence of SEQ ID NO:66, and an HVR-H3 comprising the amino acid sequence of SEQ ID NO:90, and a light chain comprising an HVR-L1 comprising the amino acid sequence of SEQ ID NO:6, an HVR-L2 comprising the amino acid sequence of SEQ ID NO:18, and an HVR-L3 comprising the amino acid sequence of SEQ ID NO:30;

(e) a heavy chain comprising an HVR-H1 comprising the amino acid sequence of SEQ ID NO:43, an HVR-H2 comprising the amino acid sequence of SEQ ID NO:67, and an HVR-H3 comprising the amino acid sequence of SEQ ID NO:91, and a light chain comprising an HVR-L1 comprising the amino acid sequence of SEQ ID NO:7, an HVR-L2 comprising the amino acid sequence of SEQ ID NO:19, and an HVR-L3 comprising the amino acid sequence of SEQ ID NO:31;

(f) a heavy chain comprising an HVR-H1 comprising the amino acid sequence of SEQ ID NO:44, an HVR-H2 comprising the amino acid sequence of SEQ ID NO:68, and an HVR-H3 comprising the amino acid sequence of SEQ ID NO:92, and a light chain comprising an HVR-L1 comprising the amino acid sequence of SEQ ID NO:8, an HVR-L2 comprising the amino acid sequence of SEQ ID NO:20, and an HVR-L3 comprising the amino acid sequence of SEQ ID NO:32;

(g) a heavy chain comprising an HVR-H1 comprising the amino acid sequence of SEQ ID NO:45, an HVR-H2 comprising the amino acid sequence of SEQ ID NO:69, and an HVR-H3 comprising the amino acid sequence of SEQ ID NO:93, and a light chain comprising an HVR-L1 comprising the amino acid sequence of SEQ ID NO:9, an HVR-L2 comprising the amino acid sequence of SEQ ID NO:21, and an HVR-L3 comprising the amino acid sequence of SEQ ID NO:33;

(h) a heavy chain comprising an HVR-H1 comprising the amino acid sequence of SEQ ID NO:46, an HVR-H2 comprising the amino acid sequence of SEQ ID NO:70, and an HVR-H3 comprising the amino acid sequence of SEQ ID NO:94, and a light chain comprising an HVR-L1 comprising the amino acid sequence of SEQ ID NO:10, an HVR-L2 comprising the amino acid sequence of SEQ ID NO:22, and an HVR-L3 comprising the amino acid sequence of SEQ ID NO:34;

(i) a heavy chain comprising an HVR-H1 comprising the amino acid sequence of SEQ ID NO:48, an HVR-H2 comprising the amino acid sequence of SEQ ID NO:72, and an HVR-H3 comprising the amino acid sequence of SEQ ID NO:96, and a light chain comprising an HVR-L1 comprising the amino acid sequence of SEQ ID NO:12, an HVR-L2 comprising the amino acid sequence of SEQ ID NO:24, and an HVR-L3 comprising the amino acid sequence of SEQ ID NO:36; or (j) a heavy chain comprising an HVR-H1 comprising the amino acid sequence of SEQ ID NO:49, an HVR-H2 comprising the amino acid sequence of SEQ ID NO:73, and an HVR-H3 comprising the amino acid sequence of SEQ ID NO:97, and a light chain comprising an HVR-L1 comprising the amino acid sequence of SEQ ID NO:13, an HVR-L2 comprising the amino acid sequence of SEQ ID NO:25, and an HVR-L3 comprising the amino acid sequence of SEQ ID NO:37.

2. The method of claim 1, wherein the FcRH5-positive cancer is a B-cell proliferative disorder.

3. The method of claim 1, further comprising administering an additional therapeutic agent to the individual.

4. A method of inhibiting proliferation of an FcRH5-positive cell, the method comprising exposing the cell to an isolated anti-FcRH5 antibody that binds an isoform c-specific region of the extracellular domain of FcRH5c under conditions permissive for binding of the antibody to FcRH5 on the surface of the cell, thereby inhibiting proliferation of the cell, wherein the isoform c-specific region comprises amino acids 745-850 of SEQ ID NO:1, and wherein the antibody comprises:

(a) a heavy chain comprising an HVR-H1 comprising the amino acid sequence of SEQ ID NO:39, an HVR-H2 comprising the amino acid sequence of SEQ ID NO:63, and an HVR-H3 comprising the amino acid sequence of SEQ ID NO:87, and a light chain comprising an HVR-L1 comprising the amino acid sequence of SEQ ID NO:3, an HVR-L2 comprising the amino acid sequence of SEQ ID NO:15, and an HVR-L3 comprising the amino acid sequence of SEQ ID NO:27;

(b) a heavy chain comprising an HVR-H1 comprising the amino acid sequence of SEQ ID NO:38, an HVR-H2 comprising the amino acid sequence of SEQ ID NO:62, and an HVR-H3 comprising the amino acid sequence of SEQ ID NO:86, and a light chain comprising an HVR-L1 comprising the amino acid sequence of SEQ ID NO:2, an HVR-L2 comprising the amino acid sequence of SEQ ID NO:14, and an HVR-L3 comprising the amino acid sequence of SEQ ID NO:26;

(c) a heavy chain comprising an HVR-H1 comprising the amino acid sequence of SEQ ID NO:41, an HVR-H2 comprising the amino acid sequence of SEQ ID NO:65, and an HVR-H3 comprising the amino acid sequence of SEQ ID NO:89, and a light chain comprising an HVR-L1 comprising the amino acid sequence of SEQ ID NO:5, an HVR-L2 comprising the amino acid sequence of SEQ ID NO:17, and an HVR-L3 comprising the amino acid sequence of SEQ ID NO:29;

(d) a heavy chain comprising an HVR-H1 comprising the amino acid sequence of SEQ ID NO:42, an HVR-H2 comprising the amino acid sequence of SEQ ID NO:66, and an HVR-H3 comprising the amino acid sequence of SEQ ID NO:90, and a light chain comprising an HVR-L1 comprising the amino acid sequence of SEQ ID NO:6, an HVR-L2 comprising the amino acid sequence of SEQ ID NO:18, and an HVR-L3 comprising the amino acid sequence of SEQ ID NO:30;

(e) a heavy chain comprising an HVR-H1 comprising the amino acid sequence of SEQ ID NO:43, an HVR-H2 comprising the amino acid sequence of SEQ ID NO:67, and an HVR-H3 comprising the amino acid sequence of SEQ ID NO:91, and a light chain comprising an HVR-L1 comprising the amino acid sequence of SEQ ID NO:7, an HVR-L2 comprising the amino acid sequence of SEQ ID NO:19, and an HVR-L3 comprising the amino acid sequence of SEQ ID NO:31;

(f) a heavy chain comprising an HVR-H1 comprising the amino acid sequence of SEQ ID NO:44, an HVR-H2 comprising the amino acid sequence of SEQ ID NO:68, and an HVR-H3 comprising the amino acid sequence of SEQ ID NO:92, and a light chain comprising an HVR-L1 comprising the amino acid sequence of SEQ ID NO:8, an HVR-L2 comprising the amino acid sequence of SEQ ID NO:20, and an HVR-L3 comprising the amino acid sequence of SEQ ID NO:32;

(g) a heavy chain comprising an HVR-H1 comprising the amino acid sequence of SEQ ID NO:45, an HVR-H2 comprising the amino acid sequence of SEQ ID NO:69, and an HVR-H3 comprising the amino acid sequence of SEQ ID NO:93, and a light chain comprising an HVR-L1 comprising the amino acid sequence of SEQ ID NO:9, an HVR-L2 comprising the amino acid sequence of SEQ ID NO:21, and an HVR-L3 comprising the amino acid sequence of SEQ ID NO:33;

(h) a heavy chain comprising an HVR-H1 comprising the amino acid sequence of SEQ ID NO:46, an HVR-H2 comprising the amino acid sequence of SEQ ID NO:70, and an HVR-H3 comprising the amino acid sequence of SEQ ID NO:94, and a light chain comprising an HVR-L1 comprising the amino acid sequence of SEQ ID NO:10, an HVR-L2 comprising the amino acid sequence of SEQ ID NO:22, and an HVR-L3 comprising the amino acid sequence of SEQ ID NO:34;

(i) a heavy chain comprising an HVR-H1 comprising the amino acid sequence of SEQ ID NO:48, an HVR-H2 comprising the amino acid sequence of SEQ ID NO:72, and an HVR-H3 comprising the amino acid sequence of SEQ ID NO:96, and a light chain comprising an HVR-L1 comprising the amino acid sequence of SEQ ID NO:12, an HVR-L2 comprising the amino acid sequence of SEQ ID NO:24, and an HVR-L3 comprising the amino acid sequence of SEQ ID NO:36; or (j) a heavy chain comprising an HVR-H1 comprising the amino acid sequence of SEQ ID NO:49, an HVR-H2 comprising the amino acid sequence of SEQ ID NO:73, and an HVR-H3 comprising the amino acid sequence of SEQ ID NO:97, and a light chain comprising an HVR-L1 comprising the amino acid sequence of SEQ ID NO:13, an HVR-L2 comprising the amino acid sequence of SEQ ID NO:25, and an HVR-L3 comprising the amino acid sequence of SEQ ID NO:37.

5. The method of claim 4, wherein the cell is a B-cell.

6. The method of claim 1, wherein:

(a) in part (a), the heavy chain comprises a VH sequence having at least 95% sequence identity to the amino acid sequence of SEQ ID NO:113 and/or the light chain comprises a VL sequence having at least 95% sequence identity to the amino acid sequence of SEQ ID NO:112;

(b) in part (b), the heavy chain comprises a VH sequence having at least 95% sequence identity to the amino acid sequence of SEQ ID NO:111 and/or the light chain comprises a VL sequence having at least 95% sequence identity to the amino acid sequence of SEQ ID NO: 110;

(c) in part (c), the heavy chain comprises a VH sequence having at least 95% sequence identity to the amino acid sequence of SEQ ID NO:117 and/or the light chain comprises a VL sequence having at least 95% sequence identity to the amino acid sequence of SEQ ID NO:116;

(d) in part (d), the heavy chain comprises a VH sequence having at least 95% sequence identity to the amino acid sequence of SEQ ID NO:119 and/or the light chain comprises a VL sequence having at least 95% sequence identity to the amino acid sequence of SEQ ID NO:118;

(e) in part (e), the heavy chain comprises a VH sequence having at least 95% sequence identity to the amino acid sequence of SEQ ID NO:121 and/or the light chain comprises a VL sequence having at least 95% sequence identity to the amino acid sequence of SEQ ID NO:120;

(f) in part (f), the heavy chain comprises a VH sequence having at least 95% sequence identity to the amino acid sequence of SEQ ID NO:123 and/or the light chain comprises a VL sequence having at least 95% sequence identity to the amino acid sequence of SEQ ID NO:122;

(g) in part (g), the heavy chain comprises a VH sequence having at least 95% sequence identity to the amino acid sequence of SEQ ID NO:125 and/or the light chain comprises a VL sequence having at least 95% sequence identity to the amino acid sequence of SEQ ID NO:124;

(h) in part (h), the heavy chain comprises a VH sequence having at least 95% sequence identity to the amino acid sequence of SEQ ID NO:127 and/or the light chain comprises a VL sequence having at least 95% sequence identity to the amino acid sequence of SEQ ID NO: 126;

(i) in part (i), the heavy chain comprises a VH sequence having at least 95% sequence identity to the amino acid sequence of SEQ ID NO:131 and/or the light chain comprises a VL sequence having at least 95% sequence identity to the amino acid sequence of SEQ ID NO:130;

(j) in part (j), the heavy chain comprises a VH sequence having at least 95% sequence identity to the amino acid sequence of SEQ ID NO:133 and/or the light chain comprises a VL sequence having at least 95% sequence identity to the amino acid sequence of SEQ ID NO:132; or (k) in part (a), the heavy chain comprises a VH sequence having at least 95% sequence identity to the amino acid sequence of SEQ ID NO:135 and/or the light chain comprises a VL sequence having at least 95% sequence identity to the amino acid sequence of SEQ ID NO:134.

7. The method of claim 6, wherein:

(a) in part (a), the heavy chain comprises a VH sequence of SEQ ID NO:113 and/or the light chain comprises a VL sequence of SEQ ID NO:112;

(b) in part (b), the heavy chain comprises a VH sequence of SEQ ID NO:111 and/or the light chain comprises a VL sequence of SEQ ID NO:110;

(c) in part (c), the heavy chain comprises a VH sequence of SEQ ID NO:117 and/or the light chain comprises a VL sequence of SEQ ID NO:116;

(d) in part (d), the heavy chain comprises a VH sequence of SEQ ID NO:119 and/or the light chain comprises a VL sequence of SEQ ID NO:118;

(e) in part (e), the heavy chain comprises a VH sequence of SEQ ID NO:121 and/or the light chain comprises a VL sequence of SEQ ID NO:120;

(f) in part (f), the heavy chain comprises a VH sequence of SEQ ID NO:123 and/or the light chain comprises a VL sequence of SEQ ID NO:122;

(g) in part (g), the heavy chain comprises a VH sequence of SEQ ID NO:125 and/or the light chain comprises a VL sequence of SEQ ID NO:124;

(h) in part (h), the heavy chain comprises a VH sequence of SEQ ID NO:127 and/or the light chain comprises a VL sequence of SEQ ID NO:126;

(i) in part (i), the heavy chain comprises a VH sequence of SEQ ID NO:131 and/or the light chain comprises a VL sequence of SEQ ID NO:130;

(j) in part (j), the heavy chain comprises a VH sequence of SEQ ID NO:133 and/or the light chain comprises a VL sequence of SEQ ID NO:132; or (k) in part (a), the heavy chain comprises a VH sequence of SEQ ID NO:135 and/or the light chain comprises a VL sequence of SEQ ID NO:134.

8. The method of claim 1, wherein the antibody is a monoclonal antibody.

9. The method of claim 1, wherein the antibody is a human, humanized, or chimeric antibody.

10. The method of claim 1, wherein the antibody is an antibody fragment that binds FcRH5.

11. The method of claim 1, wherein the antibody is an IgG1, IgG2a or IgG2b antibody.

12. The method of claim 1, wherein the antibody has one or more of the following characteristics: a) cross reactivity with full length human and cyno FcRH5, b) binds to endogenous FcRH5, c) does not cross react with FcRH5a, and d) does not cross react with another Ig-like domain of FcRH5.

13. The method of claim 4, wherein:

(a) in part (a), the heavy chain comprises a VH sequence having at least 95% sequence identity to the amino acid sequence of SEQ ID NO:113 and/or the light chain comprises a VL sequence having at least 95% sequence identity to the amino acid sequence of SEQ ID NO:112;

(b) in part (b), the heavy chain comprises a VH sequence having at least 95% sequence identity to the amino acid sequence of SEQ ID NO:111 and/or the light chain comprises a VL sequence having at least 95% sequence identity to the amino acid sequence of SEQ ID NO: 110;

(c) in part (c), the heavy chain comprises a VH sequence having at least 95% sequence identity to the amino acid sequence of SEQ ID NO:117 and/or the light chain comprises a VL sequence having at least 95% sequence identity to the amino acid sequence of SEQ ID NO:116;

(d) in part (d), the heavy chain comprises a VH sequence having at least 95% sequence identity to the amino acid sequence of SEQ ID NO:119 and/or the light chain comprises a VL sequence having at least 95% sequence identity to the amino acid sequence of SEQ ID NO:118;

(e) in part (e), the heavy chain comprises a VH sequence having at least 95% sequence identity to the amino acid sequence of SEQ ID NO:121 and/or the light chain comprises a VL sequence having at least 95% sequence identity to the amino acid sequence of SEQ ID NO:120;

(f) in part (f), the heavy chain comprises a VH sequence having at least 95% sequence identity to the amino acid sequence of SEQ ID NO:123 and/or the light chain comprises a VL sequence having at least 95% sequence identity to the amino acid sequence of SEQ ID NO:122;

(g) in part (g), the heavy chain comprises a VH sequence having at least 95% sequence identity to the amino acid sequence of SEQ ID NO:125 and/or the light chain comprises a VL sequence having at least 95% sequence identity to the amino acid sequence of SEQ ID NO:124;

(h) in part (h), the heavy chain comprises a VH sequence having at least 95% sequence identity to the amino acid sequence of SEQ ID NO:127 and/or the light chain comprises a VL sequence having at least 95% sequence identity to the amino acid sequence of SEQ ID NO: 126;

(i) in part (i), the heavy chain comprises a VH sequence having at least 95% sequence identity to the amino acid sequence of SEQ ID NO:131 and/or the light chain comprises a VL sequence having at least 95% sequence identity to the amino acid sequence of SEQ ID NO:130;

(j) in part (j), the heavy chain comprises a VH sequence having at least 95% sequence identity to the amino acid sequence of SEQ ID NO:133 and/or the light chain comprises a VL sequence having at least 95% sequence identity to the amino acid sequence of SEQ ID NO:132; or (k) in part (a), the heavy chain comprises a VH sequence having at least 95% sequence identity to the amino acid sequence of SEQ ID NO:135 and/or the light chain comprises a VL sequence having at least 95% sequence identity to the amino acid sequence of SEQ ID NO:134.

14. The method of claim 13, wherein:

(a) in part (a), the heavy chain comprises a VH sequence of SEQ ID NO:113 and/or the light chain comprises a VL sequence of SEQ ID NO:112;

(b) in part (b), the heavy chain comprises a VH sequence of SEQ ID NO:111 and/or the light chain comprises a VL sequence of SEQ ID NO:110;

(c) in part (c), the heavy chain comprises a VH sequence of SEQ ID NO:117 and/or the light chain comprises a VL sequence of SEQ ID NO:116;

(d) in part (d), the heavy chain comprises a VH sequence of SEQ ID NO:119 and/or the light chain comprises a VL sequence of SEQ ID NO:118;

(e) in part (e), the heavy chain comprises a VH sequence of SEQ ID NO:121 and/or the light chain comprises a VL sequence of SEQ ID NO:120;

(f) in part (f), the heavy chain comprises a VH sequence of SEQ ID NO:123 and/or the light chain comprises a VL sequence of SEQ ID NO:122;

(g) in part (g), the heavy chain comprises a VH sequence of SEQ ID NO:125 and/or the light chain comprises a VL sequence of SEQ ID NO:124;

(h) in part (h), the heavy chain comprises a VH sequence of SEQ ID NO:127 and/or the light chain comprises a VL sequence of SEQ ID NO:126;

(i) in part (i), the heavy chain comprises a VH sequence of SEQ ID NO:131 and/or the light chain comprises a VL sequence of SEQ ID NO:130;

(j) in part (j), the heavy chain comprises a VH sequence of SEQ ID NO:133 and/or the light chain comprises a VL sequence of SEQ ID NO:132; or (k) in part (a), the heavy chain comprises a VH sequence of SEQ ID NO:135 and/or the light chain comprises a VL sequence of SEQ ID NO:134.

* * * * *

SEQUENCE LISTING

```
<160> NUMBER OF SEQ ID NOS: 136

<210> SEQ ID NO 1
<211> LENGTH: 977
<212> TYPE: PRT
```

<213> ORGANISM: Homo sapiens

<400> SEQUENCE: 1

```
Met Leu Leu Trp Val Ile Leu Leu Val Leu Ala Pro Val Ser Gly Gln
1               5                   10                  15

Phe Ala Arg Thr Pro Arg Pro Ile Ile Phe Leu Gln Pro Pro Trp Thr
            20                  25                  30

Thr Val Phe Gln Gly Glu Arg Val Thr Leu Thr Cys Lys Gly Phe Arg
        35                  40                  45

Phe Tyr Ser Pro Gln Lys Thr Lys Trp Tyr His Arg Tyr Leu Gly Lys
    50                  55                  60

Glu Ile Leu Arg Glu Thr Pro Asp Asn Ile Leu Glu Val Gln Glu Ser
65                  70                  75                  80

Gly Glu Tyr Arg Cys Gln Ala Gln Gly Ser Pro Leu Ser Ser Pro Val
                85                  90                  95

His Leu Asp Phe Ser Ser Ala Ser Leu Ile Leu Gln Ala Pro Leu Ser
            100                 105                 110

Val Phe Glu Gly Asp Ser Val Val Leu Arg Cys Arg Ala Lys Ala Glu
        115                 120                 125

Val Thr Leu Asn Asn Thr Ile Tyr Lys Asn Asp Asn Val Leu Ala Phe
    130                 135                 140

Leu Asn Lys Arg Thr Asp Phe His Ile Pro His Ala Cys Leu Lys Asp
145                 150                 155                 160

Asn Gly Ala Tyr Arg Cys Thr Gly Tyr Lys Glu Ser Cys Cys Pro Val
                165                 170                 175

Ser Ser Asn Thr Val Lys Ile Gln Val Gln Glu Pro Phe Thr Arg Pro
            180                 185                 190

Val Leu Arg Ala Ser Ser Phe Gln Pro Ile Ser Gly Asn Pro Val Thr
        195                 200                 205

Leu Thr Cys Glu Thr Gln Leu Ser Leu Glu Arg Ser Asp Val Pro Leu
    210                 215                 220

Arg Phe Arg Phe Phe Arg Asp Asp Gln Thr Leu Gly Leu Gly Trp Ser
225                 230                 235                 240

Leu Ser Pro Asn Phe Gln Ile Thr Ala Met Trp Ser Lys Asp Ser Gly
                245                 250                 255

Phe Tyr Trp Cys Lys Ala Ala Thr Met Pro Tyr Ser Val Ile Ser Asp
            260                 265                 270

Ser Pro Arg Ser Trp Ile Gln Val Gln Ile Pro Ala Ser His Pro Val
        275                 280                 285

Leu Thr Leu Ser Pro Glu Lys Ala Leu Asn Phe Glu Gly Thr Lys Val
    290                 295                 300

Thr Leu His Cys Glu Thr Gln Glu Asp Ser Leu Arg Thr Leu Tyr Arg
305                 310                 315                 320

Phe Tyr His Glu Gly Val Pro Leu Arg His Lys Ser Val Arg Cys Glu
                325                 330                 335

Arg Gly Ala Ser Ile Ser Phe Ser Leu Thr Thr Glu Asn Ser Gly Asn
            340                 345                 350

Tyr Tyr Cys Thr Ala Asp Asn Gly Leu Gly Ala Lys Pro Ser Lys Ala
        355                 360                 365

Val Ser Leu Ser Val Thr Val Pro Val Ser His Pro Val Leu Asn Leu
    370                 375                 380

Ser Ser Pro Glu Asp Leu Ile Phe Glu Gly Ala Lys Val Thr Leu His
385                 390                 395                 400
```

-continued

```
Cys Glu Ala Gln Arg Gly Ser Leu Pro Ile Leu Tyr Gln Phe His His
                405                 410                 415

Glu Gly Ala Ala Leu Glu Arg Arg Ser Ala Asn Ser Ala Gly Gly Val
            420                 425                 430

Ala Ile Ser Phe Ser Leu Thr Ala Glu His Ser Gly Asn Tyr Tyr Cys
        435                 440                 445

Thr Ala Asp Asn Gly Phe Gly Pro Gln Arg Ser Lys Ala Val Ser Leu
    450                 455                 460

Ser Val Thr Val Pro Val Ser His Pro Val Leu Thr Leu Ser Ser Ala
465                 470                 475                 480

Glu Ala Leu Thr Phe Glu Gly Ala Thr Val Thr Leu His Cys Glu Val
                485                 490                 495

Gln Arg Gly Ser Pro Gln Ile Leu Tyr Gln Phe Tyr His Glu Asp Met
            500                 505                 510

Pro Leu Trp Ser Ser Ser Thr Pro Ser Val Gly Arg Val Ser Phe Ser
        515                 520                 525

Phe Ser Leu Thr Glu Gly His Ser Gly Asn Tyr Tyr Cys Thr Ala Asp
    530                 535                 540

Asn Gly Phe Gly Pro Gln Arg Ser Glu Val Val Ser Leu Phe Val Thr
545                 550                 555                 560

Val Pro Val Ser Arg Pro Ile Leu Thr Leu Arg Val Pro Arg Ala Gln
                565                 570                 575

Ala Val Val Gly Asp Leu Leu Glu Leu His Cys Glu Ala Pro Arg Gly
            580                 585                 590

Ser Pro Pro Ile Leu Tyr Trp Phe Tyr His Glu Asp Val Thr Leu Gly
        595                 600                 605

Ser Ser Ser Ala Pro Ser Gly Gly Glu Ala Ser Phe Asn Leu Ser Leu
    610                 615                 620

Thr Ala Glu His Ser Gly Asn Tyr Ser Cys Glu Ala Asn Asn Gly Leu
625                 630                 635                 640

Val Ala Gln His Ser Asp Thr Ile Ser Leu Ser Val Ile Val Pro Val
                645                 650                 655

Ser Arg Pro Ile Leu Thr Phe Arg Ala Pro Arg Ala Gln Ala Val Val
            660                 665                 670

Gly Asp Leu Leu Glu Leu His Cys Glu Ala Leu Arg Gly Ser Ser Pro
        675                 680                 685

Ile Leu Tyr Trp Phe Tyr His Glu Asp Val Thr Leu Gly Lys Ile Ser
    690                 695                 700

Ala Pro Ser Gly Gly Gly Ala Ser Phe Asn Leu Ser Leu Thr Thr Glu
705                 710                 715                 720

His Ser Gly Ile Tyr Ser Cys Glu Ala Asp Asn Gly Leu Glu Ala Gln
                725                 730                 735

Arg Ser Glu Met Val Thr Leu Lys Val Ala Val Pro Val Ser Arg Pro
            740                 745                 750

Val Leu Thr Leu Arg Ala Pro Gly Thr His Ala Ala Val Gly Asp Leu
        755                 760                 765

Leu Glu Leu His Cys Glu Ala Leu Arg Gly Ser Pro Leu Ile Leu Tyr
    770                 775                 780

Arg Phe Phe His Glu Asp Val Thr Leu Gly Asn Arg Ser Ser Pro Ser
785                 790                 795                 800

Gly Gly Ala Ser Leu Asn Leu Ser Leu Thr Ala Glu His Ser Gly Asn
                805                 810                 815

Tyr Ser Cys Glu Ala Asp Asn Gly Leu Gly Ala Gln Arg Ser Glu Thr
```

```
            820                 825                 830

Val Thr Leu Tyr Ile Thr Gly Leu Thr Ala Asn Arg Ser Gly Pro Phe
        835                 840                 845

Ala Thr Gly Val Ala Gly Gly Leu Leu Ser Ile Ala Gly Leu Ala Ala
    850                 855                 860

Gly Ala Leu Leu Leu Tyr Cys Trp Leu Ser Arg Lys Ala Gly Arg Lys
865                 870                 875                 880

Pro Ala Ser Asp Pro Ala Arg Ser Pro Ser Asp Ser Asp Ser Gln Glu
                885                 890                 895

Pro Thr Tyr His Asn Val Pro Ala Trp Glu Glu Leu Gln Pro Val Tyr
            900                 905                 910

Thr Asn Ala Asn Pro Arg Gly Glu Asn Val Val Tyr Ser Glu Val Arg
        915                 920                 925

Ile Ile Gln Glu Lys Lys Lys His Ala Val Ala Ser Asp Pro Arg His
    930                 935                 940

Leu Arg Asn Lys Gly Ser Pro Ile Ile Tyr Ser Glu Val Lys Val Ala
945                 950                 955                 960

Ser Thr Pro Val Ser Gly Ser Leu Phe Leu Ala Ser Ser Ala Pro His
                965                 970                 975

Arg


<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Ala Ser Gln Asn Val Ile Thr Asn Val Ala
1               5                   10


<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Ala Ser Gln Asp Val Ser Asn Ile Val Val
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Asn Ile Arg Asn Asn Leu His
1               5                   10


<210> SEQ ID NO 5
<211> LENGTH: 11
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 5

Arg Ala Ser Gln Ser Ile Ser Asn Asn Leu His
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Glu Asn Ile Tyr Ser Asn Leu Ala
1               5                   10

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ser Ser Gln Ser Leu Val His Arg Asn Gly Asn Thr Tyr Leu His
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Glu Asn Ile Tyr Ser Asn Leu Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Ser Glu Asn Ile Tyr Ser Asn Leu Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Ser Gln Ser Ile Ser Asn Asn Leu His
1               5                   10

```
<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Ser Gln Asn Ile Arg Asn Asn Leu His
1               5                   10


<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ser Ser Thr Gly Thr Val Thr Thr Ser Asn Phe Ala Asn
1               5                   10


<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ala Ser Gln Asp Val Gly Thr Ala Val Ala
1               5                   10


<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Ala Ser Tyr Arg Tyr Ser
1               5


<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Ala Ser Tyr Arg Tyr Thr
1               5


<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Phe Thr Ser Gln Ser Ile Ser
1 5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Phe Ala Ser Gln Ser Ile Ser
1 5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gly Ala Ala Asn Leu Ala Glu
1 5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Lys Val Ser Asn Arg Phe Ser
1 5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Gly Ala Ala Asn Leu Ala Glu
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Gly Ala Ala Asn Leu Ala Glu
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Phe Ala Ser Gln Ser Ile Ser
1 5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Phe Ala Ser Gln Ser Met Ser
1 5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Thr Ser Asn Arg Ala Pro
1 5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Trp Pro Ser Thr Arg His Thr
1 5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

Gln Gln Tyr Thr Asn Tyr Pro Met Trp Thr
1 5 10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Gln Gln His Tyr Ser Ser Pro Tyr Thr
1 5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Gln Gln Ser Asn Asn Trp Pro Gln Tyr Thr
1 5 10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Gln Gln Ser Asn Asn Trp Pro Gln Tyr Thr
1 5 10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Gln His Phe Trp Gly Ile Pro Trp Thr
1 5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Ser Gln Ser Thr His Val Pro Pro Thr
1 5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gln His Phe Trp Gly Ile Pro Trp Thr
1 5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 33

Gln His Phe Trp Gly Ile Pro Trp Thr
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Gln Gln Ser Asn Asn Trp Pro Gln Tyr Thr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gln Gln Ser Asn Asn Trp Pro Gln Tyr Thr
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Val Leu Trp Cys Ser Asn Leu Trp Val
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 37

Gln Gln Phe Ser Ser Leu Pro His Thr
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Ala Tyr Ile Met Asn
1               5

<210> SEQ ID NO 39
<211> LENGTH: 5
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 39

Arg Phe Gly Val His
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Tyr Tyr Met Lys
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Asp Tyr Tyr Met Lys
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Glu Tyr Thr Ile His
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Tyr Trp Ile Asn
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Glu Tyr Thr Ile His
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Glu Tyr Thr Ile His
1 5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Asp Tyr Tyr Met Lys
1 5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Asp Tyr Tyr Met Lys
1 5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Asn Tyr Leu Ile Glu
1 5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Ala Tyr Phe Met Asn
1 5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Gly Tyr Ser Phe Thr Ala Tyr Ile Met Asn
1 5 10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gly Phe Ser Leu Thr Arg Phe Gly Val His
1 5 10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Gly Tyr Thr Phe Thr Asp Tyr Tyr Met Lys
1 5 10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Gly Tyr Thr Phe Thr Asp Tyr Tyr Met Lys
1 5 10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Gly Tyr Thr Phe Thr Glu Tyr Thr Ile His
1 5 10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Gly Tyr Thr Phe Ile Ser Tyr Trp Ile Asn
1 5 10

<210> SEQ ID NO 56
<211> LENGTH: 10

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Gly Tyr Thr Phe Thr Glu Tyr Thr Ile His
1 5 10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Tyr Thr Phe Thr Glu Tyr Thr Ile His
1 5 10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Gly Tyr Thr Phe Thr Asp Tyr Tyr Met Lys
1 5 10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Gly Tyr Thr Phe Thr Asp Tyr Tyr Met Lys
1 5 10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Gly Tyr Ala Phe Thr Asn Tyr Leu Ile Glu
1 5 10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Phe Ser Phe Thr Ala Tyr Phe Met Asn 1 5 10

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Leu Ile Asn Pro Tyr Asn Gly Glu Thr Thr Tyr Asn Gln Lys Phe Lys
1 5 10 15

Gly

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Val Ile Trp Arg Gly Gly Ser Thr Asp Tyr Asn Ala Ala Phe Met Ser
1 5 10 15

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Asp Ile Asn Pro Asn Asn Gly Glu Thr Phe Tyr Ser Gln Lys Phe Lys
1 5 10 15

Gly

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Asp Ile Asn Pro Tyr Asn Gly Glu Thr Phe Tyr Asn Gln Lys Leu Lys
1 5 10 15

Gly

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Gly Ile Asn Pro Asn Asn Asp Ala Val Ser Tyr Asn Gln Arg Phe Arg
1 5 10 15

Gly

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Asn Ile Tyr Pro Ser Asp Ser Tyr Thr Asn Tyr Asn Gln Lys Phe Lys
1 5 10 15

Asp

<210> SEQ ID NO 68
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Gly Ile Asn Pro Asn Asn Asp Ala Ile Ser Tyr Asn Gln Lys Phe Arg
1 5 10 15

Gly

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Gly Ile Asn Pro Asn Asn Asp Ala Ile Ser Tyr Asn Gln Lys Phe Arg
1 5 10 15

Gly

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Asp Ile Asn Pro Tyr Asn Gly Asp Thr Phe Tyr Asn Gln Lys Phe Lys
1 5 10 15

Asp

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Asp Ile Asn Pro Asn Asn Gly Glu Thr Phe Tyr Asn Gln Lys Phe Lys
1 5 10 15

Gly

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Val Ile Asn Pro Gly Ser Gly Gly Thr Asn Tyr Asn Glu Lys Phe Lys
1 5 10 15

Gly

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Arg Ile Asn Pro Tyr Asn Gly Glu Thr Phe Phe Asn Gln Asn Phe Lys
1 5 10 15

Asp

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Gly Leu Ile Asn Pro Tyr Asn Gly Glu Thr Thr Tyr Asn Gln Lys Phe
1 5 10 15

Lys Gly

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Gly Val Ile Trp Arg Gly Gly Ser Thr Asp Tyr Asn Ala Ala Phe Met
1 5 10 15

Ser

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Gly Asp Ile Asn Pro Asn Asn Gly Glu Thr Phe Tyr Ser Gln Lys Phe
1 5 10 15

-continued

Lys Gly

<210> SEQ ID NO 77
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Gly Asp Ile Asn Pro Tyr Asn Gly Glu Thr Phe Tyr Asn Gln Lys Leu
1 5 10 15

Lys Gly

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Gly Gly Ile Asn Pro Asn Asn Asp Ala Val Ser Tyr Asn Gln Arg Phe
1 5 10 15

Arg Gly

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 79

Gly Asn Ile Tyr Pro Ser Asp Ser Tyr Thr Asn Tyr Asn Gln Lys Phe
1 5 10 15

Lys Asp

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 80

Gly Gly Ile Asn Pro Asn Asn Asp Ala Ile Ser Tyr Asn Gln Lys Phe
1 5 10 15

Arg Gly

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 81

Gly Gly Ile Asn Pro Asn Asn Asp Ala Ile Ser Tyr Asn Gln Lys Phe 1 5 10 15

Arg Gly

<210> SEQ ID NO 82
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 82

Gly Asp Ile Asn Pro Tyr Asn Gly Asp Thr Phe Tyr Asn Gln Lys Phe
1 5 10 15

Lys Asp

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 83

Gly Asp Ile Asn Pro Asn Asn Gly Glu Thr Phe Tyr Asn Gln Lys Phe
1 5 10 15

Lys Gly

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Gly Val Ile Asn Pro Gly Ser Gly Gly Thr Asn Tyr Asn Glu Lys Phe
1 5 10 15

Lys Gly

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 85

Gly Arg Ile Asn Pro Tyr Asn Gly Glu Thr Phe Phe Asn Gln Asn Phe
1 5 10 15

Lys Asp

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Gly Leu Tyr Trp Phe Pro Tyr
1 5

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 87

His Tyr Tyr Gly Ser Ser Asp Tyr Ala Leu Asp Asn
1 5 10

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 88

Gly Leu Tyr Arg Phe Asp Tyr
1 5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Gly Leu Tyr Phe Phe Ala Tyr
1 5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Leu Gly Arg Gly Tyr Tyr Phe Asp Tyr
1 5

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Ser Leu Tyr Gly Tyr Asp Ala Ser Tyr Phe Asp Tyr
1 5 10

<210> SEQ ID NO 92
<211> LENGTH: 9
<212> TYPE: PRT
<213> ORGANISM: Artificial Sequence
<220> FEATURE:

<223> OTHER INFORMATION: Description of Artificial Sequence: Synthetic peptide

<400> SEQUENCE: 92

Leu Gly Arg Gly Tyr Tyr Phe Asp Tyr
1 5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Leu Gly Arg Gly Tyr Tyr Phe Asp Tyr
1 5

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 94

Gly Leu Tyr Phe Phe His Tyr
1 5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 95

Gly Leu Tyr Arg Phe Asp Tyr
1 5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 96

Thr Arg Asn Tyr Gly Tyr Val Ile Asp Tyr
1 5 10

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

Gly Leu Tyr Tyr Leu Asn Tyr
1 5

-continued

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Ala Arg Gly Leu Tyr Trp Phe Pro Tyr
1 5

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Ser Asn His Tyr Tyr Gly Ser Ser Asp Tyr Ala Leu Asp Asn
1 5 10

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 100

Ala Arg Gly Leu Tyr Arg Phe Asp Tyr
1 5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Ala Arg Gly Leu Tyr Phe Phe Ala Tyr
1 5

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Ala Lys Leu Gly Arg Gly Tyr Tyr Phe Asp Tyr
1 5 10

<210> SEQ ID NO 103
<211> LENGTH: 14
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 103

Thr Arg Ser Leu Tyr Gly Tyr Asp Ala Ser Tyr Phe Asp Tyr
1 5 10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Ala Lys Leu Gly Arg Gly Tyr Tyr Phe Asp Tyr
1 5 10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Ala Lys Leu Gly Arg Gly Tyr Tyr Phe Asp Tyr
1 5 10

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Ala Arg Gly Leu Tyr Phe Phe His Tyr
1 5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Ala Arg Gly Leu Tyr Arg Phe Asp Tyr
1 5

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Ala Arg Thr Arg Asn Tyr Gly Tyr Val Ile Asp Tyr
1 5 10

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Arg Gly Leu Tyr Tyr Leu Asn Tyr
1               5

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Gln Arg Phe Met Ser Thr Ser Leu Gly
1               5                   10                  15

Asp Arg Val Ser Val Thr Cys Lys Ala Ser Gln Asn Val Ile Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Thr Asn Tyr Pro Met
                85                  90                  95

Trp Thr Phe Gly Gly Gly Thr Arg Leu Glu Ile Lys Arg Thr Val Ala
            100                 105                 110

<210> SEQ ID NO 111
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Val Gln Leu Gln Gln Ser Gly Pro Glu Leu Val Lys Pro Gly Ala
1               5                   10                  15

Ser Met Lys Ile Ser Cys Glu Ala Ser Gly Tyr Ser Phe Thr Ala Tyr
            20                  25                  30

Ile Met Asn Trp Val Lys Gln Ser Arg Gly Lys Asn Leu Glu Trp Ile
        35                  40                  45

Gly Leu Ile Asn Pro Tyr Asn Gly Glu Thr Thr Tyr Asn Gln Lys Phe
    50                  55                  60

Lys Gly Lys Ala Thr Leu Thr Val Asp Gln Ser Ser Ser Thr Ala Tyr
65                  70                  75                  80

Met Glu Leu Leu Ser Leu Thr Ser Glu Asp Ser Ala Val Tyr Phe Cys
                85                  90                  95

Ala Arg Gly Leu Tyr Trp Phe Pro Tyr Trp Gly Gln Gly Thr Leu Val
            100                 105                 110

Thr Val Ser Ala Ala Ser Thr Lys Gly Pro Ser Val Phe Pro Leu Ala
        115                 120                 125

Pro

-continued

<210> SEQ ID NO 112
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Asp Ile Val Met Thr Gln Ser His Lys Ile Met Ser Thr Ser Val Gly
1               5                   10                  15

Asp Arg Val Ser Ile Thr Cys Lys Ala Ser Gln Asp Val Ser Asn Ile
            20                  25                  30

Val Val Trp Phe Gln Gln Lys Pro Gly Gln Ser Pro Asn Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Tyr
                85                  90                  95

Thr Phe Gly Gly Gly Thr Lys Leu Glu Ile Lys Arg Thr Val Ala Ala
            100                 105                 110
```

<210> SEQ ID NO 113
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Glu Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Arg Phe
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Thr Lys Asp Asn Ser Lys Ser Gln Val Phe Phe
65                  70                  75                  80

Lys Leu Asn Ser Leu Lys Val Asp Asp Thr Ala Ile Tyr Tyr Cys Ser
                85                  90                  95

Asn His Tyr Tyr Gly Ser Ser Asp Tyr Ala Leu Asp Asn Trp Gly Gln
            100                 105                 110

Gly Thr Ser Val Thr Val Ser Ser Ala Ser Thr Lys Gly Pro Ser Val
        115                 120                 125

Phe Pro Leu Ala Pro
    130
```

<210> SEQ ID NO 114
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Glu Ile Val Leu Thr Gln Ser Pro Ala Thr Leu Ser Val Thr Pro Gly
1               5                   10                  15

Asp Ser Val Ser Leu Ser Cys Arg Ala Ser Gln Asn Ile Arg Asn Asn
            20                  25                  30

Leu His Trp Tyr Gln Gln Lys Ser His Glu Ser Pro Arg Leu Leu Ile
        35                  40                  45

Lys Phe Thr Ser Gln Ser Ile Ser Gly Ile Pro Ser Arg Phe Thr Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Asn Trp Pro Gln
                85                  90                  95

Tyr Thr Phe Gly Gly Gly Thr Lys Leu Glu Ile Lys Arg Thr Val Ala
            100                 105                 110

Ala


<210> SEQ ID NO 115
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Gln Gln Ser Gly Pro Glu Leu Trp Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Thr His Gly Lys Ser Leu Glu Trp Ile
        35                  40                  45

Gly Asp Ile Asn Pro Asn Asn Gly Glu Thr Phe Tyr Ser Gln Lys Phe
    50                  55                  60

Lys Gly Lys Ala Thr Leu Thr Val Asp Lys Ser Ser Thr Thr Ala Tyr
65                  70                  75                  80

Met Gln Leu Asn Ser Leu Thr Ser Glu Asp Ser Ala Val Tyr Tyr Cys
                85                  90                  95

Ala Arg Gly Leu Tyr Arg Phe Asp Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro


<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Asp Ile Gln Met Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
```

```
        35                  40                  45

Lys Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Asn Trp Pro Gln
                85                  90                  95

Tyr Thr Phe Gly Gly Gly Thr Lys Leu Glu Leu Lys Arg Thr Val Ala
            100                 105                 110

Ala


<210> SEQ ID NO 117
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Val Gln Leu Gln Gln Ser Gly Pro Glu Leu Val Lys Ser Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Tyr Asn Gly Glu Thr Phe Tyr Asn Gln Lys Leu
    50                  55                  60

Lys Gly Lys Ala Thr Leu Thr Val Asp Lys Ser Ser Asn Thr Val Phe
65                  70                  75                  80

Met Gln Leu Asn Ser Leu Thr Ser Glu Asp Ser Ala Val Tyr Tyr Cys
                85                  90                  95

Ala Arg Gly Leu Tyr Phe Phe Ala Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro


<210> SEQ ID NO 118
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Leu Lys Gln Gly Lys Ser Pro Gln Leu Leu Val
        35                  40                  45

Tyr Gly Ala Ala Asn Leu Ala Glu Gly Val Pro Ser Arg Ile Ser Gly
    50                  55                  60

Ser Gly Ser Gly Thr Gln Tyr Ser Leu Lys Ile Asn Ser Leu Gln Ser
65                  70                  75                  80
```

-continued

```
Glu Asp Phe Gly Thr Tyr Tyr Cys Gln His Phe Trp Gly Ile Pro Trp
                85                  90                  95

Thr Phe Gly Gly Gly Thr Lys Leu Glu Ile Lys Arg Thr Val Ala Ala
            100                 105                 110


<210> SEQ ID NO 119
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Ile His Trp Val Lys Gln Ser His Gly Lys Ser Leu Glu Arg Ile
        35                  40                  45

Gly Gly Ile Asn Pro Asn Asn Asp Ala Val Ser Tyr Asn Gln Arg Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Lys Leu Gly Arg Gly Tyr Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro
    130


<210> SEQ ID NO 120
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Asp Ile Gln Met Thr Gln Thr Pro Leu Ser Leu Pro Val Thr Leu Gly
1               5                   10                  15

Asp Gln Ala Ser Ile Ser Cys Arg Ser Ser Gln Ser Leu Val His Arg
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Thr Phe Gly Gly Gly Thr Lys Leu Glu Leu Lys
            100                 105                 110

Arg Thr Val Ala Ala
        115
```

<210> SEQ ID NO 121
<211> LENGTH: 134
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 121

Gln Val Gln Leu Gln Gln Pro Gly Ala Glu Leu Val Arg Pro Gly Ala
1 5 10 15

Ser Val Lys Leu Ser Cys Lys Thr Ser Gly Tyr Thr Phe Ile Ser Tyr
20 25 30

Trp Ile Asn Trp Val Lys Gln Arg Pro Gly Gln Gly Leu Glu Trp Ile
35 40 45

Gly Asn Ile Tyr Pro Ser Asp Ser Tyr Thr Asn Tyr Asn Gln Lys Phe
50 55 60

Lys Asp Lys Ala Thr Leu Thr Val Asp Thr Ser Ser Ser Thr Ala Tyr
65 70 75 80

Met Gln Leu Thr Ser Pro Thr Ser Glu Asp Ser Ala Val Tyr Tyr Cys
85 90 95

Thr Arg Ser Leu Tyr Gly Tyr Asp Ala Ser Tyr Phe Asp Tyr Trp Gly
100 105 110

Gln Gly Thr Thr Leu Thr Val Ser Ser Ala Ser Thr Lys Gly Pro Ser
115 120 125

Val Phe Pro Leu Ala Pro
130

<210> SEQ ID NO 122
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 122

Asp Ile Val Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Asn
20 25 30

Leu Ala Trp Tyr Gln Leu Lys Gln Gly Lys Ser Pro Gln Leu Leu Val
35 40 45

Tyr Gly Ala Ala Asn Leu Ala Glu Gly Val Pro Ser Arg Ile Ser Gly
50 55 60

Ser Gly Ser Gly Thr Gln Tyr Ser Leu Lys Ile Asn Ser Leu Gln Ser
65 70 75 80

Glu Asp Phe Gly Thr Tyr Tyr Cys Gln His Phe Trp Gly Ile Pro Trp
85 90 95

Thr Phe Gly Gly Gly Thr Lys Leu Glu Ile Lys Arg Thr Val Ala Ala
100 105 110

<210> SEQ ID NO 123
<211> LENGTH: 131
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 123

Gln Val Gln Leu Gln Gln Ser Gly Pro Glu Leu Val Lys Pro Gly Ala
1 5 10 15

Ser Val Lys Ile Ser Cys Lys Thr Ser Gly Tyr Thr Phe Thr Glu Tyr
20 25 30

Thr Ile His Trp Val Lys Gln Ser His Gly Lys Ser Leu Glu Arg Ile
35 40 45

Gly Gly Ile Asn Pro Asn Asn Asp Ala Ile Ser Tyr Asn Gln Lys Phe
50 55 60

Arg Gly Lys Ala Thr Leu Thr Val Asp Lys Ser Ser Ser Thr Ala Tyr
65 70 75 80

Met Glu Leu Arg Ser Leu Thr Ser Glu Asp Ser Ala Val Tyr Tyr Cys
85 90 95

Ala Lys Leu Gly Arg Gly Tyr Tyr Phe Asp Tyr Trp Gly Arg Gly Thr
100 105 110

Thr Leu Thr Val Ser Ser Ala Ser Thr Lys Gly Pro Ser Val Phe Pro
115 120 125

Leu Ala Pro
130

<210> SEQ ID NO 124
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Asp Ile Val Met Thr Gln Ser Pro Ala Ser Leu Ser Ala Ser Val Gly
1 5 10 15

Glu Thr Val Thr Ile Thr Cys Arg Ala Ser Glu Asn Ile Tyr Ser Asn
20 25 30

Leu Ala Trp Tyr Gln Leu Lys Gln Gly Lys Ser Pro Gln Leu Leu Val
35 40 45

Tyr Gly Ala Ala Asn Leu Ala Glu Gly Val Pro Ser Arg Ile Ser Gly
50 55 60

Ser Gly Ser Gly Thr Gln Tyr Ser Leu Lys Ile Asn Ser Leu Gln Ser
65 70 75 80

Glu Asp Phe Gly Thr Tyr Tyr Cys Gln His Phe Trp Gly Ile Pro Trp
85 90 95

Thr Phe Gly Gly Gly Thr Lys Leu Glu Ile Lys Arg Thr Val Ala Ala
100 105 110

<210> SEQ ID NO 125
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Glu Val Gln Leu Gln Gln Ser Gly Pro Glu Leu Val Lys Pro Gly Ala
1 5 10 15

Ser Val Lys Ile Ser Cys Lys Thr Ser Gly Tyr Thr Phe Thr Glu Tyr
20 25 30

Thr Ile His Trp Val Lys Gln Ser His Gly Lys Ser Leu Glu Arg Ile

```
        35                  40                  45

Gly Gly Ile Asn Pro Asn Asn Asp Ala Ile Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Lys Leu Gly Arg Gly Tyr Tyr Phe Asp Tyr Trp Gly Arg Gly Thr
            100                 105                 110

Thr Leu Thr Val Ser Ser Ala Ser Thr Lys Gly Pro Ser Val Phe Pro
        115                 120                 125

Leu Ala Pro
    130


<210> SEQ ID NO 126
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Asp Ile Val Leu Ile Gln Ser Pro Ala Thr Leu Ser Val Thr Leu Gly
1               5                   10                  15

Gly Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Arg Gly
    50                  55                  60

Ser Gly Ser Gly Thr Asp Phe Thr Leu Thr Ile Asn Ser Val Glu Thr
65                  70                  75                  80

Glu Asp Phe Gly Ile Tyr Phe Cys Gln Gln Ser Asn Asn Trp Pro Gln
                85                  90                  95

Tyr Thr Phe Gly Gly Gly Thr Lys Leu Glu Leu Lys Arg Thr Val Ala
            100                 105                 110

Ala


<210> SEQ ID NO 127
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Arg Gln Asn His Gly Lys Arg Leu Glu Trp Ile
        35                  40                  45

Gly Asp Ile Asn Pro Tyr Asn Gly Asp Thr Phe Tyr Asn Gln Lys Phe
    50                  55                  60

Lys Asp Lys Ala Thr Leu Thr Val Asp Lys Ser Ser Ser Thr Ala Tyr
65                  70                  75                  80
```

```
Met Gln Phe Asn Ser Leu Thr Ser Glu Asp Ser Ala Val Tyr Tyr Cys
                85                  90                  95

Ala Arg Gly Leu Tyr Phe Phe His Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro


<210> SEQ ID NO 128
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Asp Ile Val Leu Thr Gln Ser Pro Ala Asn Leu Ser Val Ile Pro Gly
1               5                   10                  15

Asp Ser Val Ser Leu Ser Cys Arg Ala Ser Gln Asn Ile Arg Asn Asn
            20                  25                  30

Leu His Trp Tyr Gln Gln Lys Ser Gln Glu Ser Pro Arg Leu Leu Ile
        35                  40                  45

Lys Phe Ala Ser Gln Ser Met Ser Gly Thr Pro Ser Arg Phe Thr Gly
    50                  55                  60

Ser Gly Ser Gly Thr Asp Phe Thr Leu Thr Ile Asn Thr Val Glu Thr
65                  70                  75                  80

Glu Asp Phe Gly Met Tyr Phe Cys Gln Gln Ser Asn Asn Trp Pro Gln
                85                  90                  95

Tyr Thr Phe Gly Gly Gly Thr Lys Leu Glu Ile Lys Arg Thr Val Ala
            100                 105                 110

Ala


<210> SEQ ID NO 129
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Gln Gln Ser Gly Pro Glu Leu Trp Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Ile Asn Pro Asn Asn Gly Glu Thr Phe Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Asn Ser Leu Thr Thr Glu Asp Ser Ala Val Tyr Tyr Cys
                85                  90                  95

Ala Arg Gly Leu Tyr Arg Phe Asp Tyr Trp Gly Gln Gly Thr Thr Leu
            100                 105                 110

Thr Val Ser Ser Ala Ala Ser Thr Lys Gly Pro Ser Val Phe Pro Leu
```

115 120 125

Ala Pro
130

<210> SEQ ID NO 130
<211> LENGTH: 115
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

Gln Ala Val Val Thr Gln Glu Ser Ala Leu Thr Thr Ser Pro Gly Glu
1 5 10 15

Thr Val Thr Leu Thr Cys Arg Ser Ser Thr Gly Thr Val Thr Thr Ser
20 25 30

Asn Phe Ala Asn Trp Val Gln Glu Lys Pro Asp His Leu Phe Thr Gly
35 40 45

Leu Ile Gly Gly Thr Ser Asn Arg Ala Pro Gly Val Pro Ala Arg Phe
50 55 60

Ser Gly Ser Leu Ile Gly Asp Lys Ala Ala Leu Thr Ile Thr Gly Ala
65 70 75 80

Gln Thr Glu Asp Glu Ala Ile Tyr Phe Cys Val Leu Trp Cys Ser Asn
85 90 95

Leu Trp Val Phe Gly Gly Gly Thr Lys Leu Thr Val Leu Gly Gln Pro
100 105 110

Lys Ala Ala
115

<210> SEQ ID NO 131
<211> LENGTH: 132
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 131

Gln Val Gln Leu Gln Gln Ser Gly Ala Asp Leu Val Arg Pro Gly Thr
1 5 10 15

Ser Val Lys Val Ser Cys Lys Ala Ser Gly Tyr Ala Phe Thr Asn Tyr
20 25 30

Leu Ile Glu Trp Val Lys Gln Arg Pro Gly Gln Gly Leu Glu Trp Ile
35 40 45

Gly Val Ile Asn Pro Gly Ser Gly Gly Thr Asn Tyr Asn Glu Lys Phe
50 55 60

Lys Gly Lys Ala Thr Leu Thr Ala Asp Lys Ser Ser Ser Thr Ala Tyr
65 70 75 80

Met Gln Leu Ser Ser Leu Thr Ser Asp Asp Ser Ala Val Tyr Phe Cys
85 90 95

Ala Arg Thr Arg Asn Tyr Gly Tyr Val Ile Asp Tyr Trp Gly Gln Gly
100 105 110

Thr Thr Leu Thr Val Ser Ser Ala Ser Thr Lys Gly Pro Ser Val Phe
115 120 125

Pro Leu Ala Pro
130

<210> SEQ ID NO 132
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 132

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Phe Trp Pro Ser Thr Arg His Thr Gly Val Pro Asp Arg Phe Thr Gly
    50                  55                  60

Ser Gly Ser Gly Thr Asp Phe Thr Leu Thr Ile Gly Asn Val Gln Ser
65                  70                  75                  80

Glu Asp Leu Ala Asp Tyr Phe Cys Gln Gln Phe Ser Ser Leu Pro His
                85                  90                  95

Thr Phe Gly Gly Gly Thr Lys Leu Glu Ile Lys Arg Thr Val Ala Ala
            100                 105                 110
```

<210> SEQ ID NO 133
<211> LENGTH: 129
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 133

```
Gln Val Gln Leu Gln Gln Ser Gly Pro Glu Leu Val Lys Pro Gly Ala
1               5                   10                  15

Ser Val Lys Ile Ser Cys Lys Ala Ser Gly Phe Ser Phe Thr Ala Tyr
            20                  25                  30

Phe Met Asn Trp Val Lys Gln Ser His Gly Lys Ser Pro Glu Trp Ile
        35                  40                  45

Gly Arg Ile Asn Pro Tyr Asn Gly Glu Thr Phe Phe Asn Gln Asn Phe
    50                  55                  60

Lys Asp Lys Ala Thr Leu Thr Val Asp Lys Ser Ser Asn Thr Ala His
65                  70                  75                  80

Met Glu Leu Leu Ser Leu Thr Ser Asp Asp Ser Ala Val Tyr Tyr Cys
                85                  90                  95

Gly Arg Gly Leu Tyr Tyr Leu Asn Tyr Trp Gly Gln Gly Thr Thr Leu
            100                 105                 110

Thr Val Ser Ser Ala Ser Thr Lys Gly Pro Ser Val Phe Pro Leu Ala
        115                 120                 125

Pro
```

<210> SEQ ID NO 134
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 134

-continued

```
Asp Ile Val Met Thr Gln Ser His Lys Ile Met Ser Thr Ser Val Gly
1               5                   10                  15

Asp Arg Val Ser Ile Thr Cys Lys Ala Ser Gln Asp Val Ser Asn Ile
            20                  25                  30

Val Val Trp Phe Gln Gln Lys Pro Gly Gln Ser Pro Asn Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Ser Pro Tyr
                85                  90                  95

Thr Phe Gly Gly Gly Thr Lys Leu Glu Ile Lys
            100                 105


<210> SEQ ID NO 135
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Arg Phe
            20                  25                  30

Gly Val His Trp Val Arg Gln Ser Pro Gly Lys Gly Leu Glu Trp Leu
        35                  40                  45

Gly Val Ile Trp Arg Gly Gly Ser Thr Asp Tyr Asn Ala Ala Phe Met
    50                  55                  60

Ser Arg Leu Thr Ile Thr Lys Asp Asn Ser Lys Ser Gln Val Phe Phe
65                  70                  75                  80

Lys Leu Asn Ser Leu Lys Val Asp Asp Thr Ala Ile Tyr Tyr Cys Ser
                85                  90                  95

Asn His Tyr Tyr Gly Ser Ser Asp Tyr Ala Leu Asp Asn Trp Gly Gln
            100                 105                 110

Gly Ile Ser Val Thr Val Ser Ser
        115                 120


<210> SEQ ID NO 136
<211> LENGTH: 233
<212> TYPE: PRT
<213> ORGANISM: Homo sapiens

<400> SEQUENCE: 136

Val Ala Val Pro Val Ser Arg Pro Val Leu Thr Leu Arg Ala Pro Gly
1               5                   10                  15

Thr His Ala Ala Val Gly Asp Leu Leu Glu Leu His Cys Glu Ala Leu
            20                  25                  30

Arg Gly Ser Pro Leu Ile Leu Tyr Arg Phe Phe His Glu Asp Val Thr
        35                  40                  45

Leu Gly Asn Arg Ser Ser Pro Ser Gly Gly Ala Ser Leu Asn Leu Ser
    50                  55                  60

Leu Thr Ala Glu His Ser Gly Asn Tyr Ser Cys Glu Ala Asp Asn Gly
65                  70                  75                  80
```

-continued

```
Leu Gly Ala Gln Arg Ser Glu Thr Val Thr Leu Tyr Ile Thr Gly Leu
                85                  90                  95

Thr Ala Asn Arg Ser Gly Pro Phe Ala Thr Gly Val Ala Gly Gly Leu
            100                 105                 110

Leu Ser Ile Ala Gly Leu Ala Ala Gly Ala Leu Leu Leu Tyr Cys Trp
        115                 120                 125

Leu Ser Arg Lys Ala Gly Arg Lys Pro Ala Ser Asp Pro Ala Arg Ser
    130                 135                 140

Pro Ser Asp Ser Asp Ser Gln Glu Pro Thr Tyr His Asn Val Pro Ala
145                 150                 155                 160

Trp Glu Glu Leu Gln Pro Val Tyr Thr Asn Ala Asn Pro Arg Gly Glu
                165                 170                 175

Asn Val Val Tyr Ser Glu Val Arg Ile Ile Gln Glu Lys Lys Lys His
            180                 185                 190

Ala Val Ala Ser Asp Pro Arg His Leu Arg Asn Lys Gly Ser Pro Ile
        195                 200                 205

Ile Tyr Ser Glu Val Lys Val Ala Ser Thr Pro Val Ser Gly Ser Leu
    210                 215                 220

Phe Leu Ala Ser Ser Ala Pro His Arg
225                 230
```